(12) United States Patent
Birnboim

(10) Patent No.: US 11,572,581 B2
(45) Date of Patent: *Feb. 7, 2023

(54) COMPOSITIONS AND METHODS FOR OBTAINING NUCLEIC ACIDS FROM SPUTUM

(71) Applicant: DNA GENOTEK INC., Kanata (CA)

(72) Inventor: H. Chaim Birnboim, Ottawa (CA)

(73) Assignee: DNA GENOTEK, INC., Kanata (CA)

(*) Notice: Subject to any disclaimer, the term of this patent is extended or adjusted under 35 U.S.C. 154(b) by 0 days.

This patent is subject to a terminal disclaimer.

(21) Appl. No.: 16/986,765

(22) Filed: Aug. 6, 2020

(65) Prior Publication Data
US 2020/0362395 A1 Nov. 19, 2020

Related U.S. Application Data

(60) Division of application No. 16/809,131, filed on Mar. 4, 2020, which is a continuation of application No. (Continued)

(51) Int. Cl.
| | |
|---|---|
| *C12Q 1/6806* | (2018.01) |
| *B01L 3/00* | (2006.01) |
| *C12N 15/10* | (2006.01) |

(52) U.S. Cl.
CPC ........... *C12Q 1/6806* (2013.01); *B01L 3/502* (2013.01); *B01L 3/5082* (2013.01); (Continued)

(58) Field of Classification Search
CPC ..... C12Q 1/6806; B01L 3/5082; B01L 3/502; B01L 2300/0832; B01L 2400/0683; (Continued)

(56) References Cited

U.S. PATENT DOCUMENTS

| 718,127 A | 1/1903 | Holmgren |
|---|---|---|
| 2,275,567 A | 3/1942 | Smith |
| (Continued) | | |

FOREIGN PATENT DOCUMENTS

| AU | 2006-324337 B2 | 6/2007 |
|---|---|---|
| CA | 2072331 A1 | 12/1992 |
| (Continued) | | |

OTHER PUBLICATIONS

Afkhami et al., "Spectrophotometric determination of periodate, iodate and bromate mixtures based on their reaction with iodide", Analytical Sciences (2001) 17: 1199-1202.
(Continued)

*Primary Examiner* — Benjamin R Whatley
*Assistant Examiner* — Jacqueline Brazin
(74) *Attorney, Agent, or Firm* — Lathrop GPM LLP; James H. Velema, Esq.

(57) ABSTRACT

The present invention relates to compositions and methods for preserving and extracting nucleic acids from saliva. The compositions include a chelating agent, a denaturing agent, buffers to maintain the pH of the composition within ranges desirable for DNA and/or RNA. The compositions may also include a reducing agent and/or antimicrobial agent. The invention extends to methods of using the compositions of the invention to preserve and isolate nucleic acids from saliva as well as to containers for the compositions of the invention.

30 Claims, 11 Drawing Sheets

Related U.S. Application Data

15/345,420, filed on Nov. 7, 2016, now Pat. No. 10,619,187, which is a continuation of application No. 14/549,344, filed on Nov. 20, 2014, now Pat. No. 9,523,115, which is a continuation of application No. 12/338,873, filed on Dec. 18, 2008, now abandoned, which is a continuation of application No. 10/455,680, filed on Jun. 5, 2003, now Pat. No. 7,482,116.

(60) Provisional application No. 60/386,399, filed on Jun. 7, 2002, provisional application No. 60/386,397, filed on Jun. 7, 2002, provisional application No. 60/386,398, filed on Jun. 7, 2002.

(52) U.S. Cl.
CPC .... *C12N 15/1003* (2013.01); *B01L 2300/042* (2013.01); *B01L 2300/046* (2013.01); *B01L 2300/047* (2013.01); *B01L 2300/0672* (2013.01); *B01L 2300/0832* (2013.01); *B01L 2400/0683* (2013.01)

(58) Field of Classification Search
CPC ......... B01L 2300/046; B01L 2300/042; B01L 2300/0672; B01L 2300/047; C12N 15/1003; A61B 10/0051
USPC ....................................................... 422/527
See application file for complete search history.

(56) References Cited

U.S. PATENT DOCUMENTS

| | | |
|---|---|---|
| 2,631,521 A | 3/1953 | Atkins |
| D169,994 S | 7/1953 | Soffer et al. |
| 2,653,611 A | 9/1953 | Smith |
| D175,257 S | 8/1955 | Hopkins |
| 2,764,983 A | 10/1956 | Barasch |
| 2,773,591 A | 12/1956 | Jensen |
| 2,793,776 A | 5/1957 | Ipari |
| 2,958,439 A | 11/1960 | Yochem |
| D196,112 S | 8/1963 | Esser |
| 3,199,704 A | 8/1965 | Davidson |
| 3,321,097 A | 5/1967 | Solowey |
| 3,340,873 A | 9/1967 | Solowey |
| 3,347,410 A | 12/1967 | Schwartzman |
| 3,419,179 A | 12/1968 | Deuschle et al. |
| D213,292 S | 2/1969 | Arsenault |
| 3,441,179 A | 4/1969 | Ragan |
| 3,464,414 A | 9/1969 | Sponnoble |
| 3,518,164 A | 6/1970 | Andelin et al. |
| 3,536,191 A | 10/1970 | Williams |
| 3,537,606 A | 11/1970 | Solowey |
| D221,751 S | 9/1971 | Kronish et al. |
| 3,603,484 A | 9/1971 | Ogle |
| 3,651,990 A | 3/1972 | Cernei |
| 3,674,028 A | 7/1972 | Ogle |
| 3,694,455 A | 9/1972 | Dunn |
| 3,731,853 A | 5/1973 | Baumann |
| 3,799,426 A | 3/1974 | Pates et al. |
| 3,815,580 A | 6/1974 | Oster |
| 3,831,742 A | 8/1974 | Gardella et al. |
| D233,138 S | 10/1974 | Vogel |
| 3,846,077 A | 11/1974 | Ohringer |
| 3,968,872 A | 7/1976 | Cavazza |
| D241,416 S | 9/1976 | Aul |
| D244,555 S | 5/1977 | Wiedmann |
| D246,600 S | 12/1977 | Kurata |
| D246,698 S | 12/1977 | Morris |
| 4,081,356 A | 3/1978 | Zierdt |
| 4,089,432 A | 5/1978 | Crankshaw |
| 4,102,451 A | 7/1978 | Clarke et al. |
| 4,131,016 A | 12/1978 | Layton |
| 4,140,489 A | 2/1979 | Lee |
| 4,150,950 A | 4/1979 | Takeguchi et al. |
| D252,612 S | 8/1979 | Mull |
| 4,170,798 A | 10/1979 | Krumdieck |
| 4,175,008 A | 11/1979 | White |
| 4,184,483 A | 1/1980 | Greenspan |
| 4,195,730 A | 4/1980 | Hunt |
| 4,200,100 A | 4/1980 | Willis |
| D255,092 S | 5/1980 | Wong |
| D256,053 S | 7/1980 | Steigerwald |
| 4,217,798 A | 8/1980 | McCarthy et al. |
| 4,221,291 A | 9/1980 | Hunt |
| 4,301,812 A | 11/1981 | Layton et al. |
| 4,312,950 A | 1/1982 | Snyder et al. |
| 4,324,859 A | 4/1982 | Saxholm |
| 4,340,147 A | 7/1982 | McIntosh |
| 4,386,696 A | 6/1983 | Goncalves |
| 4,418,702 A | 12/1983 | Brown et al. |
| D274,132 S | 6/1984 | Nightingale |
| 4,465,183 A | 8/1984 | Saito et al. |
| D277,736 S | 2/1985 | Long |
| 4,505,433 A | 3/1985 | Selenke |
| 4,583,971 A | 4/1986 | Bocquet et al. |
| 4,589,548 A | 5/1986 | Fay |
| 4,591,050 A | 5/1986 | Finke et al. |
| D285,115 S | 8/1986 | Proud et al. |
| 4,615,437 A | 10/1986 | Finke et al. |
| D286,546 S | 11/1986 | Funahashi |
| D287,570 S | 1/1987 | Olsen |
| 4,634,003 A | 1/1987 | Ueda et al. |
| 4,663,161 A | 5/1987 | Mannino et al. |
| 4,678,559 A | 7/1987 | Szabados |
| 4,727,985 A | 3/1988 | McNeirney et al. |
| 4,741,346 A | 5/1988 | Wong et al. |
| D296,241 S | 6/1988 | Miskinis |
| 4,753,358 A | 6/1988 | Virca et al. |
| 4,761,379 A | 8/1988 | Williams et al. |
| 4,785,931 A | 11/1988 | Weir et al. |
| 4,832,917 A | 5/1989 | Elliott |
| D303,710 S | 9/1989 | Neill |
| 4,914,023 A | 4/1990 | Philo et al. |
| 4,918,178 A | 4/1990 | Hurley et al. |
| 4,927,605 A | 5/1990 | Dorn et al. |
| 4,932,081 A | 6/1990 | Burns |
| 4,935,342 A | 6/1990 | Seligson et al. |
| D310,264 S | 8/1990 | Leoncavallo et al. |
| 4,982,553 A | 1/1991 | Ltoh |
| 4,982,875 A | 1/1991 | Pozzi |
| 4,999,288 A | 3/1991 | deCastro |
| D318,727 S | 7/1991 | Spike |
| 5,029,718 A | 7/1991 | Rizzardi |
| 5,066,463 A | 11/1991 | Chang |
| 5,091,316 A | 2/1992 | Monthony et al. |
| D325,444 S | 4/1992 | Murashita et al. |
| 5,128,104 A | 7/1992 | Murphy et al. |
| 5,140,043 A | 8/1992 | Darr et al. |
| D330,011 S | 10/1992 | Miller |
| 5,152,965 A | 10/1992 | Fisk et al. |
| 5,196,182 A | 3/1993 | Ryan |
| D338,956 S | 8/1993 | Hadaway et al. |
| 5,234,809 A | 8/1993 | Boom et al. |
| 5,268,148 A | 12/1993 | Seymour |
| 5,283,038 A | 2/1994 | Seymour |
| D344,804 S | 3/1994 | Muniz |
| 5,291,991 A | 3/1994 | Meyer |
| 5,330,048 A | 7/1994 | Haber et al. |
| 5,335,673 A | 8/1994 | Goldstein et al. |
| 5,364,763 A | 11/1994 | Kacian |
| 5,376,527 A | 12/1994 | Robson et al. |
| 5,380,492 A | 1/1995 | Seymour |
| 5,384,096 A | 1/1995 | Burns |
| D355,606 S | 2/1995 | Manera |
| 5,393,496 A | 2/1995 | Seymour |
| 5,396,986 A | 3/1995 | Fountain et al. |
| D357,985 S | 5/1995 | Bums |
| 5,422,273 A | 6/1995 | Garrison et al. |
| 5,425,921 A | 6/1995 | Coakley et al. |
| D362,184 S | 9/1995 | Carr |
| D362,623 S | 9/1995 | Ma |
| 5,477,863 A | 12/1995 | Grant |
| 5,478,722 A | 12/1995 | Caldwell |

(56) References Cited

U.S. PATENT DOCUMENTS

| | | | |
|---|---|---|---|
| D367,114 S | 2/1996 | Wilson et al. |
| 5,490,971 A | 2/1996 | Gifford et al. |
| 5,494,646 A | 2/1996 | Seymour |
| 5,496,562 A | 3/1996 | Burgoyne |
| 5,512,440 A | 4/1996 | Down et al. |
| D372,093 S | 7/1996 | Sampson et al. |
| 5,540,326 A | 7/1996 | Arnold et al. |
| 5,556,544 A | 9/1996 | Didier |
| D375,160 S | 10/1996 | Sampson et al. |
| 5,567,309 A | 10/1996 | Glasson et al. |
| 5,624,554 A | 4/1997 | Faulkner et al. |
| D379,663 S | 6/1997 | Pearson et al. |
| 5,643,767 A | 7/1997 | Fischetti et al. |
| 5,658,531 A | 8/1997 | Cope et al. |
| D383,214 S | 9/1997 | Brennan |
| D383,851 S | 9/1997 | Wong |
| D385,793 S | 11/1997 | Marsal |
| D388,519 S | 12/1997 | Skiffington et al. |
| 5,692,644 A | 12/1997 | Gueret |
| 5,707,860 A | 1/1998 | Collis et al. |
| 5,714,341 A | 2/1998 | Thieme et al. |
| D392,187 S | 3/1998 | King |
| 5,736,322 A | 4/1998 | Goldstein |
| 5,736,355 A | 4/1998 | Dyke et al. |
| 5,756,126 A | 5/1998 | Burgoyne |
| 5,786,208 A | 7/1998 | Clark et al. |
| 5,786,228 A * | 7/1998 | Charlton .......... A61B 10/0045 |
| | | 210/359 |
| 5,788,652 A | 8/1998 | Rahn |
| 5,807,527 A | 9/1998 | Burgoyne |
| 5,814,442 A | 9/1998 | Natarajan et al. |
| 5,817,630 A | 10/1998 | Hofmann et al. |
| 5,827,675 A | 10/1998 | Skiffington et al. |
| D401,697 S | 11/1998 | Cloonan et al. |
| 5,829,696 A | 11/1998 | DeStefano et al. |
| 5,830,154 A | 11/1998 | Goldstein et al. |
| 5,830,410 A | 11/1998 | Thieme et al. |
| 5,837,452 A | 11/1998 | Clark et al. |
| D402,766 S | 12/1998 | Smith et al. |
| 5,843,654 A | 12/1998 | Heisler et al. |
| 5,849,890 A | 12/1998 | Gold |
| 5,869,328 A | 2/1999 | Antoci et al. |
| 5,871,905 A | 2/1999 | Thieme et al. |
| 5,909,753 A | 6/1999 | Rossi et al. |
| 5,910,407 A | 6/1999 | Vogelstein et al. |
| D412,107 S | 7/1999 | Bosshardt |
| 5,921,396 A | 7/1999 | Brown |
| 5,927,549 A | 7/1999 | Wood |
| 5,933,498 A | 8/1999 | Schneck et al. |
| 5,935,804 A | 8/1999 | Laine |
| 5,935,864 A | 8/1999 | Schramm et al. |
| 5,939,262 A | 8/1999 | Pasloske et al. |
| 5,941,380 A | 8/1999 | Rothman |
| 5,950,819 A | 9/1999 | Sellars |
| 5,962,237 A | 10/1999 | Ts'o et al. |
| 5,967,309 A | 10/1999 | Robles-Gonzalez et al. |
| 5,968,746 A | 10/1999 | Schneider |
| 5,976,829 A | 11/1999 | Birnboim |
| 5,980,834 A | 11/1999 | Bruno |
| 5,984,141 A | 11/1999 | Gibler |
| 5,992,693 A | 11/1999 | Albisetti |
| 6,003,728 A | 12/1999 | Elliott |
| 6,020,186 A | 2/2000 | Henco et al. |
| 6,020,196 A | 2/2000 | Hu et al. |
| 6,048,091 A | 4/2000 | McIntyre et al. |
| D424,440 S | 5/2000 | Wilkinson et al. |
| D425,618 S | 5/2000 | Niermann et al. |
| D425,625 S | 5/2000 | Niennann |
| D426,313 S | 6/2000 | Woolston et al. |
| 6,071,745 A | 6/2000 | Lin et al. |
| 6,076,570 A | 6/2000 | Byrne |
| 6,084,091 A | 7/2000 | Muller et al. |
| 6,090,793 A | 7/2000 | Zimmerman et al. |
| 6,113,257 A | 9/2000 | Sharon et al. |
| 6,113,583 A | 9/2000 | Fowles et al. |
| 6,121,055 A | 9/2000 | Hargreaves |
| D432,245 S | 10/2000 | Stevens |
| 6,135,275 A | 10/2000 | Kelders et al. |
| 6,138,821 A | 10/2000 | Hsu |
| 6,148,996 A | 11/2000 | Morini |
| 6,149,866 A | 11/2000 | Luotola et al. |
| 6,152,296 A | 11/2000 | Shih |
| 6,168,922 B1 | 1/2001 | Harvey et al. |
| 6,170,719 B1 | 1/2001 | Wilkinson et al. |
| 6,176,836 B1 | 1/2001 | Trudil et al. |
| D437,786 S | 2/2001 | van Swieten et al. |
| 6,182,845 B1 | 2/2001 | Wolfe et al. |
| 6,187,546 B1 | 2/2001 | O'Neill et al. |
| 6,190,875 B1 | 2/2001 | Ben-Artzi |
| 6,204,375 B1 | 3/2001 | Lader |
| D442,090 S | 5/2001 | Jackson et al. |
| 6,224,922 B1 | 5/2001 | Fonte |
| 6,228,323 B1 | 5/2001 | Asgharian et al. |
| 6,235,010 B1 | 5/2001 | Wilkinson et al. |
| 6,235,466 B1 | 5/2001 | Branch et al. |
| 6,242,188 B1 | 6/2001 | Dattagupta et al. |
| 6,247,586 B1 | 6/2001 | Herzog et al. |
| D445,908 S | 7/2001 | Conway |
| 6,270,970 B1 | 8/2001 | Smith |
| 6,277,646 B1 | 8/2001 | Guirguis et al. |
| D447,812 S | 9/2001 | Conway |
| 6,291,178 B1 | 9/2001 | Schneider |
| 6,303,081 B1 | 10/2001 | Mink et al. |
| 6,309,827 B1 | 10/2001 | Goldstein et al. |
| 6,310,195 B1 | 10/2001 | Colucci et al. |
| 6,313,286 B1 | 11/2001 | Brown |
| 6,350,578 B1 | 2/2002 | Stark |
| D455,908 S | 4/2002 | Liu |
| 6,379,315 B1 | 4/2002 | Claren et al. |
| D457,247 S | 5/2002 | Iheme |
| 6,383,393 B1 | 5/2002 | Colpan et al. |
| 6,409,528 B1 | 6/2002 | Bodnar |
| 6,428,962 B1 | 8/2002 | Naegele |
| 6,448,002 B1 | 9/2002 | Hillebrand et al. |
| 6,458,546 B1 | 10/2002 | Baker |
| 6,471,069 B2 | 10/2002 | Lin |
| D465,731 S | 11/2002 | Brant et al. |
| D467,665 S | 12/2002 | Niedbala et al. |
| 6,489,172 B1 | 12/2002 | Bachand et al. |
| 6,503,716 B1 * | 1/2003 | Lai .................... C12N 15/1003 |
| | | 435/6.16 |
| D470,240 S | 2/2003 | Niedbala et al. |
| 6,524,530 B1 * | 2/2003 | Igarashi ................ B01L 3/5029 |
| | | 422/411 |
| 6,524,795 B1 | 2/2003 | Francis et al. |
| D471,234 S | 3/2003 | Okutani |
| D471,639 S | 3/2003 | McMichael et al. |
| 6,527,110 B2 | 3/2003 | Moscovitz |
| 6,528,641 B2 | 3/2003 | Lader |
| 6,533,113 B2 | 3/2003 | Mozcovitz |
| 6,539,817 B2 | 4/2003 | Kozak et al. |
| 6,543,612 B2 | 4/2003 | Lee et al. |
| 6,548,256 B2 | 4/2003 | Lienau et al. |
| 6,551,777 B1 | 4/2003 | Shuber et al. |
| D474,280 S | 5/2003 | Niedbala et al. |
| 6,562,300 B2 | 5/2003 | Rosen et al. |
| 6,602,718 B1 | 8/2003 | Augello et al. |
| 6,617,170 B2 | 9/2003 | Augello et al. |
| 6,627,152 B1 | 9/2003 | Wong |
| 6,632,662 B1 | 10/2003 | Broyer et al. |
| 6,634,234 B1 | 10/2003 | Haas |
| 6,634,243 B1 | 10/2003 | Wickstead et al. |
| 6,664,379 B1 | 12/2003 | Kudlicki et al. |
| 6,667,053 B1 | 12/2003 | Ahmad et al. |
| 6,716,392 B1 | 4/2004 | Putcha et al. |
| 6,777,210 B1 | 8/2004 | Pasloske et al. |
| 6,815,541 B1 | 11/2004 | Usui et al. |
| 6,838,560 B1 | 1/2005 | Marciacq et al. |
| 6,849,403 B1 | 2/2005 | Shuber |
| 6,852,495 B2 | 2/2005 | Kouichi |
| 6,869,769 B2 | 3/2005 | Burgoyne |
| 6,880,771 B2 | 4/2005 | Deppermann |
| D507,351 S | 7/2005 | Birnboim |
| 6,913,932 B2 | 7/2005 | Maples et al. |

(56) References Cited

U.S. PATENT DOCUMENTS

| | | | |
|---|---|---|---|
| 6,979,449 B1 | 12/2005 | Mock | |
| 6,992,182 B1 | 1/2006 | Muller et al. | |
| 7,001,724 B1 | 2/2006 | Greenfield | |
| 7,029,840 B2 | 4/2006 | McMillian | |
| 7,041,484 B1 | 5/2006 | Baga | |
| 7,178,683 B2 | 2/2007 | Birkmayer et al. | |
| 7,214,484 B2 | 5/2007 | Weber et al. | |
| 7,267,980 B1 | 9/2007 | Motari et al. | |
| 7,270,953 B2 | 9/2007 | Hollander et al. | |
| 7,297,485 B2 | 11/2007 | Bornar et al. | |
| 7,300,632 B2 | 11/2007 | Sugiyama et al. | |
| D562,462 S | 2/2008 | Muir et al. | |
| 7,338,634 B2 | 3/2008 | Chang | |
| D574,507 S | 8/2008 | Muir et al. | |
| 7,482,116 B2 * | 1/2009 | Birnboim | B01L 3/5082 536/25.4 |
| 7,666,609 B1 | 2/2010 | Guo et al. | |
| 7,749,757 B1 | 7/2010 | Mortari et al. | |
| D631,350 S | 1/2011 | Beach et al. | |
| D631,554 S | 1/2011 | Jackson et al. | |
| 7,935,483 B2 | 5/2011 | Tatsuo et al. | |
| D640,794 S | 6/2011 | Sunstrum et al. | |
| D640,795 S | 6/2011 | Jackson et al. | |
| 8,158,357 B2 | 4/2012 | Birnboim et al. | |
| 8,221,381 B2 | 7/2012 | Muir et al. | |
| 8,470,536 B2 | 6/2013 | Birnboim et al. | |
| 8,728,414 B2 | 5/2014 | Beach et al. | |
| 9,072,499 B2 | 7/2015 | Birnboim et al. | |
| 9,079,181 B2 | 7/2015 | Curry et al. | |
| D743,044 S | 11/2015 | Jackson et al. | |
| D743,571 S | 11/2015 | Jackson et al. | |
| 9,207,164 B2 | 12/2015 | Muir et al. | |
| 9,442,046 B2 | 9/2016 | Biadillah et al. | |
| 9,523,115 B2 | 12/2016 | Birnboim | |
| 10,000,795 B2 | 6/2018 | Birnboim et al. | |
| D850,647 S | 6/2019 | Jackson et al. | |
| 10,435,735 B2 | 10/2019 | Birnboim et al. | |
| 10,576,468 B2 | 3/2020 | Biadillah et al. | |
| 10,619,187 B2 | 4/2020 | Birnboim | |
| D890,359 S | 7/2020 | Jackson et al. | |
| 10,767,215 B2 | 9/2020 | Birnboim | |
| 11,002,646 B2 | 5/2021 | Biadillah et al. | |
| 11,046,949 B2 | 6/2021 | Birnboim et al. | |
| 2001/0008614 A1 * | 7/2001 | Aronowitz | G01N 1/405 422/400 |
| 2001/0023072 A1 | 9/2001 | Crawford et al. | |
| 2001/0034066 A1 | 10/2001 | Alam | |
| 2001/0039058 A1 | 11/2001 | Ilheme et al. | |
| 2002/0004206 A1 | 1/2002 | Berger et al. | |
| 2002/0026046 A1 | 2/2002 | Pasloske et al. | |
| 2002/0037512 A1 | 3/2002 | Baker | |
| 2002/0061260 A1 | 5/2002 | Husar | |
| 2002/0064802 A1 | 5/2002 | Raschke et al. | |
| 2002/0068292 A1 | 6/2002 | Kojima | |
| 2002/0081575 A1 | 6/2002 | Small et al. | |
| 2002/0092852 A1 | 7/2002 | Stewart et al. | |
| 2002/0098200 A1 | 7/2002 | Campos-Neto et al. | |
| 2002/0115980 A1 | 8/2002 | Niedospial | |
| 2002/0127147 A1 | 9/2002 | Kacian | |
| 2002/0146677 A1 | 10/2002 | Augello et al. | |
| 2002/0150937 A1 | 10/2002 | Lenteichia et al. | |
| 2002/0177139 A1 | 11/2002 | Greenfield et al. | |
| 2002/0179461 A1 | 12/2002 | Mollstam et al. | |
| 2002/0185389 A1 | 12/2002 | Kelders et al. | |
| 2002/0192651 A1 | 12/2002 | Wheeler | |
| 2002/0197275 A1 | 12/2002 | Sunvold et al. | |
| 2002/0197631 A1 | 12/2002 | Lawrence et al. | |
| 2003/0008379 A1 | 1/2003 | Bhosle | |
| 2003/0013112 A1 | 1/2003 | Sprenger-Haussels | |
| 2003/0049675 A1 | 3/2003 | Libragen | |
| 2003/0064526 A1 | 4/2003 | Neidbala et al. | |
| 2003/0073830 A1 | 4/2003 | Heath et al. | |
| 2003/0086830 A1 | 5/2003 | Haywood et al. | |
| 2003/0089627 A1 | 5/2003 | Chelles et al. | |
| 2003/0091989 A1 | 5/2003 | Davis et al. | |
| 2003/0109548 A1 | 6/2003 | Royt et al. | |
| 2003/0114430 A1 | 6/2003 | MacLeod et al. | |
| 2003/0132244 A1 | 7/2003 | Birkmayer et al. | |
| 2003/0143752 A1 | 7/2003 | Feldsine et al. | |
| 2003/0170694 A1 | 9/2003 | Wall et al. | |
| 2003/0172065 A1 | 9/2003 | Sorenson et al. | |
| 2003/0181826 A1 | 9/2003 | Smith et al. | |
| 2003/0215954 A1 | 11/2003 | Cockerill, III et al. | |
| 2003/0229222 A1 | 12/2003 | Kojima | |
| 2004/0014104 A1 | 1/2004 | Shuber | |
| 2004/0018120 A1 | 1/2004 | Rappin et al. | |
| 2004/0018575 A1 | 1/2004 | Rappin et al. | |
| 2004/0019196 A1 | 1/2004 | Bair, Jr. et al. | |
| 2004/0038269 A1 * | 2/2004 | Birnboim | C12Q 1/6806 435/6.1 |
| 2004/0038424 A1 | 2/2004 | Maples | |
| 2004/0049805 A1 | 3/2004 | Lerchl et al. | |
| 2004/0050700 A1 | 3/2004 | Lopez-Canovas et al. | |
| 2004/0062785 A1 | 4/2004 | Parker | |
| 2004/0111763 A1 | 6/2004 | Heinz et al. | |
| 2004/0132091 A1 | 7/2004 | Ramsey et al. | |
| 2004/0157219 A1 | 8/2004 | Lou et al. | |
| 2004/0157223 A1 | 8/2004 | Lou et al. | |
| 2004/0161788 A1 | 8/2004 | Chen et al. | |
| 2004/0197845 A1 | 10/2004 | Hassibi et al. | |
| 2004/0200740 A1 | 10/2004 | Cho | |
| 2004/0200741 A1 | 10/2004 | Cho | |
| 2004/0200742 A1 | 10/2004 | Cho | |
| 2004/0209332 A1 | 10/2004 | Marciacq | |
| 2004/0226835 A1 | 11/2004 | Takahashi et al. | |
| 2004/0229264 A1 | 11/2004 | Crossman et al. | |
| 2004/0245125 A1 | 12/2004 | Trkulja | |
| 2005/0096563 A1 * | 5/2005 | Liang | A61B 10/0051 600/573 |
| 2005/0181363 A1 | 8/2005 | Kamata et al. | |
| 2005/0227303 A1 | 10/2005 | Guo et al. | |
| 2005/0239045 A1 | 10/2005 | Okamoto et al. | |
| 2006/0029972 A1 | 2/2006 | Lorenz | |
| 2006/0139631 A1 | 6/2006 | Feldsine et al. | |
| 2007/0031880 A1 | 2/2007 | Lou et al. | |
| 2007/0178508 A1 | 8/2007 | Kamata et al. | |
| 2009/0162866 A1 | 6/2009 | Birnboim | |
| 2009/0162924 A1 | 6/2009 | Birnboim | |
| 2010/0241091 A1 * | 9/2010 | Wu | A61M 1/604 604/319 |
| 2011/0212002 A1 | 9/2011 | Curry et al. | |
| 2012/0061392 A1 | 3/2012 | Beach et al. | |
| 2017/0016807 A1 | 1/2017 | Biadillah et al. | |
| 2017/0072393 A1 | 3/2017 | Jackson et al. | |
| 2017/0130219 A1 | 5/2017 | Birnboim et al. | |
| 2017/0182196 A1 * | 6/2017 | Patel | A61L 11/00 |
| 2017/0226469 A1 | 8/2017 | Birnboim et al. | |
| 2018/0031543 A1 | 2/2018 | Andrews et al. | |
| 2018/0235206 A1 * | 8/2018 | Laughlin | C12Q 1/6806 |
| 2018/0313726 A1 | 11/2018 | Biadillah et al. | |
| 2019/0210778 A1 | 7/2019 | Muir et al. | |
| 2019/0358628 A1 | 11/2019 | Curry et al. | |
| 2020/0022684 A1 * | 1/2020 | Sessions | B01L 3/50825 |
| 2020/0239931 A1 | 7/2020 | Birnboim et al. | |
| 2020/0284704 A1 | 9/2020 | Biadillah et al. | |
| 2020/0316493 A1 | 10/2020 | Birnboim et al. | |
| 2020/0354769 A1 | 11/2020 | Birnboim | |
| 2020/0398267 A1 | 12/2020 | Biadillah et al. | |

FOREIGN PATENT DOCUMENTS

| | | |
|---|---|---|
| CA | 1326809 C | 2/1994 |
| CA | 2315257 A1 | 7/1999 |
| CA | 2236240 A1 | 10/1999 |
| CA | 2384368 A1 | 3/2001 |
| CA | 2142910 C | 8/2002 |
| CA | 101498 S | 1/2004 |
| CA | 2515039 A1 | 8/2004 |
| CA | 2522446 A1 | 11/2004 |
| CA | 113861 S | 8/2007 |
| CA | 118249 S | 8/2007 |
| CN | 2598551 Y | 1/2004 |
| CN | 1503910 A | 6/2004 |
| CN | 101370425 B | 8/2011 |

(56) References Cited

FOREIGN PATENT DOCUMENTS

| | | |
|---|---|---|
| DE | 2554379 A1 | 6/1976 |
| DE | 19720153 A1 | 12/1997 |
| DE | 19950884 A1 | 4/2001 |
| DE | 10219117 C1 | 10/2003 |
| EM | 000522339-0001 | 4/2006 |
| EM | 000522339-0002 | 4/2006 |
| EP | 0215735 A1 | 3/1987 |
| EP | 0240341 A2 | 10/1987 |
| EP | 0273015 A2 | 6/1988 |
| EP | 0285439 A2 | 10/1988 |
| EP | 0338591 A2 | 10/1989 |
| EP | 0487028 A2 | 5/1992 |
| EP | 0586024 B1 | 3/1994 |
| EP | 0265519 B1 | 9/1995 |
| EP | 0734684 A1 | 10/1996 |
| EP | 0939118 A1 | 9/1999 |
| EP | 1207208 A2 | 5/2002 |
| EP | 1362927 A1 | 11/2003 |
| EP | 1391520 A1 | 2/2004 |
| EP | 1527172 B1 | 11/2008 |
| EP | 1238103 B1 | 1/2009 |
| EP | 1506995 B1 | 10/2009 |
| EP | 2110442 A1 | 10/2009 |
| FR | 2279378 A1 | 2/1976 |
| GB | 725784 A | 3/1955 |
| GB | 1403274 A | 8/1975 |
| JP | 58-96365 U | 1/1985 |
| JP | 60-4433 U | 1/1985 |
| JP | S62-253395 A | 11/1987 |
| JP | S63-070954 U | 5/1988 |
| JP | 2-42972 A | 2/1990 |
| JP | 5-99923 A | 4/1993 |
| JP | S62-153725 A | 4/1993 |
| JP | H5-94765 U | 12/1993 |
| JP | H06500403 A | 1/1994 |
| JP | H06-078282 U | 11/1994 |
| JP | H09-500723 A | 1/1997 |
| JP | H09-168399 A | 6/1997 |
| JP | H09-193977 | 7/1997 |
| JP | H10-132824 A | 5/1998 |
| JP | H10273161 A | 10/1998 |
| JP | H10-512140 A | 11/1998 |
| JP | 10-332734 A | 12/1998 |
| JP | 11-183468 A | 7/1999 |
| JP | 2000-501191 A | 2/2000 |
| JP | 2000-501931 A1 | 2/2000 |
| JP | 2000-508171 A | 7/2000 |
| JP | 2001-524321 A | 12/2001 |
| JP | 2002-156317 A | 5/2002 |
| JP | 2002-514084 A | 5/2002 |
| JP | 2003-344232 A | 12/2003 |
| JP | 2004-008094 A | 1/2004 |
| JP | 2004-008107 A | 1/2004 |
| JP | 2004-222795 A | 8/2004 |
| JP | 2005-536550 A | 12/2005 |
| JP | 4-092141 B | 5/2008 |
| JP | 4092139 B2 | 5/2008 |
| JP | 2011-36247 A | 2/2011 |
| RU | 2101354 C1 | 1/1998 |
| RU | 2241004 C2 | 11/2004 |
| WO | WO 1987/006706 A1 | 11/1987 |
| WO | WO 1989/006704 A1 | 7/1989 |
| WO | WO 1991/002740 A1 | 3/1991 |
| WO | WO 1992/017110 | 10/1992 |
| WO | WO 1993/020235 A1 | 10/1993 |
| WO | WO 1994/012657 A1 | 6/1994 |
| WO | WO 1994/012881 A2 | 6/1994 |
| WO | WO 1994/029691 A | 12/1994 |
| WO | WO 1996/000228 A1 | 1/1996 |
| WO | WO 1996/014017 A1 | 5/1996 |
| WO | WO 1996/020403 A1 | 7/1996 |
| WO | WO 1997/005248 A2 | 2/1997 |
| WO | WO 1997/007207 A1 | 2/1997 |
| WO | WO 1997/019191 A1 | 5/1997 |
| WO | WO 1997/021102 A1 | 6/1997 |
| WO | WO 1997/021605 A1 | 6/1997 |
| WO | WO 1997/024979 A1 | 7/1997 |
| WO | WO 1997/038313 A1 | 10/1997 |
| WO | WO 1997/048492 A1 | 12/1997 |
| WO | WO 1998/003265 A1 | 1/1998 |
| WO | WO 1998/004899 | 2/1998 |
| WO | WO 1998/012351 A1 | 3/1998 |
| WO | WO 1998/038917 | 9/1998 |
| WO | WO 1998/044158 A1 | 10/1998 |
| WO | WO 1998/053075 A2 | 11/1998 |
| WO | WO 1998/058081 A1 | 12/1998 |
| WO | WO 1999/000521 A1 | 1/1999 |
| WO | WO 1999/022868 A1 | 5/1999 |
| WO | WO 1999/027139 A1 | 6/1999 |
| WO | WO 1999/029904 A2 | 6/1999 |
| WO | WO 2000/005338 A1 | 2/2000 |
| WO | WO 2000/008136 A1 | 2/2000 |
| WO | WO 2000/010884 | 3/2000 |
| WO | WO 2000/029618 A1 | 5/2000 |
| WO | WO 2000/031303 A2 | 6/2000 |
| WO | WO 2000/042177 A1 | 7/2000 |
| WO | WO 2000/049416 A2 | 8/2000 |
| WO | WO 2000/050626 A1 | 8/2000 |
| WO | WO 2000/050640 A1 | 8/2000 |
| WO | WO 2000/066606 A1 | 11/2000 |
| WO | WO 2000/078150 A1 | 12/2000 |
| WO | WO 2001/019395 A1 | 3/2001 |
| WO | WO 2001/032886 A2 | 5/2001 |
| WO | WO 2001/034844 A1 | 5/2001 |
| WO | WO 2001/040277 A2 | 6/2001 |
| WO | WO 2001/042503 A2 | 6/2001 |
| WO | WO 2001/059128 A2 | 8/2001 |
| WO | WO 2001/060517 A2 | 8/2001 |
| WO | WO 2002/000599 A1 | 1/2002 |
| WO | WO 2002/038802 A1 | 5/2002 |
| WO | WO 2002/042410 A2 | 5/2002 |
| WO | WO 2002/044691 A2 | 6/2002 |
| WO | WO 2002/056030 | 7/2002 |
| WO | WO 2002/057464 A2 | 7/2002 |
| WO | WO 2002/059379 A2 | 8/2002 |
| WO | WO 2002/068664 A1 | 9/2002 |
| WO | WO 2002/088296 | 11/2002 |
| WO | WO 2003/033724 A2 | 4/2003 |
| WO | WO 2003/033739 A1 | 4/2003 |
| WO | WO 2003/037739 A1 | 5/2003 |
| WO | WO 2003/104251 A2 | 12/2003 |
| WO | WO 2004/017895 A2 | 3/2004 |
| WO | WO 2004/033336 A1 | 4/2004 |
| WO | WO 2004/033470 A2 | 4/2004 |
| WO | WO 2004/046348 A1 | 6/2004 |
| WO | WO 2004/072229 A2 | 8/2004 |
| WO | WO 2004/094635 A2 | 11/2004 |
| WO | WO 2004/107985 A1 | 12/2004 |
| WO | WO 2004/108205 A1 | 12/2004 |
| WO | WO 2006/096973 A1 | 9/2006 |
| WO | WO 2007/068094 A1 | 6/2007 |
| WO | WO-2008020013 A2 * | 2/2008 ....... A61B 5/150022 |
| WO | WO-2010075265 A2 * | 7/2010 ........... G01N 33/497 |

OTHER PUBLICATIONS

American Thoracic Society, "Diagnostic Standards and Classification of Tuberculosis in Adults and Children", American Thoracic Society and the Centers for Disease Control and Prevention (2000) Am J Respir Crit Care Med, 161: 1376-1395.

Aries et al., "Bacteria and the aetiology of cancer of the large bowel", Gut, 1969, 10, 334-335.

Bickley et al., "Analytical Molecular Biology: Quality and Validation", Royal Society of Chemistry (1999) Chapter 6 Inhibitors and Enhancers of PCR; pp. 81-102 [Editors: Parkes, Helen C., Saunders, Ginny C.]

Boom et al., "Rapid and Simple Method for Purification of Nucleic Acids", J. Clin. Microbiol., 1990, 28(3): 495-503.

Brusa et al., "Oxygen Tolerance of Anaerobic Bacteria Isolated from Human Feces", Current Microbiology (1989) vol. 19, pp. 39-43.

Burton et al., "Studies of Nucleotide Sequences in Deoxyribonucleic Acid", Cold Spring Harbor Symposium on Quantitative Biology, vol. 28, pp. 27-34 (1963).

(56) References Cited

OTHER PUBLICATIONS

Caldas et al., "Detection of K-ras Mutations in the Stool of Patients with Pancreatic Adenocarcinoma and Pancreatic Ductal Hyperplasia", Cancer Res., 1994, 54: 3568-3573.

Carricajo et al., "Evaluation of BacT/Alert 3D Liquid Culture System for Recovery of Mycobacteria from Clinical Specimens Using Sodium Dodecyl (Lauryl) Sulfate-NaOH Decontamination", J. Clin. Microbiol. (2001) 39(10): 3799-3800.

Chassy, "A gentle method for the lysis of oral *Streptococci*", Biochem Biophys Res Commun, 68: 603-608 (1976).

Corbett et al. (May 12, 2003) "The growing burden of tuberculosis: global trends and interactions with the HIV epidemic", Arch Intern Med, 163: 1009-1021.

Daniel et al., "On the mechanicnisms whereby EDTA. EGTA. DTPA. OXALATE. Desferrioxamine, AND 1,10-phenanthroline affect contractility of rat uterus", Canadian Journal of Physiology and Pharmacology (1965) vol. 43, pp. 111-136.

Desjardin et al., "Measurement of sputum Mycobacterium tuberculosis messenger RNA as a surrogate for response to chemotherapy" (1999) Am J Respir Crit Care Med, 160:203-210.

Deuter et al., "A method for preparation of fecal DNA suitable for PCR", Nucleic Acids Research, 1995, vol. 23, No. 18, pp. 3800-3801.

Effthimiadis et al. (2002) "Induced sputum: Time from expectoration to processing", Eur Respir J., 19:706-708.

Fawley et al. (2001) "Molecular epidemiology of endemic Clostridium difficile infection", Epidemiology and Infection, 126(3): 343-350, ISSN 0950-2688.

Gallagher, "Quantitation of Nucleic Acids with Absorption Spectroscopy", Sep. 1, 1998 (Sep. 1, 1998), XP055419161, Retrieved from the Internet: URL:http://onlinelibrary.wiley.com/store/10.1002/0471140864.psa04ks13/asset/psa04k.pdf? V=1&t=j973wht9&s=3da536c696b35b2d087b89e6d20ae1133cc 4279 [retrieved on Oct. 25, 2017].

Greenwood et al., Chemistry of the Elements, 2nd Edition, Butterworth Heinemann, Oxford, Chapter 17, pp. 789-887 (1998).

Hammerschlag et al. (1980) "Bacteriology of sputum in cystic fibrosis: Evaluation of dithiothreitol as a mucolytic agent", J Clin Microbiol., 11(6): 552-557.

Heaton et al. (1992) "Defecation frequency and timing, and stool form in the general population: a prospective study", Gut 33(6): 818-824.

Hobby et al. (1973) "Enumeration of tubercle bacilli in sputum of patients with pulmonary tuberculosis", Antimicrob Agents Chemother, 4: 94-104.

Holland et al., "PCR Detection of *Escherichia coli* 0157:H7 Directly from Stools", J. Clin. Microbiol., 2000, 38(11): 4108-4113.

Holz et al. (2001) "Freezing of homogenized sputum samples for intermittent storage", Clin Exp Allergy, 31: 1328-1331.

Kent et al. (1985) "Public Health Microbiology, a Guide for the Level III Laboratory", Centers for Disease Control, Division of Laboratory Training and Consultation, Laboratory Program Office, 226 pages.

Kissane et al., "The fluorometric measurement of deoxyribonucleic acid in animal tissues with special reference to the central nervous system", J. Biol. Chem., 233: 184-188 (1958).

Krasnow et al. (1966) "Sputum digestion. I The mortality rate of tubercle bacilli in various digestion systems", Am J Clin Pathol., 45: 352-355.

Lehmann et al., "Real-Time PCR Analysis of DNA and RNA Extracted from Formalin-Fixed and Paraffin-Embedded Biopsies", Methods, vol. 25, No. 4, Jan. 1, 2001, pp. 409-418, XP003017515.

Lewis et al. (1997) "Stool form scale as a useful guide to intestinal transit time", Scandinavian Journal of Gastroenterology, 32: 920-924.

Lipsky et al. (1984) "Factors affecting clinical value of microscopy for acid-fast bacilli", Rev Infect Dis., 6:214-222.

Loktionov et al., "Quantitation of DNA from exfoliated colonocytes isolated from human stool surface as a novel noninvasive screening test for colorectal cancer", Clin Cancer Res., 1998, 4: 337-342.

Machiels et al., "New Protocol for DNA Extraction of Stool", Bio Techniques, 28: 286-290 (Feb. 2000).

McOrist et al., "A comparison of five methods for extraction of bacterial DNA from human faecal samples", Journal of Microbiological Methods (2002) 50: 131-139.

Moore et al., "Intestinal Floras of Populations That Have a High Risk of Colon Cancer", Applied and Environmental Microbiology, Sep. 1995, pp. 3202-3207.

Morello et al. (1969) "New medium for blood cultures", Appl. Microbiol., 17: 68-07.

Morris et al. (1995) "Molecular mechanisms of multidrug resistance in clinical isolates of Mycobacterium tuberculosis", J Infect Dis., 171: 954-960.

O'Sullivan, "Methods for Analysis of the Intestinal Microflora", Curt. Issues Intest. Microbiol. (2000), 1(2): 39-50.

Osbourne et al., "Sample preference for colorectal cancer screening tests: Blood or stool?", Open Journ. Preventative Medicine (2012) 2(3): 326-331.

Palladino et al., "Rapid Detection of vanA and vanB genes Directly from Clinical Specimens and Enrichment Broths by Real-Time Multiplex PCR Assay", J. Clin. Microbiol., Jun. 1, 2003, 41(6): 2483-2486.

Park et al. (2000) "Detection and identification of mycobacteria by amplification of the internal transcribed spacer regions with genus and species-specific PCR primers", J Clin Microbiol., 38: 4080-4085.

Parmasivan et al. (1983) "Effect of storage of sputum specimens at room temperature on smear and culture results", Tubercle, 64(2): 119-124.

Parsonnet, et al., "Helicobacter Pylori Infection and the Risk of Gastric Carcinoma", N Engl J Med, 1991, 325: 1127-1131.

Randerath et al., "Sequence analysis of nonradioactive RNA fragments by periodate-phosphatase digestion and chemical tritium labeling: characterization of large oligonucleotides and oligonucleotides containing modified nucleosides", Nucleic Acids Res, Sep. 1, 1974, pp. 1121-1142.

Richards, "Modifications of the diphenylamine reaction giving increased sensitivity and simplicity in the estimation of DNA", Analyt. Biochem., 57, 369-376 (1974).

Rossen et al., "Inhibition of PCR by components of food samples, microbial diagnostic assays and DNA-extraction solutions", International Journal of Food Microbiology (1992) 17: 37-45.

Rusconi et al., "Quantification of Sodium Dodecyl Sulfate in Microliter-Volume Biochemical Samples by Visible Light Spectroscopy", Analytical Biochemistry, 2001, 295: 31-37.

Ruzin (1999) "Buffers", Plant Microthechnique and Microscopy (1999).

Schmidt et al., "A method forthe determination of deoxyribonucleic acid, ribonucleic acid, and phosphoproteins in animal tissues", Journal of Biological Chemistry vol. 161, pp. 83-89 (1945).

Setlow, "Mechanisms which contribute to the long-term survival of spores of *Bacillus* species", Soc Appl Bacteriol Symp Ser.(1994) 23: 49S-60S, Suppl.

Sidransky et al., "Identification of ras oncogene mutations in the stool of patients with curable colorectal tumors", Science 256.n5053 (Apr. 3, 1992): pp. 102(4).

Silberberg, Chemistry, The Molecular Nature of Matter and Change, Mosby-Year Book Inc., USA, Chapter 2, pp. 73-75 (1996).

Sillen et al., "Stability Constants of Metal-Ion Complexes", Sep. 1965, J. Chem. Educ., vol. 42, No. 9, p. 521.

Silverstolpe (1948) "Improved Method for Detection of Tubercle Bacteria", Nordisk Medicin, 40(48): 2220-2222, Original Title: Förbättrad metod för påvisande av tuberkelbakterier.

Telenti et al. (1993) "Rapid identification of mycobacteria to the species level by polymerase chain reaction and enzyme analysis", J Clin Microbiol., 31:175-178.

Thornton et al. (1998) "Novel method for processing respiratory specimens for detection of mycobacteria by using C18-carboxypropylbetaine: Blinded study", J Clin Microbiol., 36(7): 1996-2003.

Van Der Giessen et al., "Amplification of 16S rRNA sequences to detect Mycobacterium Paratuberculosis", J. Med. Microbiol. (1992) vol. 36, pp. 255-263.

(56) References Cited

OTHER PUBLICATIONS

Van Der Hoek, et al. "Isolation of Human Immunodeficiency Virus Type 1 (HIV-1) RNA from Feces by a Simple Method and Difference between HIV-1 Subpopulations in Feces and Serum", Journal of Clinical Microbiology, Mar. 1995, pp. 581-588.
Weixian, "Analytical Chemistry Instruction Section and Study Guide (Part Two)", Beijing: Open University Press, 1963 pp. 281-282.
Weyant et al. (1990) Effect of ionic and nonionic detergents on the Taq polymerase. Biotechniques. Sep. 1990;9(3):308-9.
WHO Report (2001) "Global Tuberculosis Control", WHO/CDS/TB/2001, 173 pages.
Wilson (1996) "General principles of specimen collection and transport", Clin Inf Dis., 22: 766-777.
Xuan-Shen et al., "Reference Book for Ionic Equilibrium and Chemical Reactions in Aqueous Solutions", Reference Book for Higher Education, Higher Education Press, 1993, pp. 108-109.
Yan-Die, "Application of Coordination Chemistry in Industry", Reference Book for Higher Education, Higher Education Press, 1989 p. 12.
Yeager, Jr. et al. (1967) "Quantitative studies of mycobacterial populations in sputum and saliva", Am Rev Respir Dis, 95: 998-1004.
Ausubel et al., Purification and Concentration of DNA from Aqueous Solutions. Short Protocols in Molecular Biology, 5th ed. John Wiley & Sons, 2-6 (2002).
Birnboim (1971) "New Method for Extraction of Ribonucleic Acid and Polyribosomes from *Schizosaccharomyces pombe*," Journal of Bacteriology. 107(3):659-663.
Birnboim (1992) "Effect of Lipophilic Chelators on Oxyradical-Induced DNA Strand Breaks in Human Granulocytes: Paradoxical Effect of 1,1 O-Phenanthroline," Archives of Biochemistry and Biophysics. 294(1):17-21.
Birnboim (1992) "Extraction of High Molecular Weight RNA and DNA from Cultured Mammalian Cells," Methods in Enzymology. 216:154-160.
Birnboim et al. (1979) "A rapid alkaline extraction procedure for screening recombinant plasmid DNA," Nucleic Acids Research. 7(6):1513-1524.
Birnboim et al. (1981) "Fiuorometric Method for Rapid Detection of DNA Strand Breaks in Human White Blood Cells Produced by Low Doses of Radiation," Cancer Research. 41:1889-1892.
Buettner (1986) "Ascorbate Autoxidation in the Presence of Iron and Copper Chelates," Free Radical Research Communications, Free Radical Research Communications. 1:349-353.
Buettner (1988) "In the absence of catalytic metals ascorbate does not autoxidize at pH 7: ascorbate as a test for catalytic metals," Journal of Biochemical and Biophysical Methods. 16:27-40.
Buettner (1990) "Ascorbate oxidation: UV absorbance of ascorbate and ESR spectroscopy of the ascorbyl radical as assays for iron," Free Radical Research Communications. 10:5-9.
Buettner et al. (1996) "Catalytic Metals, Ascorbate and Free Radicals: Combinations to Avoid," Radiation Research. 145:532-541.
Clarke et al. (1991) "Stabilities of the alkaline earth and divalent transition metal complexes of the tetraazamacrocyclic tetraacetic acid ligands," Inorganic Chimica Acta. 190:27-36.
Croxson et al. (1981) "Extraction of Rotavirus from Human Feces by Treatment with Lithium Dodecyl Sulfate," Applied and Environmental Microbiology. 41(1):255-260.
Dawson et al. (1989) "Stability constants of metal complexes," Ch. 17 In; Data for Biochemical Research, Third Edition, Oxford Science Publications, pp. 399-407.
European Office Action corresponding to European Patent Application No. 03729743, dated Oct. 1, 2007.
Garcia-Closas et al. (2001) "Collection of Genomic DNA from Adults in Epidemiological Studies by Buccal Cytobrush and Mouthwash," Cancer Epidemiology, Biomarkers & Prevention. 10:687-696.

Goldenberger et al., "Simple 'universal' DNA extraction procedure compatible with direct PCR amplification," Experientia. 52:295 (1996) (Abstract Only).
Grant et al. "Elimination of non-viable 6-thioguanine-sensitive T cells from viable T cells prior to PCR analysis," J Immunol Methods. 225(1-2):61-66 (1999).
Heath et al. (2001) "Use of Buccal Cells Collected in Mouthwash as a Source of DNA for Clinical Testing," Arch. Pathol. Lab. Med. 125:127-133.
International Preliminary Report corresponding to International Patent Application No. PCT/CA2007/001785, dated Jan. 19, 2009.
International Search Report corresponding to International Patent Application No. PCT/CA03/00869, dated Mar. 30, 2004.
International Search Report with Written Opinion corresponding to International Patent Application No. PCT/CA2007/001785, dated Jan. 21, 2008.
Kilpatrick, "Noncryogenic preservation of mammalian tissues for DNA extraction: an assessment of storage methods," Biochem Genet. 40(1-2):53-62 (2002).
Loens et al. (2002) "Detection of Mycoplasma pneumoniae in Spiked Clinical Samples by Nucleic Acid Sequence-Based Amplification," Journal of Clinical Microbiology. 40(4):1339-1345.
Longmire et al., "Use of 'Lysis Buffer' in DNA isolation and its implication for museum collections," Occasional Papers, Museum of Texas Tech University. 163:1-3 (1997).
Lum (1998) "A Simple Mouthwash Method for Obtaining Genomic DNA in Molecular Epidemiological Studies," Cancer Epidemiology, Biomarkers & Prevention. 7:719-724.
Meulenbelt, I. et al. "High-Yield Noninvasive Human Genomic DNA Isolation Method for Genetic Studies in Geographically Dispersed Families and Populations" American Journal of Human Genetics, 1995, vol. 57, No. 1252-1254, 3 pages.
Miller et al. "Transition metals as catalysts of 'autoxidation' reactions," Free Radic Biol Med. 8(1):95-108 (1990).
Offner et al., "Heterogeneity of high-molecular-weight human salivary mucins," Adv Dent Res. 14:69-75 (2000).
Pershadsingh et al. (1980) "A High Affinity Calcium-stimulated Magnesium-dependent Adenosine Triphosphatase in Rat Adipocyte Plasma Membranes," The Journal of Biological Chemistry. 255(9):4087-4093.
Rahman et al. (2004) "Chromatography Paper Strip Method for Collection, Transportation, and Storage of Rotavirus RNA in Stool Samples," Journal of Clinical Microbiology. 42(4):1605-1608.
Response to the Written Opinion corresponding to International Patent Application No. PCT/CA2003/000869, dated Jun. 3, 2004.
Rymaszewski et al. (1990) "Estimation of Cellular DNA Content in Cell Lysates Suitable for RNA Isolation," Analytical Biochemistry. 188:91-96.
Schmitteckert et al., "DNA detection in hair of transgenic mice-a simple technique minimizing the distress on the animals," Lab Anim. 33(4):385-9 (1999).
Seregni et al. "Structure, function, and gene expression of epithelial mucins," Tumori. 83(3):625-32 (1997).
Smith et al. (2003) "Potent Inhibition of Ribonuclease A by Oligo(vinylsulfonic Acid)," Journal of Biological Chemistry. 278:20934-20938.
Terasaki et al. (1998) "Saliva as DNA Source for HLA Typing," Human Immunology. 59:597-598.
Van Schie et al. (1997) "Saliva: a convenient source of DNA for analysis of bi-allelic polymorph isms of Fcg receptor I IA (CD32) and Fcg receptor IIIB (CD16)," Journal of Immunological Methods. 208:91-101.
Wollants et al. (2004) "Evaluation of a norovirus sampling method using sodium dodecyl sulfate/EDT A-pretreated chromatography paper strips," Journal of Virological Methods. 122:45-48.
Written Opinion corresponding to International Patent Application No. PCT/CA2003/000869, dated Apr. 5, 2004.
Exhibit 1 of Declaration of Brian M. Kramer in Support of DNA Genotek Inc.'s Opposition to Defendants' "Unopposed" Motion for Leave to File Surreply and DNA Genotek Inc.'s Motion to Strike Unauthorized Expert Declaration, filed Nov. 20, 2015: a true and correct email chain between attorneys for Spectrum and attorneys for DNA Genotek, with dates ranging from Nov. 17, 2015, to Nov.

(56) References Cited

OTHER PUBLICATIONS 18, 2015, bearing the subject line "Re: *DNA Genotek v.Spectrum*; Case No. 15-CV-00661-SLR." (4 pages).
Exhibit 1 of Declaration of DeForest McDuff, Ph.D., dated and filed Aug. 24, 2015: Curriculum vitae of DeForest McDuff, Ph.D., filed Aug. 24, 2015 (12 pages).
Exhibit 1 of Declaration of John M. Collins in Support of DNA Genotek's Reply in Support of the Motion for Preliminary Injunction, filed Novembers, 2015: Curriculum vitae of John M. Collins, Ph.D., filed Nov. 5, 2015 (5 pages).
Exhibit 1 of Redacted Declaration of Brian M. Kramer in Support of Plaintiff DNA Genotek Inc.'s Reply Brief in Support of Its Motion for Preliminary Injunction, filed Nov. 11, 2015: a true and correct excerpted pages from the deposition of Terry Layton, dated Oct. 14, 2015 (40 pages).
Exhibit 1 of Redacted Public Version of the Declaration of Brian M. Kramer in Support of DNA Genotek Inc.'s Answering Brief in Response to Defendant's Motion to Dismiss, filed Oct. 7, 2015: a true and correct excerpted pages from the deposition of Gregg Williams, taken on Sep. 22, 2015 Redacted Version in Its Entirety (2 pages).
Exhibit 1 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: a true and correct WO 2015/017701, published on Feb. 5, 2015 (23 pages).
Exhibit 1 of Redacted Public Version of the Declaration of Melanie L. Mayer in Support of Defendants' Reply Brief in Support of Motion to Dismiss DNA Genotek's Complaint for Lack of Personal Jurisdiction, dated Oct. 16, 2015, filed Oct. 26, 2015: a true and correct compilation of web pages retrieved from the website http://dna. ancestry.com/that were printed Oct. 15, 2015 (4 pages).
Exhibit 10 of Declaration of John M. Collins in Support of DNA Genotek's Reply in Support of the Motion for Preliminary Injunction, filed Nov. 5, 2015: Reply to Office Action for U.S. Appl. No. 12/096,767, dated Feb. 2, 2012 (7 pages).
Exhibit 10 of Redacted Public Version of the Declaration of Brian M. Kramer in Support of DNA Genotek Inc.'s Answering Brief in Response to Defendant's Motion to Dismiss, filed Oct. 7, 2015: are true and correct documents produced by Spectrum, bearing Bates Nos. SPEC00000035, SPEC00000043, SPEC00000053, and SPEC00000067, filed Oct. 7, 2015 Redacted Version in Its Entirety (2 pages).
Exhibit 1001 of Resubmitted Petition for Inter Partes Review of U.S. Pat. No. 8,221,381, Inter Partes Review No. IPR 2016-00060, dated Nov. 5, 2015: U.S. Pat. No. 8,221,381 (Muir et al.) (25 pages).
Exhibit 1002 of Resubmitted Petition for Inter Partes Review of U.S. Pat. No. 8,221,381, Inter Partes Review No. IPR 2016-00060, dated Nov. 5, 2015: File History of U.S. Pat. No. 8,221,381 (401 pages).
Exhibit 1003 of Resubmitted Petition for Inter Partes Review of U.S. Pat. No. 8,221,381, Inter Partes Review No. IPR 2016-00060, dated Nov. 5, 2015: Declaration of Terry N. Layton, Ph.D. (130 pages).
Exhibit 1004 of Resubmitted Petition for Inter Partes Review of U.S. Pat. No. 8,221,381, Inter Partes Review No. IPR 2016-00060, dated Nov. 5, 2015: Curriculum Vitae of Terry N. Layton, Ph.D. (4 pages).
Exhibit 1005 of Resubmitted Petition for Inter Partes Review of U.S. Pat. No. 8,221,381, Inter Partes Review No. IPR 2016-00060, dated Nov. 5, 2015: Plaintiff DNA Genotek Inc.'s Opening Brief in Support of Motion for Preliminary Injunction, *DNA Genotek, Inc.* v. *Spectrum DNA; Spectrum Solutions L.L.C., and Spectrum Packaging, LLC*, Case No. 15-CV-00661-SLR, dated Aug. 24, 2015 (26 pages).
Exhibit 1006 of Resubmitted Petition for Inter Partes Review of U.S. Pat. No. 8,221,381, Inter Partes Review No. IPR 2016-00060, dated Nov. 5, 2015: Declaration of Juan C. Lasheras, Ph.D., *DNA Genotek, Inc.* v. *Spectrum DNA; Spectrum Solutions L.L.C., and Spectrum Packaging, LLC*, Case No. 15-cv-00661-SLR, dated Aug. 24, 2015 (15 pages).
Exhibit 1007 of Resubmitted Petition for Inter Partes Review of U.S. Pat. No. 8,221,381, Inter Partes Review No. IPR 2016-00060, dated Nov. 5, 2015: U.S. Pat. No. 7,645,424 (O'Donovan) (8 pages).
Exhibit 1008 of Resubmitted Petition for Inter Partes Review of U.S. Pat. No. 8,221,381, Inter Partes Review No. IPR 2016-00060, dated Nov. 5, 2015: WO-2003/104251-A2 (DNA Genotek Inc) (50 pages).
Exhibit 1009 of Resubmitted Petition for Inter Partes Review of U.S. Pat. No. 8,221,381, Inter Partes Review No. IPR 2016-00060, dated Nov. 5, 2015: U.S. Pat. No. 6,152,296 (Shih) (9 pages).
Exhibit 1010 of Resubmitted Petition for Inter Partes Review of U.S. Pat. No. 8,221,381, Inter Partes Review No. IPR 2016-00060, dated Nov. 5, 2015: WO-98/03265-A1 (Kyoritsu Chemical-check Lab., Corp) (64 pages).
Exhibit 1011 of Resubmitted Petition for Inter Partes Review of U.S. Pat. No. 8,221,381, Inter Partes Review No. IPR 2016-00060, dated Nov. 5, 2015: (Certified English Translation) WO- 98/03265-A1 (Kyoritsu Chemical-check Lab., Corp) (30 pages).
Exhibit 1012 of Resubmitted Petition for Inter Partes Review of U.S. Pat. No. 8,221,381, Inter Partes Review No. IPR 2016-00060, dated Nov. 5, 2015: DE-199 50 884-A1 (Wella Ag) (16 pages).
Exhibit 1013 of Resubmitted Petition for Inter Partes Review of U.S. Pat. No. 8,221,381, Inter Partes Review No. IPR 2016-00060, dated Nov. 5, 2015: (Certified English Translation) DE- 199 50884-A1 (Wella Ag) (8 pages).
Exhibit 1014 of Resubmitted Petition for Inter Partes Review of U.S. Pat. No. 8,221,381, Inter Partes Review No. IPR 2016-00060, dated Nov. 5, 2015: U.S. Pat. No. 6,228,323 (Asgharian et al.) (23 pages).
Exhibit 1015 of Resubmitted Petition for Inter Partes Review of U.S. Pat. No. 8,221,381, Inter Partes Review No. IPR 2016-00060, dated Nov. 5, 2015: The American Heritage Dictionary of the English Language, Fourth Edition (2000) (definitions of: "corner"; "fastener"; "inert"; "reservoir"; "vial") (8 pages).
Exhibit 1016: Defendants' Brief in Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-CV-00661-SLR, dated Oct. 2, 2015 (37 pages).
Exhibit 1017 of Resubmitted Petition for Inter Partes Review of U.S. Pat. No. 8,221,381, Inter Partes Review No. IPR 2016-00060, dated Nov. 5, 2015: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cV-00661-SLR, dated Oct. 2, 2015 (38 pages).
Exhibit 1018 of Resubmitted Petition for Inter Partes Review of U.S. Pat. No. 8,221,381, Inter Partes Review No. IPR 2016-00060, dated Nov. 5, 2015: U.S. Appl. No. 60/523,104, filed Nov. 19, 2003 by Michael O'Donovan (9 pages).
Exhibit 1019 of Resubmitted Petition for Inter Partes Review of U.S. Pat. No. 8,221,381, Inter Partes Review No. IPR 2016-00060, dated Nov. 5, 2015: Numerical Designation of U.S. Pat. No. 8,221,381 Claim Element or Limitation, dated Nov. 5, 2015 (4 pages).
Exhibit 11 of Declaration of John M. Collins in Support of DNA Genotek's Reply in Support of the Motion for Preliminary Injunction, dated Nov. 5, 2015, filed Nov. 5, 2015: Notice of Allowability for U.S. Appl. No. 12/096,767, dated Apr. 1, 2012 (4 pages).
Exhibit 11 of Redacted Public Version of the Declaration of Brian M. Kramer in Support of DNA Genotek Inc.'s Answering Brief in Response to Defendant's Motion to Dismiss, filed Oct. 7, 2015: a true and correct document retrieved from the Delaware Division of Corporations showing Ancestry.com Dna, LLC is a Delaware corporation, filed Oct. 7, 2015 (2 pages).
Exhibit 2 of Declaration of Brian M. Kramer in Support of DNA Genotek Inc.'s Opposition to Defendants' "Unopposed" Motion for Leave to File Surreply and DNA Genotek Inc.'s Motion to Strike Unauthorized Expert Declaration, filed Nov. 20, 2015: a true and correct email chain between attorneys for Spectrum and attorneys

(56) References Cited

OTHER PUBLICATIONS for DNA Genotek, dated Nov. 19, 2015, bearing the subject line "RE: PAC-#1209828-v1 Draft Unopposed motion for leave to file surreplv.DOCX." (2 pages).
Exhibit 2 of Declaration of DeForest McDuff, Ph.D., dated and filed Aug. 24, 2015: Spectrum Website, Who We Are, http://www.spectrum-dna.com/about-us/, filed Aug. 24, 2015 (5 pages).
Exhibit 2 of Declaration of John M. Collins in Support of DNA Genotek's Reply in Support of the Motion for Preliminary Injunction, filed Nov. 5, 2015: U.S. Pat. No. 8,221,381 82, Jul. 17, 2012 (26 pages).
Exhibit 2 of Redacted Declaration of Brian M. Kramer in Support of Plaintiff DNA Genotek Inc.'s Reply Brief in Support of Its Motion for Preliminary Injunction, filed Nov. 11, 2015: a true and correct excerpted pages from the deposition of Thomas R. Varner, dated Oct. 14, 2015 (20 pages).
Exhibit 2 of Redacted Public Version of the Declaration of Brian M. Kramer in Support of DNA Genotek Inc.'s Answering Brief in Response to Defendant's Motion to Dismiss, filed Oct. 7, 2015: a true and correct compilation of web pages retrieved from Spectrum DNA website, http://www.spectrum-dna.com/, filed Oct. 7, 2015 (3 pages).
Exhibit 2 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: a true and correct list of the PTO's publicly-searchable assignment database to determine the number of U.S. patent and U.S. published patent applications currently assigned to the defendant in this case, Ancestry.com DNA, LLC, filed Sep. 14, 2015 (29 pages).
Exhibit 2 of Redacted Public Version of the Declaration of Melanie L. Mayer in Support of Defendants' Reply Brief in Support of Motion to Dismiss DNA Genotek's Complaint for Lack of Personal Jurisdiction, dated Oct. 16, 2015, filed Oct. 26, 2015: a true and correct fully executed Manufacturing Agreement between Spectrum Packaging, L.L.C, and Ancestry.com DNA, LLC, which was produced by Spectrum in this action with Bates Nos. SPEC00000015-34, filed Oct. 26, 2015 Redacted Version in Its Entirety (2 pages).
Exhibits of Declaration of DeForest McDuff, Ph.D., dated and filed Aug. 24, 2015: Spectrum Website, Saliva DNA Collection Device, httg://www.sgectrum-dna.com/saliva-dnacollectiondevice/, filed Aug. 24, 2015 (4 pages).
Exhibit 3 of Declaration of John M. Collins in Support of DNA Genotek's Reply in Support of the Motion for Preliminary Injunction, filed Nov. 5, 2015: U.S. Pat. No. 7,645,424 B2, Jan. 12, 2010 (9 pages).
Exhibit 3 of Redacted Declaration of Brian M. Kramer in Support of Plaintiff DNA Genotek Inc.'s Reply Brief in Support of Its Motion for Preliminary Injunction, filed Nov. 11, 2015: a true and correct excerpted pages from the deposition of Ian Curry, dated Sep. 4, 2015 (6 pages).
Exhibit 3 of Redacted Public Version of the Declaration of Brian M. Kramer in Support of DNA Genotek Inc.'s Answering Brief in Response to Defendant's Motion to Dismiss, filed Oct. 7, 2015: a true and correct excerpt pages from the Court's Hearing Transcript, dated Sep. 10, 2015 (3 pages).
Exhibit 3 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: a true and correct Product Design—Customization Requirements Documents between Ancestry and DNA Genotek, dated Feb. 13, 2012, and signed by Mr. Ken Chahine (8 pages).
Exhibit 3 of Redacted Public Version of the Declaration of Melanie L. Mayer in Support of Defendants' Reply Brief in Support of Motion to Dismiss DNA Genotek's Complaint for Lack of Personal Jurisdiction, dated Oct. 16, 2015, filed Oct. 26, 2015: a true and correct fully executed Amendment to the Manufacturing Agreement between Ancestry.com DNA, LLC and Spectrum Packaging, L.L.C., which was produced by Spectrum in this action with Bates Nos. SPEC0000000?-14, filed Oct. 26, 2015 Redacted Version in Its Entirety (2 pages).

Exhibit 3: a true and correct file attached to the e-mail appearing as Exhibit 2, which bears the file name "MoFo edits Draft_Unopposed_motion_for_leave_to_file_surreply (2).docx.", filed Nov. 20, 2015 (3 pages).
Exhibit 4 of Declaration of DeForest McDuff, Ph.D., dated and filed Aug. 24, 2015: Spectrum, Marketing Sheet, http://spectrum-dna.com/wg-content/ugloads/2015/08/Marketing-Sheet-for-Saliva-Kit.pdf, filed Aug. 24, 2015 (2 pages).
Exhibit 4 of Declaration of John M. Collins in Support of DNA Genotek's Reply in Support of the Motion for Preliminary Injunction, filed Nov. 5, 2015: English translation of WO 98/03265, published Jan. 29, 1998 (30 pages).
Exhibit 4 of Redacted Declaration of Brian M. Kramer in Support of Plaintiff DNA Genotek Inc.'s Reply Brief in Support of Its Motion for Preliminary Injunction, filed Nov. 11, 2015: a true and correct Deposition Exhibit DX-4 to the deposition of Ian Curry, dated Sep. 4, 2015, Redacted Version in Its Entirety (2 pages).
Exhibit 4 of Redacted Public Version of the Declaration of Brian M. Kramer in Support of DNA Genotek Inc.'s Answering Brief in Response to Defendant's Motion to Dismiss, filed Oct. 7, 2015: a true and Ancestry.com's webpage Delaware Genealogy & Delaware Family History Resources, http://search.ancestry.com/Places/US/Delaware/, filed on Oct. 7, 2015 (3 pages).
Exhibit 4 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: US 2009/0216213, Aug. 27, 2009 (25 pages).
Exhibit 4 of Redacted Public Version of the Declaration of Melanie L. Mayer in Support of Defendants' Reply Brief in Support of Motion to Dismiss DNA Genotek's Complaint for Lack of Personal Jurisdiction, dated Oct. 16, 2015, filed Oct. 26, 2015: a true and correct fully executed Purchase and Sales Commission Agreement between Ancestry.com DNA, LLC and Spectrum Packaging, L.L.C., which was produced by Spectrum in this action with Bates Nos. SPEC00000097-109, filed Oct. 26, 2015 Redacted Version in Its Entirety (2 pages).
Exhibit 5 of Declaration of DeForest McDuff, Ph.D., dated and filed Aug. 24, 2015: Spectrum Website, Custom Packaging, http://www.spectrum-dna.com/custom-gackaging/, filed Aug. 24, 2015 (9 pages).
Exhibit 5 of Declaration of John M. Collins in Support of DNA Genotek's Reply in Support of the Motion for Preliminary Injunction, filed Nov. 5, 2015: U.S. Pat. No. 7,537, 132 82, May 26, 2009 (6 pages).
Exhibit 5 of Redacted Declaration of Brian M. Kramer in Support of Plaintiff DNA Genotek Inc.'s Reply Brief in Support of Its Motion for Preliminary Injunction, filed Nov. 11, 2015: a true and excerpted pages from the deposition of DeForest McDuff, dated Sep. 10, 2015 (8 pages).
Exhibit 5 of Redacted Public Version of the Declaration of Brian M. Kramer in Support of DNA Genotek Inc.'s Answering Brief in Response to Defendant's Motion to Dismiss, filed Oct. 7, 2015: a true and correct document titled, "Saliva DNA Collection," which was retrieved from http://www.spectrum-dna.com/saliva-dnacollection- device, filed Oct. 7, 2015 (3 pages).
Exhibit 5 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: a true and correct Product Design—Customization Requirements Documents between Ancestry and DNA Genotek, dated Sep. 20, 2012, and signed by Mr. Kenneth Chahine (9 pages).
Exhibit 5 of Redacted Public Version of the Declaration of Melanie L. Mayer in Support of Defendants' Reply Brief in Support of Motion to Dismiss DNA Genotek's Complaint for Lack of Personal Jurisdiction, dated Oct. 16, 2015, filed Oct. 26, 2015: a true and correct excerpts taken from the transcript of the deposition of Gregg Williams, which was taken on Sep. 22, 2015, filed Oct. 26, 2015 Redacted Version in Its Entirety (2 pages).
Exhibit 6 of Declaration of DeForest McDuff, Ph.D., dated and filed Aug. 24, 2015: Spectrum, Clinical Data Sheet, http://spectrum-dna.com/wg-content/ugloads/2015/06/Sgectrum-Clinical-Data-Sheet.pdf, filed Aug. 24, 2015 (2 pages).
Exhibit 6 of Declaration of John M. Collins in Support of DNA Genotek's Reply in Support of the Motion for Preliminary Injunc-

(56) References Cited

OTHER PUBLICATIONS tion, filed Nov. 5, 2015: substitute pp. 1 and 22 for WO 2007/068094 (PCT/CA2006/002009), filed with Declaration on Nov. 5, 2015 (3 pages).
Exhibit 6 of Redacted Public Version of the Declaration of Brian M. Kramer in Support of DNA Genotek Inc.'s Answering Brief in Response to Defendant's Motion to Dismiss, filed Oct. 7, 2015: a true and correct document titled, "Saliva Kit for DNA Collection," which was retrieved from http://www.spectrum-dna.com/wpcontent/uploads/2015/09/Spectrum-Clinical-Data-Sheet.pdf, filed Oct. 7, 2015 (2 pages).
Exhibit 6 of Redacted Public Version of the Declaration of Brian M. Kramer in Support of Plaintiff DNA Genotek Inc.'s Opposition to Ancestry.com DNA, LLC's Motion to Dismiss, filed Sep. 14, 2015: a true and correct DNA Genotek's legal notice, filed Sep. 14, 2015 (3 pages).
Exhibit 7 of Declaration of DeForest McDuff, Ph.D., dated and filed Aug. 24, 2015: Saliva Collection Instructions, http://spectrum-dna.com/wgcontent/uploads/2015/06/Saliva-CollectionInstructions.pdf, filed Aug. 24, 2015 (2 pages).
Exhibit 7 of Declaration of John M. Collins in Support of DNA Genotek's Reply in Support of the Motion for Preliminary Injunction, filed Nov. 5, 2015: Preliminary Amendment for U.S. Appl. No. 12/096,767, dated Jun. 9, 2008 (4 pages).
Exhibit 7 of Redacted Public Version of the Declaration of Brian M. Kramer in Support of DNA Genotek Inc.'s Answering Brief in Response to Defendant's Motion to Dismiss, filed Oct. 7, 2015: a true and correct document produced by Spectrum, bearing Bates Nos. SPEC00000015- SPEC00000034, filed Oct. 7, 2015 Redacted Version in Its Entirety (2 pages).
Exhibit 7 of Redacted Public Version of the Declaration of Brian M. Kramer in Support of Plaintiff DNA Genotek Inc.'s Opposition to Ancestry.com DNA, LLC's Motion to Dismiss, dated Sep. 3, 2015, filed Sep. 14, 2015: a true and correct Written Opinion of the International Searching Authority for PCT patent application publication WO 2015/017701 A 1, dated Nov. 14, 2014 (8 pages).
Exhibit 8 of Declaration of John M. Collins in Support of DNA Genotek's Reply in Support of the Motion for Preliminary Injunction, filed Nov. 5, 2015: Non-Final Office Action for U.S. Appl. No. 12/096,767, dated Dec. 27, 2011 (8 pages).
Exhibit 8 of Redacted Public Version of the Declaration of Brian M. Kramer in Support of DNA Genotek Inc.'s Answering Brief in Response to Defendant's Motion to Dismiss, filed Oct. 7, 2015: a true and correct document produced by Spectrum, bearing Bates No. SPEC00000007-SPEC00000014, filed Oct. 7, 2015 Redacted Version in Its Entirety (2 pages).
Exhibit 9 of Declaration of John M. Collins in Support of DNA Genotek's Reply in Support of the Motion for Preliminary Injunction, filed Nov. 5, 2015: EP 0273015 A2, published Jun. 29, 1988 (9 pages).
Exhibit 9 of Redacted Public Version of the Declaration of Brian M. Kramer in Support of DNA Genotek Inc.'s Answering Brief in Response to Defendant's Motion to Dismiss, filed Oct. 7, 2015: a true and correct document produced by Spectrum, bearing Bates No. SPEC00000097-SPEC0000109, filed Oct. 7, 2015 Redacted Version in Its Entirety (2 pages).
Exhibit A of Complaint, dated Jul. 30, 2015: U.S. Pat. No. 8,221,381 B2, Jul. 17, 2012 (26 pages).
Exhibit A of Complaint, dated May 4, 2015: U.S. Pat. No. 8,221,381 B2, Jul. 17, 2012 (26 pages).
Exhibit A of Declaration of Brian M. Kramer in Support of Motion for Preliminary Injunction, filed Aug. 24, 2015: Aug. 12, 2005 Articles of Incorporation of Spectrum Packaging L.L.C. (2 pages).
Exhibit A of Declaration of Ian Curry, dated and filed Aug. 24, 2015: User Instruction for DNA Genotek's Oraaene•RNA® !RE-100), filed Aug. 24, 2015 (3 pages).
Exhibit A of Declaration of Juan C. Lasheras, Ph.D., dated and filed on Aug. 24, 2015: Curriculum vitae of Juan C. Lasheras, Ph.D., filed Aug. 24, 2015 (36 pages).

Exhibit A of Declaration of Terry Layton, Ph.D. in Support of Defendants' Opposition to DNA Genotek's Motion for Preliminary Injunction, dated Oct. 2, 2015, filed Oct. 2, 2015: Curriculum vitae of Terry Layton, Ph.D., filed Oct. 2, 2015 (9 pages).
Exhibit A of Defendants' Unopposed Motion for Leave to File a Surreply in Further Opposition to Plaintiffs Motion for a Preliminary Injunction, filed Nov. 19, 2015: Surreply in Support of Defendants' Brief in Opposition to DNA Genotek's Motion for Preliminary Injunction, filed Nov. 19, 2015 (12 pages).
Exhibit A of Exhibit 1006 of Resubmitted Petition for Inter Partes Review of U.S. Pat. No. 8,221,381, Inter Partes Review No. I PR 2016-00060, dated Nov. 5, 2015: Declaration of Juan C. Lasheras, Ph.D., *DNA Genotek, Inc.* v. *Spectrum DNA; Spectrum Solutions L.L.C., and Spectrum Packaging, LLC*, Case No. 15-cv-00661-SLR, dated Aug. 24, 2015: Curriculum vitae of Juan C. Lasheras, Ph.D., filed Aug. 24, 2015 (36 pages).
Exhibit A of Exhibit 1017 of Resubmitted Petition for Inter Partes Review of U.S. Pat. No. 8,221,381, Inter Partes Review No. IPR 2016-00060, dated Nov. 5, 2015: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Oct. 2, 2015: Curriculum vitae of Terry Layton, Ph.D., filed Oct. 2, 2015 (9 pages).
Exhibit A of First Amended Complaint, dated Jul. 24, 2015: U.S. Pat. No. 8,221,381 B2, Jul. 17, 2012 (26 pages).
Exhibit A of Redacted Public Version of the Declaration of Melanie L. Mayer in Support of Defendants' Brief in Opposition to DNA Genotek's Motion for Preliminary Injunction, filed Oct. 9, 2015: a true and correct Reply to Office Action filed on Feb. 2, 2012 for U.S. Appl. No. 12/096,767, which issued as U.S. Pat. No. 8,221,381 (15 pages).
Exhibit B of Complaint, dated May 4, 2015: WO 2015/017701, Feb. 5, 2015 (22 pages).
Exhibit B of Declaration of Brian M. Kramer in Support of Motion for Preliminary Injunction, filed Aug. 24, 2015: Oct. 22, 2013 Articles of Amendment to Articles of Organization of Spectrum Packaging L.L.C. (2 pages).
Exhibit B of Declaration of Ian Curry, dated and filed Aug. 24, 2015: Spectrum Website, Custom Packaging, http://www.spectrum-dna.com/custom-Packaging/, filed Aug. 24, 2015 (9 pages).
Exhibit B of Declaration of Juan C. Lasheras, Ph.D., dated and filed on Aug. 24, 2015: U.S. Pat. No. 8,221,381 82, Jul. 17, 2012 (26 pages).
Exhibit B of Declaration of Terry Layton, Ph.D. in Support of Defendants' Opposition to DNA Genotek's Motion for Preliminary Injunction, filed Oct. 2, 2015: U.S. Pat. No. 8,221,381 B2, Jul. 17, 2012 (26 pages).
Exhibit B of Defendants' Unopposed Motion for Leave to File a Surreply in Further Opposition to Plaintiffs Motion for a Preliminary Injunction, filed Nov. 19, 2015: Declaration of Terry Layton, Ph.D. in Support of Defendants' Surreply in Support of Defendants' Brief in Opposition to DNA Genotek's Motion for Preliminary Injunction, filed Nov. 19, 2015 (16 pages).
Exhibit B of Exhibit 1006 of Resubmitted Petition for Inter Partes Review of U.S. Pat. No. 8,221,381, Inter Partes Review No. IPR 2016-00060, dated Nov. 5, 2015: Declaration of Juan C. Lasheras, Ph.D., *DNA Genotek, Inc.* v. *Spectrum DNA; Spectrum Solutions L.L.C., and Spectrum Packaging, LLC*, Case No. 15-cv-00661-SLR, dated Aug. 24, 2015: U.S. Pat. No. 8,221,381 B2, Jul. 17, 2012 (26 pages).
Exhibit B of Exhibit 1017 of Resubmitted Petition for Inter Partes Review of U.S. Pat. No. 8,221,381, Inter Partes Review No. I PR 2016-00060, dated Nov. 5, 2015: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Oct. 2, 2015: U.S. Pat. No. 8,221,381 82, Jul. 17, 2012 (26 pages).
Exhibit B of First Amended Complaint, dated Jul. 24, 2015: a true and correct WO 2015/017701 A1, Feb. 5, 2015 (22 pages).
Exhibit B of Redacted Public Version of the Declaration of Melanie L. Mayer in Support of Defendants' Brief in Opposition to DNA

(56) References Cited

OTHER PUBLICATIONS

Genotek's Motion for Preliminary Injunction, filed Oct. 9, 2015: a true and correct excerpts taken from the transcript of the deposition of Juan C. Lasheras, which was taken on Sep. 24, 2015 (40 pages).
Exhibit C of Declaration of Brian M. Kramer in Support of Motion for Preliminary Injunction, filed Aug. 24, 2015: May 6, 2015 Second Amended and Restated Articles of Organization of Spectrum Solutions L.L.C. (3 pages).
Exhibit C of Declaration of Juan C. Lasheras, Ph.D., dated and filed on Aug. 24, 2015: Spectrum Product Material Safety Data Sheet, filed Aug. 24, 2015 (11 pages).
Exhibit C of Declaration of Terry Layton, Ph.D. in Support of Defendants' Opposition to DNA Genotek's Motion for Preliminary Injunction, filed Oct. 2, 2015: Information sheet for the Spectrum Product, filed Oct. 2, 2015 (2 pages).
Exhibit C of Defendants' Unopposed Motion for Leave to File a Surreply in Further Opposition to Plaintiffs Motion for a Preliminary Injunction, filed Nov. 19, 2015: Declaration of Melanie L. Mayer in Support of Defendants' Surreply in Support of Defendants' Opposition to DNA Genotek's Motion for Preliminary Injunction, filed Nov. 19, 2015, including Exhibit 1: Transcript of the Deposition of John Collins, Ph.D.; San Dieqo, California; Friday, Nov. 13, 2015 (43 pages).
Exhibit C of Exhibit 1006 of Resubmitted Petition for Inter Partes Review of U.S. Pat. No. 8,221,381, Inter Partes Review No. I PR 2016-00060, dated Nov. 5, 2015: Declaration of Juan C. Lasheras, Ph.D., *DNA Genotek, Inc.* v. *Spectrum DNA; Spectrum Solutions L.L.C., and Spectrum Packaging, LLC*, Case No. 15-cv-00661-SLR, dated Aug. 24, 2015: Spectrum Product Material Safety Data Sheet, filed Aug. 24, 2015 (11 pages).
Exhibit C of Exhibit 1017 of Resubmitted Petition for Inter Partes Review of U.S. Pat. No. 8,221,381, Inter Partes Review No. I PR 2016-00060, dated Nov. 5, 2015: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Oct. 2, 2015: Information sheet for the Spectrum Product, filed Oct. 2, 2015 (2 pages).
Exhibit C of Redacted Public Version of the Declaration of Melanie L. Mayer in Support of Defendants' Brief in Opposition to DNA Genotek's Motion for Preliminary Injunction, filed Oct. 9, 2015: a true and correct exhibit DX12 used during the deposition of Juan C. Lasheras on Sep. 24, 2015 (2 pages).
Exhibit D of Declaration of Brian M. Kramer in Support of Motion for Preliminary Injunction, filed Aug. 24, 2015: the result of a "WHOIS" inquiry conducted through the Network Solution website at www.networksolutions.com on Aug. 23, 2015; the WHOIS database entry for spectrum-dna.com ("Spectrum DNA Site"), printed on Aug. 23, 2015 (5 pages).
Exhibit D of Declaration of Juan C. Lasheras, Ph.D., dated and filed on Aug. 24, 2015: Spectrum Product Marketing Sheet, filed Aug. 24, 2015 (2 pages).
Exhibit D of Declaration of Terry Layton, Ph.D. in Support of Defendants' Opposition to DNA Genotek's Motion for Preliminary Injunction, filed Oct. 2, 2015: Instruction for the Spectrum Product, filed Oct. 2, 2015 (2 pages).
Exhibit D of Exhibit 1006 of Resubmitted Petition for Inter Partes Review of U.S. Pat. No. 8,221,381, Inter Partes Review No. IPR 2016-00060, dated Nov. 5, 2015: Declaration of Juan C. Lasheras, Ph.D., *DNA Genotek, Inc.* v. *Spectrum DNA; Spectrum Solutions L.L.C., and Spectrum Packaging, LLC*, Case No. 15-cv-00661-SLR, dated Aug. 24, 2015: Spectrum Product Marketing Sheet, filed Aug. 24, 2015 (2 pages).
Exhibit D of Exhibit 1017 of Resubmitted Petition for Inter Partes Review of U.S. Pat. No. 8,221,381, Inter Partes Review No. I PR 2016-00060, dated Nov. 5, 2015: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Oct. 2, 2015: Instruction for the Spectrum Product, filed Oct. 2, 2015 (2 pages).
Exhibit D of Redacted Public Version of the Declaration of Melanie L. Mayer in Support of Defendants' Brief in Opposition to DNA Genotek's Motion for Preliminary Injunction, filed Oct. 9, 2015: a true and correct exhibit DX13 used during the deposition of Juan C. Lasheras on Sep. 24, 2015 (2 pages).
Exhibit E of Declaration of Brian M. Kramer in Support of Motion for Preliminary Injunction, filed Aug. 24, 2015: a printout of the Spectrum DNA site printed on Jul. 29, 2015 (4 pages).
Exhibit E of Declaration of Juan C. Lasheras, Ph.D., dated and filed on Aug. 24, 2015: Spectrum Product Instructions for Use, filed Aug. 24, 2015 (2 pages).
Exhibit E of Declaration of Terry Layton, Ph.D. in Support of Defendants' Opposition to DNA Genotek's Motion for Preliminary Injunction, filed Oct. 2, 2015: Select pages from Webster's Third New International Dictionary of the English Language Unabridged, Merriam-Webster Inc., Publishers. Sprinqfield, Massachusetts, USA, 1993, filed Oct. 2, 2015 (5 pages).
Exhibit E of Exhibit 1006 of Resubmitted Petition for Inter Partes Review of U.S. Pat. No. 8,221,381, Inter Partes Review No. I PR 2016-00060, dated Nov. 5, 2015: Declaration of Juan C. Lasheras, Ph.D., *DNA Genotek, Inc.* v. *Spectrum DNA; Spectrum Solutions L.L.C., and Spectrum Packaging, LLC*, Case No. 15-cV-00661-SLR, dated Aug. 24, 2015: Spectrum Product Instructions for Use, filed Aug. 24, 2015 (2 pages).
Exhibit E of Exhibit 1017 of Resubmitted Petition for Inter Partes Review of U.S. Pat. No. 8,221,381, Inter Partes Review No. I PR 2016-00060, dated Nov. 5, 2015: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Oct. 2, 2015: Select pages from Webster's Third New International Dictionary of the English Language Unabridged, Merriam-Webster Inc.
Exhibit E of Redacted Public Version of the Declaration of Melanie L. Mayer in Support of Defendants' Brief in Opposition to DNA Genotek's Motion for Preliminary Injunction, filed Oct. 9, 2015: a true and correct excerpts taken from the transcript of the deposition of Ian Curry, which was taken on Sep. 4, 2015 Redacted Version in Its Entirety (2 pages).
Exhibit F of Declaration of Brian M. Kramer in Support of Motion for Preliminary Injunction, filed Aug. 24, 2015: a printout of the Spectrum DNA site printed on Aug. 7, 2015, depicting Spectrum's DNA collection device (3 pages).
Exhibit F of Declaration of Juan C. Lasheras, Ph.D., dated and filed on Aug. 24, 2015: Claim chart of Claim 1 of U.S. Pat. No. 8,221,381 in view of the Spectrum Device, filed Aug. 24, 2015 (12 pages).
Exhibit F of Declaration of Terry Layton, Ph.D. in Support of Defendants' Opposition to DNA Genotek's Motion for Preliminary Injunction, filed Oct. 2, 2015: U.S. Pat. No. 7,645,424 82, Jan. 12, 2010 (9 pages).
Exhibit F of Exhibit 1006 of Resubmitted Petition for Inter Partes Review of U.S. Pat. No. 8,221,381, Inter Partes Review No. I PR 2016-00060, dated Nov. 5, 2015: Declaration of Juan C. Lasheras, Ph.D., *DNA Genotek, Inc.* v. *Spectrum DNA; Spectrum Solutions L.L.C., and Spectrum Packaging, LLC*, Case No. 15-cv-00661-SLR, dated Aug. 24, 2015: Claim chart demonstrating the limitation of Claim 1 of U.S. Pat. No. 8,221,381 in view of the Spectrum Device, filed Aug. 24, 2015 (12 pages).
Exhibit F of Exhibit 1017 of Resubmitted Petition for Inter Partes Review of U.S. Pat. No. 8,221,381, Inter Partes Review No. I PR 2016-00060, dated Nov. 5, 2015: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-cv-00661-SLR, dated Oct. 2, 2015: U.S. Pat. No. 7,645,424 82, Jan. 12, 2010 (9 pages).
Exhibit F of Redacted Public Version of the Declaration of Melanie L. Mayer in Support of Defendants' Brief in Opposition to DNA Genotek's Motion for Preliminary Injunction, filed Oct. 9, 2015: a true and correct certified translation of International Patent Appli-

(56) References Cited

OTHER PUBLICATIONS cation PCT/JP97/02472 with an International Publication No. WO 98/03265, and a true and correct notarized translator's certification dated Sep. 21, 2015 (31 pages).
Exhibit G of Declaration of Brian M. Kramer in Support of Motion for Preliminary Injunction, filed Aug. 24, 2015: a WHOIS search result for the Spectrum Packaging Site conducted on Aug. 23, 2015 (5 pages).
Exhibit G of Declaration of Juan C. Lasheras, Ph.D., dated and filed on Aug. 24, 2015: WO 2015/017701, Feb. 5, 2015 (22 pages).
Exhibit G of Declaration of Terry Layton, Ph.D. in Support of Defendants' Opposition to DNA Genotek's Motion for Preliminary Injunction, filed Oct. 2, 2015: Claim chart comparing claim 1 of U.S. Pat. No. 8,221,381 82 to the disclosure of U.S. Pat. No. 7,645,424, filed Oct. 2, 2015 (13 pages).
Exhibit G of Exhibit 1006 of Resubmitted Petition for Inter Partes Review of U.S. Pat. No. 8,221,381, Inter Partes Review No. IPR 2016-00060, dated Nov. 5, 2015: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: WO 2015/017701 A1, Feb. 5, 2015 (22 pages).
Exhibit G of Exhibit 1017 of Resubmitted Petition for Inter Partes Review of U.S. Pat. No. 8,221,381, Inter Partes Review No. IPR 2016-00060, dated Nov. 5, 2015: Declaration of Terry Layton, Ph.D. in Support of Defendants' Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015: Claim chart comparing claim 1 of U.S. Pat. No. 8,221,381 82 to the disclosure of U.S. Pat. No. 7,645,424, filed Oct. 2, 2015 (13.
Exhibit G of Redacted Public Version of the Declaration of Melanie L. Mayer in Support of Defendants' Brief in Opposition to DNA Genotek's Motion for Preliminary Injunction, filed Oct. 9, 2015: a true and correct excerpts taken from the transcript of the deposition of DeForest McDuff, which was taken on Sep. 10, 2015 Redacted Version in Its Entirety (2 pages).
Exhibit H of Declaration of Brian M. Kramer in Support of Motion for Preliminary Injunction, filed Aug. 24, 2015: a WHOIS search result for the Spectrum Solutions Site conducted on Aug. 23, 2015 (5 pages).
Exhibit H of Declaration of Juan C. Lasheras, Ph.D., dated and filed on Aug. 24, 2015: file history of U.S. Appl. No. 61/861.329, filed Aug. 1, 2013 (28 pages).
Exhibit H of Declaration of Terry Layton, Ph.D. in Support of Defendants' Opposition to DNA Genotek's Motion for Preliminary Injunction, filed Oct. 2, 2015: English translation of WO 98/03265, published Jan. 29, 1998 (30 pages).
Exhibit H of Exhibit 1006 of Resubmitted Petition for Inter Partes Review of U.S. Pat. No. 8,221,381, Inter Partes Review No. IPR 2016-00060, dated Nov. 5, 2015: Declaration of Juan C. Lasheras, Ph.D., *DNA Genotek, Inc. v. Spectrum DNA; Spectrum Solutions L.L.C., and Spectrum Packaging, LLC*, Case No. 15-cV-00661-SLR, dated Aug. 24, 2015: file history of U.S. Appl. No. 61/861,329, filed Aug. 1, 2013 (28 pages).
Exhibit H of Exhibit 1017 of Resubmitted Petition for Inter Partes Review of U.S. Pat. No. 8,221,381, Inter Partes Review No. IPR 2016-00060, dated Nov. 5, 2015: Declaration of Terry Layton, Ph.D. in Support of Defendants' Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015: English translation of WO 98/03265, published Jan. 29, 1998 (30 pages).
Exhibit H of Redacted Public Version of the Declaration of Melanie L. Mayer in Support of Defendants' Brief in Opposition to DNA Genotek's Motion for Preliminary Injunction, filed Oct. 9, 2015: a true and correct OraSure Technologies, Inc.'s Form 10-Kforthe fiscal year ending Dec. 31, 2014, which was produced by DeForest McDuff in this action with Bates Nos. MCDUFF00000362-483 (123 pages).

Exhibit I of Declaration of Brian M. Kramer in Support of Motion for Preliminary Injunction, filed Aug. 24, 2015: a printout of the "About US" section on the Spectrum Solutions Site, which was printed on Aug. 23, 2015 (2 pages).
Exhibit I of Declaration of Terry Layton, Ph.D. in Support of Defendants' Opposition to DNA Genotek's Motion for Preliminary Injunction, filed Oct. 2, 2015: Claim chart comparing claim 1 of U.S. Pat. No. 8,221,381 B2 to the disclosure of WO 98/03265, filed Oct. 2, 2015 (14 pages).
Exhibit I of Exhibit 1017 of Resubmitted Petition for Inter Partes Review of U.S. Pat. No. 8,221,381, Inter Partes Review No. I PR 2016-00060, dated Nov. 5, 2015: Declaration of Terry Layton, Ph.D. in Support of Defendants' Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015: Claim chart comparing claim 1 of U.S. Pat. No. 8,221,381 82 to the disclosure of WO 98/03265, filed Oct. 2, 2015 (14 pages).
Exhibit I of Redacted Public Version of the Declaration of Melanie L. Mayer in Support of Defendants' Brief in Opposition to DNA Genotek's Motion for Preliminary Injunction, filed Oct. 9, 2015: a true and correct chapter entitled "Saliva Collection Devices and Diagnostic Platforms," authored by Paul Desmond Slowey, from the book entitled Advances in Salivary Diagnostics, published in 2015, and produced by DeForest McDuff in this action with Bates Nos. MCDUFF00000548-552 and MCDUFF00000593-621 (36 pages).
Exhibit J of Declaration of Brian M. Kramer in Support of Motion for Preliminary Injunction, filed Aug. 24, 2015: a LexisNexis® Accurint® report regarding Spectrum Packaging, filed Aug. 24, 2015 (5 pages).
Exhibit J of Declaration of Terry Layton, Ph.D. in Support of Defendants' Opposition to DNA Genotek's Motion for Preliminary Injunction, 2015, filed Oct. 2, 2015: WO 2015/017701, Feb. 5, 2015 (22 pages).
Exhibit J of Exhibit 1017 of Resubmitted Petition for Inter Partes Review of U.S. Pat. No. 8,221,381, Inter Partes Review No. I PR 2016-00060, dated Nov. 5, 2015: Declaration of Terry Layton, Ph.D. in Support of Defendants' Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015: WO 2015/017701, Feb. 5, 2015 (22 pages).
First Amended Complaint, dated Jul. 24, 2015 (14 pages).
Joint Motion to Terminate Proceeding pursuant to 35 U.S.C § 317(A), Inter Partes Review No. IPR 2016-01467, dated Feb. 1, 2017 (5 pages).
Joint Request that the Settlement Agreement Filed Separately as Exhibit 2008 be Treated as Business Confidential Information and be Kept Separate from the Files, Inter Partes Review No. IPR 2016-01467, dated Feb. 1, 2017 (4 pages).
Redacted Declaration of Brian M. Kramer in Support of Plaintiff DNA Genotek Inc.'s Reply Brief in Support of Its Motion for Preliminary Injunction, filed Nov. 11, 2015 (3 pages).
Redacted Plaintiff DNA Genotek Inc.'s Reply Brief in Support of Its Motion for Preliminary Injunction, filed Nov. 11, 2015 (27 pages).
Redacted Public Version of Ancestry.com DNA's Reply Brief in Support of Motion to Dismiss Genotek's Willful infringement, Conversion, Trespass to Chattel, and Action to Quiet Title Claims, filed Sep. 25, 2015 (15 pages).
Redacted Public Version of the Declaration of Brian M. Kramer in Support of DNA Genotek Inc.'s Answerinq Brief in Response to Defendant's Motion to Dismiss, filed Oct. 7, 2015 (4 pages).
Redacted Public Version of the Declaration of Brian M. Kramer in Support of Plaintiff DNA Genotek Inc.'s Opposition to Ancestry. com DNA, LLC's Motion to Dismiss, filed Sep. 14, 2015 (6 pages).
Redacted Public Version of the Declaration of Gregg Williams in Support of Defendants' Motion to Dismiss for Lack of Personal Jurisdiction, dated Sep. 3, 2015, filed Sep. 11, 2015 (4 pages).
Redacted Public Version of the Declaration of Gregg Williams in Support of Defendants' Opposition to DNA Genotek's Motion for Preliminary Injunction, filed Oct. 9, 2015 (3 pages).

(56) References Cited

OTHER PUBLICATIONS

Redacted Public Version of the Declaration of Melanie L. Mayer in Support of Defendants' Brief in Opposition to DNA Genotek's Motion for Preliminary Injunction, filed Oct. 9, 2015 (3 pages).
Redacted Public Version of the Declaration of Melanie L. Mayer in Support of Defendants' Reply Brief in Support of Motion to Dismiss DNA Genotek's Complaint for Lack of Personal Jurisdiction, filed Oct. 26, 2015 (3 pages).
Redacted Public Version of the Declaration of Thomas R. Varner, Ph.D. in Support of Defendants' Opposition to DNA Genotek's Motion for Preliminary Injunction, filed Oct. 9, 2015 (31 pages).
Redacted Public Version of the Defendant's Brief in Opposition to DNA Genotek's Motion for Preliminary Injunction, filed Oct. 9, 2015 (37 pages).
Redacted Public Version of the Defendants' Opening Brief in Support of Motion to Dismiss DNA Genotek's Complaint for Lack of Personal Jurisdiction, filed Sep. 11, 2015 (15 pages).
Redacted Public Version of the Defendants' Reply Brief in Support of Motion to Dismiss DNA Genotek's Complaint for Lack of Personal Jurisdiction, filed Oct. 26, 2015 (15 pages).
Redacted Public Version of the Plaintiff DNA Genotek Inc.'s Answering Brief in Response to Defendants' Motion to Dismiss filed Oct. 7, 2015 (25 pages).
Redacted Public Version of the Reply Declaration of Gregg Williams in Support of Defendants' Motion to Dismiss for Lack of Personal Jurisdiction, filed Oct. 26, 2015 (3 pages).
Termination of Proceeding pursuant to Settlement Prior to Institution 37 C.F.R. § 42.72, Inter Partes Review No. 2016-01467, dated Feb. 3, 2017 (3 pages).
Petitioner Ancestry.com DNA, LLC's Request for Rehearing and Reconsideration under 37 C.F.R. § 42.71 (d), Inter Partes Review No. IPR 2016-01152, dated Dec. 23, 2016 (19 pages).
Termination of Proceeding pursuant to Settlement After Institution 37 C.F.R. § 42.72, Inter Partes Review No. IPR 2016-00060, dated Feb. 3, 2017 (3 pages).
Granting Joint Motion to Terminate Proceeding and Dismissing Petitioner's Request for Rehearing and Reconsideration 37 C.F.R. § 42.72, Inter Partes Review No. IPR 2016-01152, dated Feb. 3, 2017 (3 pages).
Report on the Filing of Determination of an Action Regarding a Patent of Trademark for U.S. Pat. No. 8,221,381, dated May 4, 2015 (1 page).
Action for Patent Infringement for U.S. Pat. No. 8,221,381, dated Jul. 24, 2015 (64 pages).
Joint Request that the Settlement Agreement Filed Separately as Exhibit 2004 be Treated as Business Confidential Information and be Kept Separate from the Files, Inter Partes Review No. IPR 2016-01152, dated Feb. 1, 2017 (4 pages).
Petition for Inter Partes Review of U.S. Pat. No. 8,221,381, dated Oct. 20, 2015 (69 pages).
File History of U.S. Pat. No. 8,221,381, dated Oct. 20, 2015 (401 pages).
Declaration of Terry N. Layton, Ph.D., dated Oct. 20, 2015 (130 pages).
Curriculum Vitae of Terry N. Layton, Ph.D., dated Oct. 20, 2015 (4 pages).
Plaintiff DNA Genotek Inc.'s Opening Brief in Support of Motion for Preliminary Injunction, *DNA Genotek, Inc. v. Spectrum DNA; Spectrum Solutions L.L.C., and Spectrum Packaging, LLC*, Case No. 15-CV-00661-SLR, dated Aug. 24, 2015 (26 pages).
Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015 (154 pages).
The American Heritage Dictionary of the English Language, Fourth Edition (2000) (definitions of: "corner"; "fastener"; "inert"; "reservoir"; "vial"), dated Oct. 20, 2015 (8 pages).
Defendants' Brief in Opposition to DNA Genotek's Motion for Preliminary Injunction, *DNA Genotek, Inc. v. Spectrum DNA; Spectrum Solutions L.L.C., and Spectrum Packaging, LLC*, Case No. 15-CV-00661-SLR, dated Oct. 2, 2015 (37 pages).
Declaration of Terry Layton, Ph.D. in Support of Defendants' Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015 (38 pages).
Numerical Designation of U.S. Pat. No. 8,221,381 Claim Element or Limitation, dated Oct. 20, 2015 (4 pages).
U.S. Appl. No. 60/523,104, filed Nov. 19, 2003 by Michael O'Donovan (9 pages).
Notice of Filing Date Accorded to Petition and Time for Filing Patent Owner Preliminary Response, Case IPR 2016-00060, dated Nov. 3, 2015 (3 pages).
Resubmitted Petition for Inter Partes Review of U.S. Pat. No. 8,221,381, Inter Partes Review No. IPR 2016-00060, dated Nov. 5, 2015 (69 pages).
Declaration of Thomas R. Varner, Ph.D. in Support of Defendants' Opposition to DNA Genotek's Motion for Preliminary Injunction, *DNA Genotek, Inc. v. Spectrum DNA, Spectrum Solutions, LLC and Spectrum Packaging, LLC*, Case No. 15-661-SLR, dated Oct. 2, 2015 (31 pages).
Declaration of Melanie L. Mayer in Support of Defendants' Brief in Opposition to DNA Genotek's Motion for Preliminary Injunction, *DNA Genotek, Inc. v. Spectrum DNA, Spectrum Solutions, LLC and Spectrum Packages, LLC*, Case No. 15-661-SLR, dated Oct. 2, 2015 (256 pages).
Defendants' Reply Brief in Support of Motion to Dismiss DNA Genotek's Complaint for Lack of Personal Jurisdiction, *DNA Genotek, Inc. v. Spectrum DNA, Spectrum Solutions, LLC and Spectrum Packaging, LLC*,Case No. 15-661-SLR, dated Oct. 16, 2015 (15 pages).
Reply Declaration of Gregg Williams in Support of Defendants' Motion to Dismiss for Lack of Personal Jurisdiction, *DNA Genotek, Inc. v. Spectrum DNA, Spectrum Solutions, LLC and Spectrum Packaging, LLC*, Case No. 15-661-SLR, dated Oct. 16, 2015 (3 pages).
Declaration of Melanie L. Mayer in Support of Defendants' Reply Brief in Support of Motion to Dismiss DNA Genotek's Complaint for Lack of Personal Jurisdiction, *DNA Genotek, Inc. v. Spectrum DNA, Spectrum Solutions, LLC and Spectrum Packaging, LLC*, Case No. 15-661-SLR, dated Oct. 16, 2015 (15 pages).
Declaration of John M. Collins in Support of DNA Genotek's Reply in Support of the Motion for Preliminary Injunction, *DNA Genotek, Inc. v. Spectrum DNA, Spectrum Solutions, LLC and Spectrum Packaging, LLC*, Case No. 15-cv-00661-SLR, dated Nov. 5, 2015 (154 pages).
Plaintiff DNA Genotek Inc.'s Reply Brief in Support of its Motion for Preliminary Injunction, *DNA Genotek, Inc. v. Spectrum DNA, Spectrum Solutions, LLC and Spectrum Packaging, LLC*, Case No. 15-00661-SLR, dated Nov. 5, 2015 (27 pages).
Declaration of Brian M. Kramer in Support of Plaintiff DNA Genotek Inc.'s Reply Brief in Support of its Motion for Preliminary Injunction, *DNA Genotek, Inc. v. Spectrum DNA, Spectrum Solutions, LLC and Spectrum Packaging, LLC*, Case No. 15-661-SLR, dated Nov. 5, 2015 (79 pages).
Defendants' Unopposed Motion for Leave to File a Surreply in Further Opposition to Plaintiffs Motion for a Preliminary Injunction, *DNA Genotek, Inc. v. Spectrum DNA, Spectrum Solutions, LLC and Spectrum Packaging, LLC*, Case No. 15-661-SLR, dated Nov. 19, 2015 (74 pages).
Letter to Judge Sue L. Robinson of the United States District Court regarding Motion for Leave, *DNA Genotek, Inc. v. Spectrum DNA, et al.*, Case No. 15-661-SLR, dated Nov. 20, 2015 (1 page).
DNA Genotek Inc.'s Opposition to Defendants' "Unopposed" Motion for Leave to File Surreply and DNA Genotek Inc.'s Motion to Strike Unauthorized Expert Declaration, *DNA Genotek, Inc. v. Spectrum DNA, Spectrum Solutions, LLC and Spectrum Packaging, LLC*, Case No. 15-661-SLR, dated Nov. 20, 2015 (9 pages).
Declaration of Brian M. Kramer in Support of DNA Genotek Inc.'s Opposition to Defendants' "Unopposed" Motion for Leave to File Surreply and DNA Genotek Inc.'s Motion to Strike Unauthorized Expert Declarations, *DNA Genotek, Inc. v. Spectrum DNA, Spec-*

(56) References Cited

OTHER PUBLICATIONS

*trum Solutions, LLC and Spectrum Packaging, LLC*, Case No. 15-661-SLR, dated Nov. 20, 2015 (12 pages).
Complaint, *DNA Genotek, Inc. v. Ancestry.com DNA, LLC*, dated May 4, 2015 (62 pages).
Complaint, *DNA Genotek, Inc. v. Spectrum DNA, Spectrum Solutions, LLC and Spectrum Packaging, LLC*, dated Jul. 30, 2015 (35 pages).
Report on the Filing or Determination of an Action Regarding a Patent or Trademark for U.S. Pat. No. 8,221,381, filed May 4, 2015 (1 page).
Report on the Filing or Determination of an Action Regarding a Patent or Trademark for U.S. D699,310, filed Jul. 30, 2015 (1 page).
First Amended Complaint, *DNA Genotek, Inc. v. Ancestry.com DNA, LLC*, Case No. 15-0355-SLR, dated Jul. 24, 2015 (62 pages).
DNA Genotek Inc.'s Motion for Preliminary Injunction, *DNA Genotek, Inc. v. Spectrum DNA, Spectrum Solutions, LLC and Spectrum Packaging, LLC*, Case No. 15-cv-00661-SLR, dated Aug. 24, 2015 (5 pages).
Defendant's Motion to Dismiss Genotek's Willful Infringement, Conversion, Trespass to Chattel, and Action to Quiet Title Claims, *DNA Genotek, Inc. v. Ancestry.com DNA, LLC*, Case No. 15-355-SLR, dated Aug. 10, 2015 (2 pages).
Declaration of Deforest McDuff, Ph.D., *DNA Genotek, Inc. v. Spectrum DNA, Spectrum Solutions, LLC and Spectrum Packaging, LLC*, Case No. 15-cv-00661-SLR, dated Aug. 24, 2015 (49 pages).
Ancestry DNA's Opening Brief in Support of Motion to Dismiss Genotek's Willful Infringement, Conversion, Trespass to Chattel, and Action to Quiet Title Claims, *DNA Genotek, Inc. v. Ancestry.com DNA, LLC*, Case No. 15-355-SLR, dated Aug. 10, 2015 (18 pages).
Declaration of Ian Curry, *DNA Genotek, Inc. v. Spectrum DNA, Spectrum Solutions, LLC and Spectrum Packaging, LLC*, Case No. 15-cv-00661, dated Aug. 24, 2015 (20 pages).
Declaration of Brian M. Kramer in Support of Motion for Preliminary Injunction, *DNA Genotek, Inc. v. Spectrum DNA, Spectrum Solutions, LLC and Spectrum Packaging, LLC*, Case No. 15-CV-00661-SLR, dated Aug. 24, 2015 (40 pages).
Plaintiff DNA Genotek Inc.'s Opposition to Ancestry.com DNA, LLC's Motion to Dismiss, *DNA Genotek, Inc. v. Ancestry.com DNA, LLC*, Case No. 15-355-SLR, dated Sep. 3, 2015 (24 pages).
Declaration of Brian M. Kramer in Support of Plaintiff DNA Genotek Inc.'s Opposition to Ancestry.com DNA, LLC's Motion to Dismiss, *DNA Genotek, Inc. v. Ancestry.com DNA, LLC*, Case No. 15-355-SLR, dated Sep. 3, 2015 (112 pages).
Defendants' Motion to Dismiss DNA Genotek's Complaint for Lack of Personal Jurisdiction, *DNA Genotek, Inc. v. Spectrum DNA, Spectrum Solutions, LLC and Spectrum Packaging, LLC*, Case No. 15-661-SLR, dated Sep. 4, 2015 (2 pages).
Ancestry.com DNA's Reply Brief in Support of Motion to Dismiss Genotek's Willful Infringement, Conversion, Trespass to Chattel, and Action to Quiet Title Claims, *DNA Genotek, Inc. v. Ancestry.com DNA, LLC*, Case No. 15-355-SLR, dated Sep. 18, 2015 (15 pages).
Declaration of Melanie Mayer in Support of Ancestry.com DNA's Reply Brief in Support of Motion to Dismiss Genotek's Willful Infringement, Conversion, Trespass to Chattel, and Action to Quiet Title Claims, *DNA Genotek, Inc. v. Ancestry.com DNA, LLC*, Case No. 15-355-SLR, dated Sep. 18, 2015 (2 pages).
Defendants' Opening Brief in Support of Motion to Dismiss DNA Genotek's Complaint for Lack of Personal Jurisdiction, *DNA Genotek, Inc. v. Spectrum DNA, Spectrum Solutions, LLC and Spectrum Packaging, LLC*, Case No. 15-661-SLR, dated Sep. 4, 2015 (15 pages).
Declaration of Gregg Williams in Support of Defendants' Motion to Dismiss for Lack of Personal Jurisdiction, *DNA Genotek, Inc. v. Spectrum DNA, Spectrum Solutions, LLC and Spectrum Packaging, LLC*, Case No. 15-661-SLR, dated Sep. 4, 2015 (4 pages).
Plaintiff DNA Genotek Inc.'s Answering Brief in Response to Defendants' Motion to Dismiss, *DNA Genotek, Inc. v. Spectrum DNA, Spectrum Solutions, LLC and Spectrum Packaging, LLC*, Case No. 15-661-SLR, dated Sep. 30, 2015 (25 pages).
Declaration of Brian M. Kramer in Support of DNA Genotek Inc.'s Answering Brief in Response to Defendants' Motion to Dismiss, *DNA Genotek, Inc. v. Spectrum DNA, Spectrum Solutions, LLC and Spectrum Packaging, LLC*, Case No. 15-661-SLR, dated Sep. 30, 2015 (31 pages).
Declaration of Gregg Williams in Support of Defendants' Opposition to DNA Genotek's Motion for Preliminary Injunction, *DNA Genotek, Inc. v. Spectrum DNA, Spectrum Solutions, LLC and Spectrum Packaging, LLC*, Case No. 15-661-SLR, dated Oct. 2, 2015 (3 pages).
Complaint for Patent Infringement, *DNA Genotek Inc. v. Spectrum Solutions L.L.C.*, Case No. '16CV1544 MMANLS, dated Jun. 20, 2016 (9 pages).
Patent Owner's Mandatory Notices, Inter Partes Review No. IPR 2016-01152, dated Jun. 24, 2016 (6 pages).
Notice of Filing Date Accorded to Petition and Time for Filing Patent Owner Preliminary Response, Inter Partes Review No. IPR 2016-01152, dated Jun. 9, 2016 (5 pages).
Petition for Inter Partes Review of U.S. Pat. No. 8,221,381, Inter Partes Review No. IPR 2016-01152, dated Jun. 3, 2016 (86 pages).
Exhibit 1001 of Petition for Inter Partes Review of U.S. Pat. No. 8,221,381, Inter Partes Review No. IPR 2016-01152, dated Jun. 3, 2016: U.S. Pat. No. 8,221,381 (Muir et al.) (25 pages).
Exhibit 1002 of Petition for Inter Partes Review of U.S. Pat. No. 8,221,381, Inter Partes Review No. IPR 2016-01152, dated Jun. 3, 2016: File History of U.S. Pat. No. 8,221,381 (401 pages).
Joint Motion to Terminate Proceeding pursuant to 35 U.S.C § 317(A), Inter Partes Review No. IPR 2016-01152, dated Feb. 1, 2017 (5 pages).
Exhibit 1004 of Petition for Inter Partes Review of U.S. Pat. No. 8,221,381, Inter Partes Review No. IPR 2016-01152, dated Jun. 3, 2016: Curriculum Vitae of Terry N. Layton, Ph.D. (4 pages).
Exhibit 1005 of Petition for Inter Partes Review of U.S. Pat. No. 8,221,381, Inter Partes Review No. IPR 2016-01152, dated Jun. 3, 2016: Plaintiff DNA Genotek Inc.'s Opening Brief in Support of Motion for Preliminary Injunction, *DNA Genotek, Inc. v. Spectrum DNA; Spectrum Solutions L.L.C., and Spectrum Packaging, LLC*, Case No. 15-CV-00661-SLR, dated Aug. 24, 2015 (26 pages).
Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-CV-00661-SLR, dated Aug. 24, 2015 (15 pages).
Exhibit A of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-CV-00661-SLR, dated Aug. 24, 2015: Curriculum vitae of Juan C. Lasheras, Ph.D., filed Aug. 24, 2015 (36 pages).
Exhibit B of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-CV-00661-SLR, dated Aug. 24, 2015: U.S. Pat. No. 8,221,381 B2, Jul. 17, 2012 (26 pages).
Exhibit C of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-CV-00661-SLR, dated Aug. 24, 2015: Spectrum Product Material Safety Data Sheet, filed Aug. 24, 2015 (11 pages).
Exhibit D of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc. v. Spectrum DNA; Spectrum Solutions L.L.C., and Spectrum Packaging, LLC*, Case No. 15-CV-00661-SLR, dated Aug. 24, 2015: Spectrum Product Marketing Sheet, filed Aug. 24, 2015 (2 pages).

(56) References Cited

OTHER PUBLICATIONS

Exhibit E of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc.* v. *Spectrum DNA; Spectrum Solutions L.L.C., and Spectrum Packaging, LLC*, Case No. 15-CV-00661-SLR, dated Aug. 24, 2015: Spectrum Product Instructions for Use, filed Aug. 24, 2015 (2 pages).
Exhibit F of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc.* v. *Spectrum DNA; Spectrum Solutions L.L.C., and Spectrum Packaging, LLC*, Case No. 15-CV-00661-SLR, dated Aug. 24, 2015: Claim chart demonstrating the limitation of Claim 1 of U.S. Pat. No. 8,221,381 in view of the Spectrum Device, filed Aug. 24, 2015 (12 pages).
Exhibit G of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc.* v. *Spectrum DNA; Spectrum Solutions L.L.C., and Spectrum Packaging, LLC*, Case No. 15-cv-00661-SLR, dated Aug. 24, 2015: WO 2015/017701 A1, Feb. 5, 2015 (22 pages).
Exhibit H of Exhibit 1006 of Petition for Inter Partes Review of U.S. Pat. No. 8,221,381, Inter Partes Review No. IPR 2016-01152, dated Jun. 3, 2016: Declaration of Juan C. Lasheras, Ph.D., *DNA Genotek, Inc.* v. *Spectrum DNA; Spectrum Solutions L.L.C., and Spectrum Packaging, LLC*, Case No. 15-CV-00661-SLR, dated Aug. 24, 2015: File History of U.S. Appl. No. 61/861,329, filed Aug. 1, 2013 (28 pages).
Exhibit 1007 of Petition for Inter Partes Review of U.S. Pat. No. 8,221,381, Inter Partes Review No. IPR 2016-01152, dated Jun. 3, 2016: U.S. Pat. No. 7,645,424 (O'Donovan) (8 pages).
Exhibit 1008 of Petition for Inter Partes Review of U.S. Pat. No. 8,221,381, Inter Partes Review No. IPR 2016-01152, dated Jun. 3, 2016: WO-2003/104251-A2 (DNA Genotek Inc) (50 pages).
Exhibit 1009 of Petition for Inter Partes Review of U.S. Pat. No. 8,221,381, Inter Partes Review No. IPR 2016-01152, dated Jun. 3, 2016: U.S. Pat. No. 6,152,296 (Shih) (9 pages).
Exhibit 1010 of Petition for Inter Partes Review of U.S. Pat. No. 8,221,381, Inter Partes Review No. IPR 2016-01152, dated Jun. 3, 2016: WO-98-03265-A1 (Kyoritsu Chemical-check Lab., Corp) (44 pages).
Exhibit 1011 of Petition for Inter Partes Review of U.S. Pat. No. 8,221,381, Inter Partes Review No. IPR 2016-01152, dated Jun. 3, 2016: (Certified English Translation) WO-98/03265-A1 (Kyoritsu Chemical-check Lab., Corp) (30 pages).
Exhibit 1012 of Petition for Inter Partes Review of U.S. Pat. No. 8,221,381, Inter Partes Review No. IPR 2016-01152, dated Jun. 3, 2016: DE-199 50 884-A1 (Wella Ag) (8 pages).
Exhibit 1013 of Petition for Inter Partes Review of U.S. Pat. No. 8,221,381, Inter Partes Review No. IPR 2016-01152, dated Jun. 3, 2016: (Certified English Translation) DE-199 50 884-A1 (Wella Ag) (8 pages).
Exhibit 1014 of Petition for Inter Partes Review of U.S. Pat. No. 8,221,381, Inter Partes Review No. IPR 2016-01152, dated Jun. 3, 2016: U.S. Pat. No. 6,228,323 (Asgharian et al.) (23 pages).
Exhibit 1015 of Petition for Inter Partes Review of U.S. Pat. No. 8,221,381, Inter Partes Review No. IPR 2016-01152, dated Jun. 3, 2016: The American Heritage Dictionary of the English Language, Fourth Edition (2000) (definitions of: "corner"; "fastener"; "inert"; "pointed"; "reservoir"; "vial") (8 pages).
Exhibit 1016 of Petition for Inter Partes Review of U.S. Pat. No. 8,221,381, Inter Partes Review No. IPR 2016-01152, dated Jun. 3, 2016: Defendants' Brief in Opposition to DNA Genotek's Motion of Preliminary Injunction, *DNA Genotek, Inc.* v. *Spectrum DNA: Spectrum Solutions L.L.C., and Spectrum Packaging, LLC*, Case No. 15-cv-00661-SLR, dated Oct. 2, 2015 (37 pages).
Exhibit 1017 of Petition for Inter Partes Review of U.S. Pat. No. 8,221,381, Inter Partes Review No. IPR 2016-01152, dated Jun. 3, 2016: Declaration of Terry Layton, Ph.D. in Support of Defendants' Opposition to DNA Genotek's Motion for Preliminary Injunction, *DNA Genotek, Inc.* v. *Spectrum DNA; Spectrum Solutions L.L.C., and Spectrum Packaging, LLC*, Case No. 15-CV-00661-SLR, dated Oct. 2, 2015 (38 pages).
Exhibit 1018 of Petition for Inter Partes Review of U.S. Pat. No. 8,221,381, Inter Partes Review No. IPR 2016-01152, dated Jun. 3, 2016: U.S. Appl. No. 60/523,104, filed Nov. 19, 2003 by Michael O'Donovan (9 pages).
Exhibit 1019 of Petition for Inter Partes Review of U.S. Pat. No. 8,221,381, Inter Partes Review No. IPR 2016-01152, dated Jun. 3, 2016: Numerical Designation of U.S. Pat. No. 8,221,381 Claim Element or Limitation (4 pages).
Exhibit 1020 of Petition for Inter Partes Review of U.S. Pat. No. 8,221,381, Inter Partes Review No. IPR 2016-01152, dated Jun. 3, 2016: U.S. Pre-Grant publication No. 2003/0089627 A1 ("Chelles") (8 pages).
Exhibit 1021 of Petition for Inter Partes Review of U.S. Pat. No. 8,221,381, Inter Partes Review No. IPR 2016-01152, dated Jun. 3, 2016: PCT publication No. WO-2005/023667 A1 ("Clarkson") (36 pages).
Exhibit 1022 of Petition for Inter Partes Review of U.S. Pat. No. 8,221,381, Inter Partes Review No. IPR 2016-01152, dated Jun. 3, 2016: Proof of Service, Case No. 1:15-cv-00355-SLR, United States District Court for the District of Delaware, dated Jun. 4, 2015 (2 pages).
Exhibit 1023 of Petition for Inter Partes Review of U.S. Pat. No. 8,221,381, Inter Partes Review No. IPR 2016-01152, dated Jun. 3, 2016: Pending claims, U.S. Appl. No. 12/338,873 ("Birnboim '873 application") (4 pages).
Exhibit 1024 of Petition for Inter Partes Review of U.S. Pat. No. 8,221,381, Inter Partes Review No. IPR 2016-01152, dated Jun. 3, 2016: Abstract of title, U.S. Appl. No. 12/338,873 ("Birnboim '873 application"), dated Jun. 1, 2016 (1 page).
Exhibit 1025 of Petition for Inter Partes Review of U.S. Pat. No. 8,221,381, Inter Partes Review No. IPR 2016-01152, dated Jun. 3, 2016: Deposition of John Collins, Ph.D., *DNA Genotek, Inc.* v. *Spectrum DNA; Spectrum Solutions L.L.C., and Spectrum Packaging, LLC*, Case No. 15-cv-00661-SLR, dated Nov. 13, 2015 (3 pages).
Petition for Inter Partes Review of U.S. Pat. No. 9,207,164, Inter Partes Review No. IPR 2016-01467, dated Jul. 20, 2016 (83 pages).
Exhibit 1001 of Petition for Inter Partes Review of U.S. Pat. No. 9,207,164, Inter Partes Review No. IPR 2016-01467, dated Jul. 20, 2016: U.S. Pat. No. 9,207,164 (Muir et al.) (32 pages).
Exhibit 1002 of Petition for Inter Partes Review of U.S. Pat. No. 9,207,164, Inter Partes Review No. IPR 2016-01467, dated Jul. 20, 2016: File History of U.S. Pat. No. 9,207,164 (545 pages).
Exhibit 1003 of Petition for Inter Partes Review of U.S. Pat. No. 9,207,164, Inter Partes Review No. IPR 2016-01467, dated Jul. 20, 2016: Declaration of Terry N. Layton, Ph.D. (100 pages).
Exhibit 1004 of Petition for Inter Partes Review of U.S. Pat. No. 9,207,164, Inter Partes Review No. IPR 2016-01467, dated Jul. 20, 2016: Curriculum Vitae of Terry N. Layton, Ph.D. (4 pages).
Exhibit 1005 of Petition for Inter Partes Review of U.S. Pat. No. 9,207,164, Inter Partes Review No. IPR 2016-01467, dated Jul. 20, 2016: Plaintiff DNA Genotek Inc.'s Opening Brief in Support of Motion for Preliminary Injunction, *DNA Genotek, Inc.* v. *Spectrum DNA; Spectrum Solutions L.L.C., and Spectrum Packaging, LLC*, Case No. 15-CV-00661-SLR, dated Aug. 24, 2015 (26 pages).
Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc.* v. *Spectrum DNA; Spectrum Solutions L.L.C., and Spectrum Packaging, LLC*, Case No. 15-CV-00661-SLR, dated Aug. 24, 2015 (15 pages).
Exhibit A of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc.* v. *Spectrum DNA; Spectrum Solutions L.L.C., and Spectrum Packaging, LLC*, Case No. 15-CV-00661-SLR, dated Aug. 24, 2015: Curriculum vitae of Juan C. Lasheras, Ph.D., filed Aug. 24, 2015 (36 pages).

(56) References Cited

OTHER PUBLICATIONS

Exhibit B of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: U.S. Pat. No. 8,221,381 B2, Jul. 17, 2012 (26 pages).

Exhibit C of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-CV-0061-SLR, dated Aug. 24, 2015: Spectrum Product Material Safety Data Sheet, filed Aug. 24, 2015 (11 pages).

Exhibit D of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging LC*, Case No. 15-CV-0061-SLR, dated Aug. 24, 2015: Spectrum Product Marketing Sheet, filed Aug. 24, 2015 (2 pages).

Exhibit E of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-CV-00661-SLR, dated Aug. 24, 2015: Spectrum Product Instructions for Use, filed Aug. 24, 2015 (2 pages).

Exhibit F of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-cv-00661-SLR, dated Aug. 24, 2015: Claim chart demonstrating the limitation of Claim 1 of U.S. Pat. No. 8,221,381 in view of the Spectrum Device, filed Aug. 24, 2015 (12 pages).

Exhibit G of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-CV-00661-SLR, dated Aug. 24, 2015: WO 2015/017701 A1, Feb. 5, 2015 (22 pages).

Exhibit H of Exhibit 1006 of Petition for Inter Partes Review of U.S. Pat. No. 9,207,164, Inter Partes Review No. IPR 2016-01467, dated Jul. 20, 2016: Declaration of Juan C. Lasheras, Ph.D., *DNA Genotek, Inc. v. Spectrum DNA; Spectrum Solutions L.L.C., and Spectrum Packaging, LLC*, Case No. 15-CV-00661-SLR, dated Aug. 24, 2015: File History of U.S. Appl. No. 61/861,329, filed Aug. 1, 2013 (28 pages).

Exhibit 1007 of Petition for Inter Partes Review of U.S. Pat. No. 9,207,164, Inter Partes Review No. IPR 2016-01467, dated Jul. 20, 2016: U.S. Pat. No. 7,645,424 (O'Donovan) (8 pages).

Exhibit 1008 of Petition for Inter Partes Review of U.S. Pat. No. 9,207,164, Inter Partes Review No. IPR 2016-01467, dated Jul. 20, 2016: WO-2003/104251-A2 (DNA Genotek Inc) (50 pages).

Exhibit 1009 of Petition for Inter Partes Review of U.S. Pat. No. 9,207,164, Inter Partes Review No. IPR 2016-01467, dated Jul. 20, 2016: U.S. Pat. No. 6,152,296 (Shih) (9 pages).

Exhibit 1010 of Petition for Inter Partes Review of U.S. Pat. No. 9,207,164, Inter Partes Review No. IPR 2016-01467, dated Jul. 20, 2016: WO-98/03265 A1 (Kyoritsu Chemical-check Lab., Corp) (44 pages).

Exhibit 1011 of Petition for Inter Partes Review of U.S. Pat. No. 9,207,164, Inter Partes Review No. IPR 2016-01467, dated Jul. 20, 2016: (Certified English Translation) WO-98/03265 A1 (Kyoritsu Chemical-check Lab., Corp) (30 pages).

Exhibit 1012 of Petition for Inter Partes Review of U.S. Pat. No. 9,207,164, Inter Partes Review No. IPR 2016-01467, dated Jul. 20, 2016: DE-199 50 884-A1 (Wella Ag) (8 pages).

Exhibit 1013 of Petition for Inter Partes Review of U.S. Pat. No. 9,207,164, Inter Partes Review No. IPR 2016-01467, dated Jul. 20, 2016: (Certified English Translation) DE-199 50 884-A1 (Wella Ag) (8 pages).

Exhibit 1014 of Petition for Inter Partes Review of U.S. Pat. No. 9,207,164, Inter Partes Review No. IPR 2016-01467, dated Jul. 20, 2016: U.S. Pat. No. 6,228,323 (Asgharian et al.) (23 pages).

Exhibit 1015 of Petition for Inter Partes Review of U.S. Pat. No. 9,207,164, Inter Partes Review No. IPR 2016-01467, dated Jul. 20, 2016: The American Heritage Dictionary of the English Language, Fourth Edition (2000) (definitions of: "corner"; "fastener"; "inert"; "reservoir"; "vial") (8 pages).

Exhibit 1016 of Petition for Inter Partes Review of U.S. Pat. No. 9,207,164, Inter Partes Review No. IPR 2016-01467, dated Jul. 20, 2016: Defendants' Brief in Opposition to DNA Genotek's Motion for Preliminary Injunction, *DNA Genotek, Inc. v. Spectrum DNA; Spectrum Solutions L.L.C., and Spectrum Packaging, LLC*, Case No. 15-cv-00661-SLR, dated Oct. 2, 2015 (37 pages).

Exhibit 1017 of Petition for Inter Partes Review of U.S. Pat. No. 9,207,164, Inter Partes Review No. IPR 2016-01467, dated Jul. 20, 2016: Declaration of Terry Layton, Ph.D. in Support of Defendants' Opposition to DNA Genotek's Motion for Preliminary Injunction, *DNA Genotek, Inc. v. Spectrum DNA; Spectrum Solutions L.L.C., and Spectrum Packaging, LLC*, Case No. 15-CV-00661-SLR, dated Oct. 2, 2015 (38 pages).

Exhibit 1018 of Petition for Inter Partes Review of U.S. Pat. No. 9,207,164, Inter Partes Review No. IPR 2016-01467, dated Jul. 20, 2016: U.S. Appl. No. 60/523,104, filed Nov. 19, 2003 by Michael O'Donovan (9 pages).

Exhibit 1019 of Petition for Inter Partes Review of U.S. Pat. No. 9,207,164, Inter Partes Review No. IPR 2016-01467, dated Jul. 20, 2016: Numerical Designation of U.S. Pat. No. 8,221,381 Claim Element or Limitation (4 pages).

Exhibit 1020 of Petition for Inter Partes Review of U.S. Pat. No. 9,207,164, Inter Partes Review No. IPR 2016-01467, dated Jul. 20, 2016: U.S. Pre-Grant publication No. 2003/0089627 A1 ("Chelles") (8 pages).

Exhibit 1021 of Petition for Inter Partes Review of U.S. Pat. No. 9,207,164, Inter Partes Review No. IPR 2016-01467, dated Jul. 20, 2016: PCT publication No. WO-2005/023667 A1 ("Clarkson") (36 pages).

Exhibit 1022 of Petition for Inter Partes Review of U.S. Pat. No. 9,207,164, Inter Partes Review No. IPR 2016-01467, dated Jul. 20, 2015: Proof of Service, case 1:15-cv-00355-SLR, United States District Court for the District of Delaware, dated Jun. 4, 2016 (2 pages).

Exhibit 1023 of Petition for Inter Partes Review of U.S. Pat. No. 9,207,164, Inter Partes Review No. IPR 2016-01467, dated Jul. 20, 2016: Pending claims, U.S. Appl. No. 12/338,873 ("Birnboim '873 application") (4 pages).

Exhibit 1024 of Petition for Inter Partes Review of U.S. Pat. No. 9,207,164, Inter Partes Review No. IPR 2016-01467, dated Jul. 20, 2016: Abstract of title, U.S. Appl. No. 12/338,873 ("Birnboim '873 application"), dated Jun. 1, 2016 (1 page).

Exhibit 1025 of Petition for Inter Partes Review of U.S. Pat. No. 9,207,164, Inter Partes Review No. IPR 2016-01467, dated Jul. 20, 2016: Deposition of John Collins, Ph.D., *DNA Genotek, Inc. v. Spectrum DNA; Spectrum Solutions L.L.C., and Spectrum Packaging, LLC*, Case No. 15-cv-00661-SLR, dated Nov. 13, 2015 (3 pages).

Exhibit 1026 of Petition for Inter Partes Review of U.S. Pat. No. 9,207,164, Inter Partes Review No. IPR 2016-01467, dated Jul. 20, 2016: U.S. Pat. No. 8,221,381 (Muir et al.) (25 pages).

Exhibit 1027 of Petition for Inter Partes Review of U.S. Pat. No. 9,207,164, Inter Partes Review No. IPR 2016-01467, dated Jul. 20, 2016: File History of U.S. Pat. No. 8,221,381 (401 pages).

Exhibit 1028 of Petition for Inter Partes Review of U.S. Pat. No. 9,207,164, Inter Partes Review No. IPR 2016-01467, dated Jul. 20, 2016: Affidavit of Service on Spectrum Solutions, LLC for Summons and Complaint, case 3:16-cv-01544-JLS-NLS, United States District Court for the Southern District of California, dated Jun. 21, 2016 (2 pages).

(56) References Cited

OTHER PUBLICATIONS

Exhibit 1029 of Petition for Inter Partes Review of U.S. Pat. No. 9,207,164, Inter Partes Review No. IPR 2016-01467, dated Jul. 20, 2016: Affidavit of Service on Spectrum DNA R/A for Summons and Complaint, case 3:16-cv-01544-JLS-NLS, United States District Court for the Southern District of California, dated Jun. 21, 2016 (2 pages).
Exhibit 1030 of Petition for Inter Partes Review of U.S. Pat. No. 9,207,164, Inter Partes Review No. IPR 2016-01467, dated Jul. 20, 2016: Comparison of U.S. Pat. No. 9,207,164 and U.S. Pat. No. 8,221,381 Claim Elements or Limitations (12 pages).
Exhibit 1031 of Petition for Inter Partes Review of U.S. Pat. No. 9,207,164, Inter Partes Review No. IPR 2016-01467, dated Jul. 20, 2016: Redacted Memorandum of Points and Authorities in Support of Motion for Preliminary Injunction, *DNA Genotek Inc. v. Spectrum Solutions L.L.C., and Spectrum DNA*, Case No. 3:16-cv-01544-JLS-NLS (USDC—S.D. Cal.) (31 pages).
Exhibit 1032 of Petition for Inter Partes Review of U.S. Pat. No. 9,207,164, Inter Partes Review No. IPR 2016-01467, dated Jul. 20, 2016: Redacted Declaration of Juan C. Lasheras, Ph.D. in Support of Motion for Preliminary Injunction, *DNA Genotek Inc. v. Spectrum Solutions L.L.C., and Spectrum DNA*, Case No. 3:16-cv-01544-JLS-NLS (USDC—S.D. Cal.) (27 pages).
Patent Owner's Mandatory Notices, Inter Partes Review No. IPR 2016-01467, dated Aug. 12, 2016 (6 pages).
Notice of Filing Date Accorded to Petition and Time for Filing Patent Owner Preliminary Response, Inter Partes Review No. IPR 2016-01467, dated Aug. 17, 2016 (5 pages).
Patent Owner's Preliminary Response, Inter Partes Review No. IPR 2016-00060, dated Feb. 3, 2016 (51 pages).
Exhibit 2001 of Patent Owner's Preliminary Response, Inter Partes Review No. IPR 2016-00060, dated Feb. 3, 2016: Screenshot from the PTO's "Patent Application Information Retrieval" for U.S. Pat. No. 6,152,296, <http://portal.uspto.gov/pair/PublicPair>, accessed Feb. 3, 2016 (2 pages).
Exhibit 2002 of Patent Owner's Preliminary Response, Inter Partes Review No. IPR 2016-00060, dated Feb. 3, 2016: Screenshot of <http://uspto.gov/patent/contact-patents/patent-technology-centers-managemnet>, accessed Feb. 3, 2016 (57 pages).
Exhibit 2003 of Patent Owner's Preliminary Response, Inter Partes Review No. IPR 2016-00060, dated Feb. 3, 2016: Changes to Implement Miscellaneous Post Patent Provisions of the Leahy-Smith American Invents Act, 1421 Off. Gaz. Pat. & Trademark Office 1263, dated Dec. 29, 2015 (39 pages).
Patent Owner's Response, Inter Partes Review No. IPR 2016-00060, dated Jun. 22, 2016 (28 pages).
Exhibit 2004 of Patent Owner's Response, Inter Partes Review No. IPR 2016-00060, dated Jun. 22, 2016: Transcript of Deposition of Terry Layton, Ph.D., dated May 25, 2016 (172 pages).
Exhibit 2005 of Patent Owner's Response, Inter Partes Review No. IPR 2016-00060, dated Jun. 22, 2016: Declaration of John Collins, Ph.D., dated Jun. 22, 2016 (18 pages).
Exhibit 2006 of Patent Owner's Response, Inter Partes Review No. IPR 2016-00060, dated Jun. 22, 2016: John M. Collins, Ph.D. Resume (4 pages).
Exhibit 2007 of Patent Owner's Response, Inter Partes Review No. IPR 2016-00060, dated Jun. 22, 2016: Petition for Inter Partes Review of U.S. Pat. No. 8,221,381, filed Jun. 3, 2016 (86 pages).
Exhibit 2008 of Patent Owner's Response, Inter Partes Review No. IPR 2016-00060, dated Jun. 22, 2016: Declaration of Terry Layton, Ph.D. in Support of Petition for Inter Partes Review of U.S. Pat. No. 8,221,381, filed Jun. 3, 2016 (96 pages).
Exhibit 2009 of Patent Owner's Response, Inter Partes Review No. IPR 2016-00060, dated Jun. 22, 2016: U.S. Pat. No. 4,131,016, Dec. 26, 1978 (5 pages).
Exhibit 2010 of Patent Owner's Response, Inter Partes Review No. IPR 2016-00060, dated Jun. 22, 2016: U.S. Pat. No. 4,301,812, dated Nov. 24, 1981 (7 pages).
Exhibit 2011 of Patent Owner's Response, Inter Partes Review No. IPR 2016-00060, dated Jun. 22, 2016: ASTM D 1894-01, "Standard Test Method for Static and Kinetic Coefficients of Friction of Plastic Film and Sheeting," (6 pages).
Petitioner Ancestry.com DNA, LLC's Reply to Patent Owner's Response, Inter Partes Review No. IPR 2016-00060, dated Sep. 6, 2016 (40 pages).
Exhibit 1020 of PetitionerAncestry.com DNA, LLC's Reply to Patent Owner's Response, Inter Partes Review No. IPR 2016-00060, dated Sep. 6, 2016: Declaration of Michael J. Sacksteder in Support of Petitioner's Motion for Pro Hac Vice Admission of Michael J. Sacksteder Pursuant to 37 C.F.R. § 42.10(c), Feb. 2, 2016 (5 pages).
Exhibit 1021 of PetitionerAncestry.com DNA, LLC's Reply to Patent Owner's Response, Inter Partes Review No. IPR 2016-00060, dated Sep. 6, 2016: Declaration of Melanie L. Mayer in Support of Petitioner's Motion for Pro Hac Vice Admission of Melanie L. Mayer Pursuant to 37 C.F.R. § 42.10(c), dated Sep. 20, 2016 (5 pages).
Exhibit 1022 of Petitioner Ancestry.com DNA, LLC's Reply to Patent Owner's Response, Inter Partes Review No. IPR 2016-00060, dated Sep. 6, 2016: Resubmitted Petition for Inter Partes Review for U.S. Pat. No. 8,221,381, dated Nov. 5, 2015 (69 pages).
Exhibit 1023 of Petitioner Ancestry.com DNA, LLC's Reply to Patent Owner's Response, Inter Partes Review No. IPR 2016-00060, dated Sep. 6, 2016: Institution Decision from the Patent Trial and Appeal Board, dated Apr. 8, 2016 (23 pages).
Exhibit 1024 of Petitioner Ancestry.com DNA, LLC's Reply to Patent Owner's Response, Inter Partes Review No. IPR 2016-00060, dated Sep. 6, 2016: Deposition of John M. Collins, Ph.D., dated Aug. 24, 2016 (99 pages).
Exhibit 1025 of Petitioner Ancestry.com DNA, LLC's Reply to Patent Owner's Response, Inter Partes Review No. IPR 2016-00060, dated Sep. 6, 2016: Excerpt from the Deposition of John Collins, Ph.D., Nov. 13, 2015, *DNA Genotek Inc. v. Spectrum DNA, et al.*, USDC—D. Del. Case No. 15-CV-00661, dated Nov. 13, 2015 (5 pages).
Exhibit 1026 of Petitioner Ancestry.com DNA, LLC's Reply to Patent Owner's Response, Inter Partes Review No. IPR 2016-00060, dated Sep. 6, 2016: Declaration of John M. Collins, Ph.D. in Support of Plaintiffs Reply in Support of Motion for Preliminary Injunction, *DNA Genotek Inc. v. Spectrum Solutions L.L.C.*, et al., USDC—S.D. Cal. Case No. 16-CV-01544, filed Aug. 19, 2016 (65 pages).
Exhibit 1027 of Petitioner Ancestry.com DNA, LLC's Reply to Patent Owner's Response, Inter Partes Review No. IPR 2016-00060, dated Sep. 6, 2016: Biomek® FX User's Manual, dated May 2000 (5 pages).
Petitioner's Notice of Deposition of John M. Collins, Ph.D., Inter Partes Review No. IPR 2016-00060, dated Aug. 2, 2016 (3 pages).
Patent Owner's Motion for Pro Hac Vice Admission of John R. Lanham under 37 C.F.R. § 42.10(c), Inter Partes Review No. IPR 2016-00060, dated Aug. 11, 2016 (7 pages).
Exhibit 2012 of Patent Owner's Motion for Pro Hac Vice Admission of John R. Lanham under 37 C.F.R. § 42.10(c), Inter Partes Review No. IPR 2016-00060, dated Aug. 11, 2016: Declaration of John R. Lanham in Support of Motion for Pro Hac Vice Admission of John R. Lanham under 37 C.F.R. § 42.10(c), dated Aug. 11, 2016 (4 pages).
Petitioner Ancestry.com DNA, LLC's Updated Exhibit List, Inter Partes Review No. IPR 2016-00060, dated Sep. 6, 2016 (5 pages).
Petitioner Ancestry.com DNA, LLC's Request for Oral Argument Pursuant to 37 C.F.R. § 42.70(a), Inter Partes Review No. IPR 2016-00060, dated Sep. 20, 2016 (4 pages).
Patent Owner's Request for Oral Argument, Inter Partes Review No. IPR 2016-00060, dated Oct. 26, 2016 (4 pages).
Petitioner's Mandatory Change-of-lnformation Notices under 37 C.F.R. § 42.8(a)(3), Inter Partes Review No. IPR 2016-00060, dated Dec. 5, 2016 (6 pages).
Decision Granting Motion for Pro Hac Vice Admission of Melanie L. Mayer 37 C.F.R. § 42.10, Inter Partes Review No. IPR 2016-00060, dated Feb. 25, 2016 (3 pages).

(56) References Cited

OTHER PUBLICATIONS

Decision Granting Motion for Pro Hac Vice Admission of Michael J. Stacksteder 37 C.F.R. § 42.10, Inter Partes Review No. IPR 2016-00060, dated Feb. 25, 2016 (3 pages).
Decision to Institute Inter Partes Review, Inter Partes Review No. IPR 2016-00060, dated Apr. 8, 2016 (23 pages).
Scheduling Order, Inter Partes Review No. IPR 2016-00060, dated Apr. 8, 2016 (7 pages).
Deposition Notice of Terry N. Layton, Ph.D., Inter Partes Review No. IPR 2016-00060, dated May 11, 2016 (3 pages).
Patent Owner's Updated Mandatory Notices, Inter Partes Review No. IPR 2016-00060, dated Jun. 23, 2016 (5 pages).
Request for Oral Hearing 37 C.F.R. § 42.70, Inter Partes Review No. IPR 2016-00060, dated Nov. 2, 2016 (4 pages).
Patent Owner's Preliminary Response, Inter Partes Review No. IPR 2016-01467, dated Nov. 17, 2016 (53 pages).
Exhibit 2001 of Patent Owner's Preliminary Response, Inter Partes Review No. IPR 2016-01467, dated Nov. 17, 2016: Resubmitted Petition, IPR2016-00060, Paper 5, dated Oct. 20, 2015 (69 pages).
Exhibit 2002 of Patent Owner's Preliminary Response, Inter Partes Review No. IPR 2016-01467, dated Nov. 17, 2016: Decision to Institute Inter Partes Review, IPR2016-00060, Paper 19 (23 pages).
Exhibit 2003 of Patent Owner's Preliminary Response, Inter Partes Review No. IPR 2016-01467, dated Nov. 17, 2016: Transcript of Deposition of Terry Layton, IPR2016-00060, Exhibit 2004, May 25, 2016 (172 pages).
Exhibit 2004 of Patent Owner's Preliminary Response, Inter Partes Review No. IPR 2016-01467, dated Nov. 17, 2016: Declaration of John M. Collins, IPR2016-00060, Exhibit 2005, dated Jun. 22, 2016 (18 pages).
Exhibit 2005 of Patent Owner's Preliminary Response, Inter Partes Review No. IPR 2016-01467, dated Nov. 17, 2016: Declaration of Terry Layton, IPR2016-01152, Exhibit 1003, dated Jun. 3, 2016 (96 pages).
Exhibit 2006 of Patent Owner's Preliminary Response, Inter Partes Review No. IPR 2016-01467, dated Nov. 17, 2016: Defendant's Responsive Claim Construction Brief, *DNA Genotek, Inc.* v. *Ancestry.com DNA, LLC*, Case No. 15-00355-SLR (D. Del.), dated Oct. 21, 2016 (36 pages).
Exhibit 2007 of Patent Owner's Preliminary Response, Inter Partes Review No. IPR 2016-01467, dated Nov. 17, 2016: Declaration of John M. Collins, Ph.D. in Support of Plaintiffs Reply in Support of Motion for Preliminary Injunction, *DNA Genotek, Inc.* v. *Spectrum Solutions L.L.C.; and Spectrum DNA*, Case No. 16-cv-01544-JLS-NLS (S.D. Cal.), dated Aug. 19, 2016 (65 pages).
Petitioner Ancestry.com DNA, LLC's Motion for Pro Hac Vice Admission of Michael J. Sacksteder pursuant to 37 C.F.R. §42. 10(c), IPR2016-01467, dated Sep. 20, 2016 (7 pages).
Exhibit 1033 of PetitionerAncestry.com DNA, LLC's Motion for Pro Hac Vice Admission of Michael J. Sacksteder pursuant to 37 C.F.R. § 42.10(c), IPR2016-01467, dated Sep. 20, 2016: Declaration of Michael J. Sacksteder in Support of Petitioner Ancestry.com DNA, LLC's Motion for Pro Hac Vice Admission of Michael J. Sacksteder pursuant to 37 C.F.R. § 42.10(c), dated Sep. 20, 2016 (5 pages).
Petitioner Ancestry.com DNA, LLC's Motion for Pro Hac Vice Admission of Melanie L. Mayer pursuant to 37 C.F.R. § 42.10(c), IPR2016-01467, dated Sep. 20, 2016 (7 pages).
Exhibit 1034 of PetitionerAncestry.com DNA, LLC's Motion for Pro Hac Vice Admission of Melanie L. Mayer pursuant to 37 C.F.R. § 42.10(c), IPR2016-01467, dated Sep. 20, 2016: Declaration of Melanie L. Mayer in Support of Petitioner Ancestry.com DNA, LLC's Motion for Pro Hac Vice Admission of Melanie L. Mayer pursuant to 37 C.F.R. § 42.10(c), dated Sep. 20, 2016 (5 pages).
Patent Owner's Preliminary Response, Inter Partes Review No. IPR 2016-01152, dated Sep. 9, 2016 (50 pages).
Exhibit 2001 of Patent Owner's Preliminary Response, Inter Partes Review No. IPR 2016-01152, dated Sep. 9, 2016: Resubmitted Petition for Inter Partes Review of U.S. Pat. No. 8,221,381, dated Nov. 5, 2015 (69 pages).

Exhibit 2002 of Patent Owner's Preliminary Response, Inter Partes Review No. IPR 2016-01152, dated Sep. 9, 2016: Petition for Inter Partes Review of U.S. Pat. No. 6,974,569 under 35 U.S.C. §§ 311-319 and 37 C.F.R. §§ 42.1-.80, 42.100-.123, dated Aug. 14, 2013 (64 pages).
Exhibit 2003 of Patent Owner's Preliminary Response, Inter Partes Review No. IPR 2016-01152, dated Sep. 9, 2016: Petition for Inter Partes Review of U.S. Pat. No. 6,974,569 under 35 U.S.C. §§ 311-319 and 37 C.F.R. §§ 42.1-.80, 42.100-.123, dated Mar. 12, 2014 (62 pages).
Petitioner Ancestry.com DNA, LLC's Motion for Pro Hac Vice Admission of Michael J. Sacksteder pursuant to 37 C.F.R. § 42.10(c), dated Sep. 20, 2016 (7 pages).
Exhibit 1026 of Petitioner Ancestry.com DNA, LLC's Motion for Pro Hac Vice Admission of Michael J. Sacksteder pursuant to 37 C.F.R. § 42.10(c), dated Sep. 20, 2016: Declaration of Michael J. Sacksteder in Support of Petitioner's Motion for Pro Hac Vice Admission of Michael J. Sacksteder pursuant to 37 C.F.R. § 42.10(c), Sep. 20, 2016 (4 pages).
Petitioner Ancestry.com DNA, LLC's Motion for Pro Hac Vice Admission of Melanie L. Mayer pursuant to 37 C.F.R. §42.10(c), dated Sep. 20, 2016 (7 pages).
Exhibit 1027 of PetitionerAncestry.com DNA, LLC's Motion for Pro Hac Vice Admission of Melanie L. Mayer pursuant to 37 C.F.R. § 42.10(c), dated Sep. 20, 2016: Declaration of Melanie L. Mayer in Support of Petitioner's Motion for Pro Hac Vice Admission of Melanie L. Mayer pursuant to 37 C.F.R. § 42.10(c), Sep. 20, 2016 (4 pages).
Order Granting Motion for Pro Hac Vice Admission of Melanie L. Mayer 37 C.F.R. § 42.10, dated Sep. 28, 2016 (3 pages).
Order Granting Motion for Pro Hac Vice Admission of Michael J. Sacksteder 37 C.F.R. § 42.10, dated Sep. 28, 2016 (3 pages).
Decision Denying Institution of Inter Partes Review 37 C.F.R. § 42.108, dated Nov. 23, 2016 (13 pages).
Exhibit 2001 of Patent Response, Inter Partes Review No. IPR 2016-00060, dated Jun. 22, 2016: Screenshot from the PTO's "Patent Application Information Retrieval" for U.S. Pat. No. 6,152,296, <http://portal.uspto.gov/pair/PublicPair> accessed Feb. 3, 2016 (2 pages).
Exhibit 2002 of Patent Owner's Response, Inter Partes Review No. IPR 2016-00060, dated Jun. 22, 2016: Screenshot of <http://uspto.gov/patent/contact-patents/patent-technology-centers-managemnet>, accessed Feb. 3, 2016 (57 pages).
Exhibit 2003 of Patent Owner's Response, Inter Partes Review No. IPR 2016-00060, dated Jun. 22, 2016: Changes to Implement Miscellaneous Post Patent Provisions of the Leahy-Smith American Invents Act, 1421 Off. Gaz. Pat. & Trademark Office 1263, dated Dec. 29, 2015 (39 pages).
Record of Oral Hearing, Inter Partes Review No. IPR 2016-00060, dated Jan. 12, 2017 (54 pages).
Joint Motion to Terminate Proceeding pursuant to 35 U.S.C § 317(A), Inter Partes Review No. IPR 2016-00060, dated Feb. 1, 2017 (5 pages).
Joint Request that the Settlement Agreement Filed Separately as Exhibit 2013 be Treated as Business Confidential Information and be Kept Separate from the Files, Inter Partes Review No. IPR 2016-00060, dated Feb. 1, 2017 (4 pages).
French et al., "Ultra/Rapid DNA Analysis Using HyBeacon™ Probes and Direct PR Amplification from Saliva," Molecular and Cellular Probes, 2002, 16: 319-326.
Hiraide et al., "Speciation of Iron in River Water," Analytical Sciences, 1988, 4: 605-609.
Nilsson et al., "Real/Time Monitoring of DNA Manipulations Using Biosensor Technology," Analytical Biochemistry, 1995, 224: 400-408.
Roberts et al., "UV Laser Machined Polymer Substrates for the Development of Microdiagnostic Systems," Analytical Chemistry, 1997, 69: 2035-2042.
Seutin et al., "Preservation of Avian Blood and Tissue Samples for DNA Analyses," Canadian Journal of Zoology, 1991,69: 82-90.
Videira et al., "Assembly Kinetics and Identification of Precursor Proteins of Complex I from Neurospora Crassa," European Journal of Biochemistry, 1989,181: 493-502.

(56) References Cited

OTHER PUBLICATIONS

Simport Products, Tubes, Caps and Vials (http://wwv.simport.com/products/tubes/caps/and/vials/tubes/t501.html) Copyright 2009/2011.
"Living Hinge" from Wikipedia, the free encyclopedia.
"Box with Living Hinge"; efunda, Living Hinge; copyright 2012.
Dictionary entry for "Lid", p. 1615; The Compact Edition of the Oxford English Dictionary, vol. 1, A/O, Oxford University Press 1971 (printed in the USA) (Twenty/second printing in US, Jun. 1982) (Oxford, New York, etc.).
Bardon et al. (1980) "Properties of Purified Salivary Ribonuclease, and Salivary Ribonuclease Levels in Children with Cystic Fibrosis and in Heterozygous Carriers," Clinica Chimica Acta. 101:17-24.
Bardon et al. (1984) "Salivary Ribonuclease in Cyctic Fibrosis and Control Subjects," Acta Paediatr. Scand. 73:263-266.
Baron et al., "Why Is HIV Rarely Transmitted by Oral Secretions?" Arch Intern Med., 159:303-310 (1999).
Blumberg (1987) "Creating a ribonuclease-free environment," Methods Enzymol. 152:20-24.
Costa et al., "Epigenetic Downregulation of GABAergic Function in Schizophrenia: Potential for Pharmacological Intervention?" Mol Interv., 3(4):220-229 (Jun. 2003).
Donnelly et al. (2003) "Epidemiological determinants of spread of causal agent of severe acute respiratory syndrome in Hong Kong," The Lancet. 361:1761-1766, May 7, 2003.
Ehrenfeld et al. (1981) "Stability of Poliovirus RNA in Cell-free Translation Systems Utilizing Two Initiation Sites," The Journal of Biological Chemistry. 256(6):2656-2661.
Eichel et al. (1964) "Acid and Alkaline Ribonucleases of Human Parotid, Submaxillary, and Whole Saliva," Archives of Biochemistry and Biophysics. 107:197-208.
Google Web Page, "Preparing protein samples for sds-page", Dated Feb. 1, 2001, downloaded Aug. 25, 2015, 2 pages, Retrieved from: <https://www.google.com/search?q=sds+tris+edta&rls=com.microsofr/03Aen-USo/03AIE-Address&source=Int&tbs=cdr%3AI%2Ccdmin%3AI%2FI%2F1900%2Ccd_max%3A10%2F6%2F2005&tbm=>.
Guinn (1966) "Extraction of Nucleic Acids from Lyphilized Plant Material," Plant Physiology. 41:689-695.
Guy (2002) "Evaluation of Events Occurring at Mucosal Surfaces: Techniques Used to Collect and Analyze Mucosal Secretions and Cells," Clinical and Diagnostic Laboratory Immunology. 9(4):753-762.
Kay et al. (1952) "An Improved Preparation of Sodium desoxyribonucleate," Journal of the American Chemical Society. 74(7): 1724-1726.
Lal et al., "Fixation and Long-Term Storage of Human Lymphocytes for Surface Marker Analysis by Flow Cytometq," Cytometry, 9:213-219 (1988).
Noguera et al., "Enhanced neutrophil response in chronic obstructive pulmonary disease," Thorax, 56:432-437 (2001).
Okuno et al. (1979) "RNA Polymerase Activity and Protein Synthesis in Brome Mosaic Virus-Infected Protoplasts," Virology. 99:218-225.
Peiris et al. (2003) "Clinical progression and viral load in a community outbreak of coronavirus-associated SARS pneumonia: a prospective study," The Lancet 361:1767-1772, May 9, 2003.
Petronis et al., "Schizophrenia: An Epigenetic Puzzle?" Schizophrenia Bulletin, 25(4):639-655 (1999).
Quest Diagnostics, "Immunohist Chemistry Tests", 2000-2019, 8 pages, Retrieved from: <https://www.questdiagnostics.com/home/physicians/testing-services/specialists/hospitals-lab-staff/specimen-handling/immunohistochemistry.html>.
Reynolds et al., "Comparison of high density genotyping results from saliva and blood samples on Affymetrix GeneChip® GenomeWide SNP 6.0 arrays," Poster, 1 page.
Riddell et al. (2001) "Investigation of Optimal Specimen Type and Sampling Time for Detection of Measles Virus RNA during a Measles Epidemic," Journal of Clinical Microbiology. 39(1):375-376.
Rohan et al. (2000) "Optimization of the Week-Cel Collection Method for Quantitation of Cytokines in Mucosal Secretions," Clinical and Diagnostic Laboratory Immunology. 7(1):45-48.
Rosas et al., "Promoter Hypermethylation Patterns of p16, O6-ethylguanine-DNAmethyltransferase, and Death-associated Protein Kinase in Tumors and Saliva of Head and Neck Cancer Patients," Cancer Research, 61:939-942 (2001).
Roy et al. (1999) "The effect of saliva specimen collection, handling and storage protocols on hepatitis C virus (HCV) RNA detection by PCR," Oral Diseases. 5:123-127.
University of Texas, Austin, TX, "Chem 405 Biochemistry Lab I", Feb. 1, 2001, downloaded Feb. 22, 2015, 9 pages, Retrieved from: <http://www.einstein.net/pdf/1350246084.pdf>.
USDA, "Method Used to Extract Total Muscle Protein for Western Blot Using TRIS-EDTA Buffer", Submitted by Wheeler and Ekeren, published Feb. 1, 2001, 13 pages, Retrieved from: <http://www.ars.usda.gov/SP2UserFiles/Place/30400510/protocols/WesternBlot.pdf>.
Verwoerd et al. (1989) "A small-scale procedure for the rapid isolation of plant RNAs," Nucleic Acids Res. 17(6):2362.
Vitale (2001) "The Total RNA Story," Agilent Technologies. Publication No. 5988-2281EN. www.agilent.com/chem.
World Health Organization, "A multicentre collaboration to investigate the cause of severe acute respiratory syndrome," The Lancet. 361:1730-1733, May 17, 2003.
Yamamoto et al., "Airway Inflammation in COPD Assessed by Sputum levels of Interleukin-8," Chest, 112:505-510 (1997).
U.S. Appl. No. 10/455,680 / 2004/0038269 / U.S. Pat. No. 7,482,116, filed Jun. 5, 2003 / Feb. 26, 2004 / Jan. 27, 2009, H. Chaim Birnboim.
U.S. Appl. No. 12/338,848 / 2009/0162924, filed Dec. 18, 2008 / Jun. 25, 2009, H. Chaim Birnboim.
U.S. Appl. No. 12/338,873 / 2009/0162866, filed Dec. 18, 2008 / Jun. 25, 2009, H. Chaim Birnboim.
U.S. Appl. No. 14/549,344 / 2015/0104803 / U.S. Pat. No. 9,523,115, filed Nov. 20, 2014 / Apr. 16, 2015 / Dec. 20, 2016, H. Chaim Birnboim.
U.S. Appl. No. 15/345,420 2017/0152545 U.S. Pat. No. 10,619,187, filed Nov. 7, 2016 Jun. 1, 2017 Apr. 14, 2020, H. Chaim Birnboim.
U.S. Appl. No. 16/809,131 2020/0354769, filed Mar. 4, 2020 Nov. 12, 2020, H. Chaim Birnboim.
DNA Genotek filed suit against Spectrum Pharmaceuticals for infringement of U.S. Pat. No. 10,619,187 on Mar. 24, 2021, U.S. District Court, S.D. Cal., C.A. No. 21-cv-0516. (Doc. No. 1.).
DNA Genotek filed a First Amended Complaint dated Jun. 8, 2021. The First Amended Complaint also asserted a claim for infringement of U.S. Pat. No. 10,619,187. (Doc. No. 12.).
Spectrum filed an Answer and Counterclaim to the First Amended Complaint dated Jun. 22, 2021. Spectrum asserted counterclaims for a declaratory judgment of noninfringement and invalidity under one or more of "35 U.S.C. §§102, 103, and 112, as well as other judicially created bases for patent invalidity," stating "[a]s a non-limiting example, at least Claim 1 of the '187 patent is invalid in view of at least U.S. Pat. No. 5,827,675, U.S. Pat. No. 6,309,827; and/or EP Patent No. 0734684." (Doc. No. 13.).
DNA Genotek filed an Answer to Spectrum's counterclaims on Jul. 13, 2021. (Doc. No. 16.).
DNA Genotek filed a Second Amended Complaint dated Aug. 4, 2021. The Second Amended Complaint asserted claims for infringement of U.S. Pat. No. 10,619,187 and U.S. Appl. No. 11/002,646. (Doc. No. 20.).
Spectrum filed an Answer and Counterclaim to the Second Amended Complaint dated Aug. 18, 2021. Spectrum asserted affirmative defenses and counterclaims for declaratory judgment of noninfringement, invalidity, inequitable conduct, monopolization, and attempted monopolization. (See Affirmative Defenses at pp. 8-30; Counterclaim at pp. 31-66.) (Doc. No. 27.).
DNA Genotek filed a Motion to Dismiss and Strike Spectrum's Counterclaims and Affirmative Defenses Pursuant to Fed. R. Civ. P. 12(B)(6) and 12(F) dated Oct. 14, 2021. (Doc. No. 41 and Doc. No. 41-1.) the motion to dismiss is currently pending.

(56) References Cited

OTHER PUBLICATIONS

Complaint for Patent Infringement against Spectrum Pharmaceuticals, S.D. Cal., Case No. 21-cv-0516, Filed Mar. 24, 2021 by DNA Genotek. (Document 1).
First Amended Complaint for Patent Infringement, S.D. Cal., Case No. 21-cv-0516, Filed Jun. 8, 2021 by DNA Genotek. (Document 12).
Spectrum's Answer and Counterclaim To First Amended Complaint, S.D. Cal., Case No. 21-cv-0516, Filed Jun. 22, 2021. (Document 13).
Plaintiff and Counter-Defendant DBA Genotek Inc.'S Answer To Defendant and Counter-Claimant Spectrum Solutions, LLC'S Counterclaims, S.D. Cal., Case No. 21-cv-0516, Filed Jul. 13, 2021. (Document 16).
Second Amended Complaint for Patent Infringement, S.D. Cal., Case No. 21-cv-0516, Filed Aug. 4, 2021 by DNA Genotek. (Document 20).
Spectrum's Answer and Counterclaim To Second Amended Complaint, S.D. Cal., Case No. 21-cv-0516. Filed Aug. 18, 2021. (Document 27).
Notice of Motion and Motion By Plaintiff DNA Genotek Inc. to Dismiss and Strike Defendant Spectrum Solutions LLC'S Counterclaims and Affirmative Defenses Pursuant To Fed. R. Civ. P. 12(B)(6) and 12(F), S.D. Cal., Case No. 21-cv-0516, Filed Oct. 14, 2021. (Document 41).
Memorandum of Points and Authorities in Support of DNA Genotek Inc.'S Motion To Dismiss and Strike Defendant Spectrum Solution LLC'S Counterclaims and Affirmative Defenses Pursuant To Fed. R. Civ. P. 12(B)(6) and 12(F), S.D. Cal., Case No. 21-cv-0516, Filed Oct. 14, 2021. (Document 41-1).
Condon C., "RNA processing and degradation in Bacillus subtilis" (2003) Microbiol Mol Biol Rev 67(2): 157-174. Doi: 10.1128/MMBR.67.2.157-174.2003.
Kim B-M, Schultz LW and Raines RT, "Variants of ribonuclease inhibitor that resist oxidation" (1999) Protein Science 8: 430-434.
M Jung, S Klotzek, M Lewandowski, M Fleischhacker, K Jung (2003) "Changes in concentration of DNA in serum and plasma during storage of blood samples", Clinical Chem 49(6): 1028-1029.
M Stroun, J Lyautey, C Lederrey, A Olson-Sand, P Anker (2001) "About the possible origin and mechanism of circulating DNA apoptosis and active DNA release", Clin Chim Acta. 313(1-2): 139-142.
Mikkelsen NE, Brannvall M, Virtanen A and Kirsebom LA, "Inhibition of RNAse P RNA cleavaae bv aminoglycosides", (1999) PNAS, 96: 6155-6160.
MJ Bussemakers, A van Bokhoven, GW Verhaegh, FP Smit, HFM Karthaus, JA Schalken, FMJ Debruyne, N Ru, WB Isaacs, (1999) "DD3: a new prostate-specific gene, highly overexpressed in prostate cancer", Cancer Res, 59: 5975-5979.
Muñoz N, Bosch FX, de Sanjose S, Herrero R, Castellsaque X, Shah KV, Snijders PJ, Meijer CJ, (2003) "Epidemiologic classification of human papillomavirus types associated with cervical cancer", N Engl J Med 348(6): 518-527. Doi: 10.1056/NEJMoa021641.
P Anker, H Mulcahy, XQ Chen, M Stroun, (1999) "Detection of circulating tumour DNA in the blood (plasma/serum) of cancer patients", Cancer and Metastasis Reviews 18: 65-73, Doi. https://doi.org/10.1023/A:1006260319913.
P Mandel, P Metals, (1948) "Les acides nucleiques du plasma sanguine chez l'homme", C R Acad Sci Paris, 142: 241-243—with English machine translation.
S Jahr, H Hentze, S Englisch, D Hardt, FO Fackelmayer, RD Hesch, R Knippers, (2001) "DNA fragJAHR_2001ments in the blood plasma of cancer patients: quantitations and evidence for their origin from apoptotic and necrotic cells", Cancer Res 61 (4): 1659-1665.
SA Leon, B Shapiro, DM Sklaroff, MJ Yaros, (1977) "Free DNA in the serum of cancer patients and the effect of therapy", Cancer Res 37: 646-650.
Srinivasan M, Sedmak D, Jewell S, (2002) "Effect of fixatives and tissue processing on the content and integrity of nucleic acids", Am J Pathol 161(6): 1961-1971.
Wolf B, Lesnaw JA and Reichmann ME, "A mechanism of the irreversible inactivation of bovine pancreatic ribonuclease by diethylpyrocarbonate" (1970) Eur J Biochem 13: 519-525.
Restriction Requirement for U.S. Appl. No. 16/809,131, dated Nov. 4, 2021.
Spectrum filed a Memorandum in Opposition to DNA Genotek's Motion to. Dismiss and Strike Spectrum's Counterclaims and Affirmative Defenses on Jan. 11, 2022. (Doc. No. 76).
DNA Genotek filed a Reply in Support of its Motion to Dismiss and Strike Spectrum's Counterclaims and Affirmative Defenses on Feb. 1, 2022. (Doc. 78).
DNA Genotek submitted a Declaration of Brian M. Kramer in support of its Motion to Dismiss and Strike Spectrum's Counterclaims and Affirmative Defenses, along with Exhibits 1 through 4, on Feb. 1, 2022. (Doc. No. 78-1).
Exhibit 1 to the Declaration of Brian M. Kramer is a copy of the index of the electronic record for U.S. Appl. No. 16/986,765 ("The '765 application"). (Doc. No. 78-2).
Exhibit 2 to the Declaration of Brian M. Kramer is a copy of a list of references cited by DNA Genotek in the '765 application. (Doc. No. 78-3).
Exhibit 3 to the Declaration of Brian M. Kramer is a copy of an Information. Disclosure Statement filed by DNA Genotek in the '765 application. (Doc. No. 78-3).
Exhibit 4 to the Declaration of Brian M. Kramer is a copy of the Notice of Allowability of the '765 application. (Doc. No. 78-5).
Spectrum served Invalidity Contentions on Dna Genotek on Nov. 19, 2021. These Invalidity Contentions are not assigned a document number. The Invalidity Atty Dkt No. 708805: DNA5-001CON5DIV _Start_Table_ Contentions include Appendices A-K as listed. The "Charlton" reference cited in the Invalidity Contentions corresponds to CA 2236240 A1, published Oct. 29, 1999, to Biex, Inc., cited in an IDS in the present application dated Dec. 14, 2020.
Appendix A: Invalidity Claim Chart for U.S. Pat. No. 10,619,187, Fischetti—U.S. Pat. No. 5,643,767, dated Nov. 19, 2021.
Appendix B: Invalidity Claim Chart for U.S. Pat. No. 10,619,187, Soane—PCT Publication No. WO00/10884, dated Nov. 19, 2021.
Appendix C: Invalidity Claim Chart for U.S. Pat. No. 10,619,187, Moscovitz 113—U.S. Pat. No. 6,533,113, dated Nov. 19, 2021.
Appendix D: Invalidity Claim Chart for U.S. Pat. No. 10,619,187, Moscovitz 110—U.S. Pat. No. 6,527,110, dated Nov. 19, 2021.
Appendix E: Invalidity Claim Chart for U.S. Pat. No. 10,619,187, Okauchi—PCT Publication No. WO98/03265, dated Nov. 19, 2021.
Appendix F: Invalidity Claim Chart for U.S. Pat. No. 10,619,187, Finke—U.S. Pat. No. 4,591,050, dated Nov. 19, 2021.
Appendix G: Invalidity Claim Chart for U.S. Pat. No. 10,619,187, Guirguis—PCT Publication No. WO 98/038917, dated Nov. 19, 2021.
Appendix H: Claim Chart for U.S. Pat. No. 11,002,646, U.S. Patent Pub. No. 2009/0216213 ("Muir"), WO 2005/051775 ("Cho"), U.S. Pat. No. 5,967,309 (Robles-Gonzalez), U.S. 2009/0133366 ("Cronin"), dated Nov. 19, 2021.
Appendix I: Invalidity Claim Chart for U.S. Pat. No. 11,002,646, U.S. Patent Pub. No. 2012/0325721 ("Plante"), WO 2005/051775 ("Cho"), U.S. Pat. No. 5,967,309 ("Robles-Gonzalez"), U.S. Patent Pub. No. 2009/0133366 ("Cronin"), dated Nov. 19, 2021.
Appendix J: Claim Chart for U.S. Pat. No. 11,002,646, U.S. Patent Pub. No. 2004/0161788 ("Chen"), WO 2005/051775 ("Cho"), U.S. Pat. No. 5,967,309 ("Robles-Gonzalez"), U.S. Patent Pub. No. 2009/0133366 ("Cronin"), dated Nov. 19, 2021.
Appendix K: Invalidity Claim Chart for U.S. Pat. No. 11,002,646, U.S. 2008/0293156 ("Smith"), WO 2005/051775 ("Cho"), U.S. Pat. No. 5,967,309 ("Robles-Gonzalez"), U.S. Patent Pub. No. 2009/0133366 ("Cronin"), dated Nov. 19, 2021.
Spectrum Solutions, LLC's Opening Claim Construction Brief dated Feb. 18, 2022. (Doc. No. 83).
Declaration of Ali S. Razai in Support of Spectrum Solution LLC's Opening Claim Construction Brief dated Feb. 18, 2022. (Doc. No. 83-1).

(56) References Cited

OTHER PUBLICATIONS

Declaration of Vincent A. Fischetti, Ph.D. dated Feb. 19, 2022. (Doc. No. 87).
Defendant Spectrum Solutions, L.L.C.'s Responsive Claim Construction Brief dated Mar. 4, 2022. (Doc. No. 88).
Plaintiff DNA Genotek Inc.'s Responsive Claim Construction Brief dated Mar. 4, 2022. (Doc. No. 89).
Notice of Errata and Declaration of Vincent A. Fischetti, Ph.D. dated Mar. 21, 2022. (Doc. No. 100).
Order Denying Plaintiff/Counter Defendant's Motion to Dismiss Counterclaims and Denying Motion to Strike Without Prejudice dated Apr. 1, 2022. (Doc. No. 111).
DNA Genotek Inc.'s Answer to Spectrum Solutions L.L.C.'s Counterclaims dated. Apr. 13, 2022. (Doc. No. 115).
DNA Genotek Inc.'s Notice of Errata to Opening Claim Construction Brief dated Jul. 18, 2022. (Doc. No. 132).
DNA Genotek Inc.'s Corrected Opening Claim Construction Brief dated Jul. 19, 2022. (Doc. No. 134).
Docket dated Aug. 5, 2022, for *DNA Genotek Inc.v. Spectrum Solutions L.L.C.* before the United States District Court Southern District of California (*DNA Genotek Inc.v. Spectrum Solutions L.L.C.*, Case No. 21-cv-0516-JO-AGS).
"Spectrum Solution LLC's memorandum in opposition to DNA Genotek Inc.'s motion to dismiss and strike defendant Spectrum Solutions LLC's counterclaims and affirmative defenses" before the United States District Court Southern District of California (*DNA Genotek Inc.v. Spectrum Solutions L.L.C.*, Case No. 21-cv-0516-JO-AGS), dated Jan. 11, 2022. (Doc. No. 76).
"Reply in support of plaintiff DNA Genotek Inc.'s motion to dismiss and strike defendant Spectrum Solutions LLC's counterclaims and affirmative defenses pursuant to Fed. R. Civ. P. 12(B)(6) and 12(F)" before the United States District Court Southern District of California (*DNA Genotek Inc.v. Spectrum Solutions L.L.C.*, Case No. 21-CV-0516-JO-AGS), dated Feb. 1, 2022. (Doc. No. 78).
"Declaration of Brian M. Kramer in support of reply in support of DNA Genotek Inc.'s motion to dismiss and strike defendant Spectrum Solutions LLC's counterclaims and affirmative defenses pursuant to Fed. R. Civ. P. 12(B)(6) and 12(F)" before the United States District Court Southern District of California (*DNA Genotek Inc.v. Spectrum Solutions L.L.C.*, Case No. 21-CV-0516-JO-AGS), dated Feb. 1, 2022. (Doc. No. 78-1).
"Exhibit 1 to the Declaration of Brian M. Kramer in support of reply in support of DNA Genotek Inc.'s motion to dismiss and strike defendant Spectrum Solutions LLC's counterclaims and affirmative defenses pursuant to Fed. R. Civ. P. 12(B)(6) and 12(F)" before the United States District Court Southern District of California (*DNA Genotek Inc.v. Spectrum Solutions L.L.C.*, Case No. 21-cv-0516-JO-AGS), dated Feb. 1, 2022, is a copy of the index of the electronic record for U.S. Appl. No. 16/986,765 ("the 765 application"). (Doc. No. 78-2).
"Exhibit 2 to the Declaration of Brian M. Kramer in support of reply in support of DNA Genotek Inc.'s motion to dismiss and strike defendant Spectrum Solutions LLC's counterclaims and affirmative defenses pursuant to Fed. R. Civ. P. 12(B)(6) and 12(F)" before the United States District Court Southern District of California (*DNA Genotek Inc.v. Spectrum Solutions L.L.C.*, Case No. 21-cv-0516-JO-AGS), dated Feb. 1, 2022, is a copy of a list of references cited by DNA Genotek in the 765 application. (Doc. No. 78-3).
"Exhibit 3 to the Declaration of Brian M. Kramer in support of reply in support of DNA Genotek Inc.'s motion to dismiss and strike defendant Spectrum Solutions LLC's counterclaims and affirmative defenses pursuant to Fed. R. Civ. P. 12(B)(6) and 12(F)" before the United States District Court Southern District of California (*DNA Genotek Inc.v. Spectrum Solutions L.L.C.*, Case No. 21-cv-0516-JO-AGS), dated Feb. 1, 2022, is a copy of an Information Disclosure Statement filed by DNA Genotek in the 765 application. (Doc. No. 78-4).
"Exhibit 4 to the Declaration of Brian M. Kramer in support of reply in support of DNA Genotek Inc.'s motion to dismiss and strike defendant Spectrum Solutions LLC's counterclaims and affirmative defenses pursuant to Fed. R. Civ. P. 12(B)(6) and 12(F)" before the United States District Court Southern District of California (*DNA Genotek Inc.v. Spectrum Solutions L.L.C.*, Case No. 21-cv-0516-JO-AGS), dated Feb. 1, 2022, is a copy of the Notice of Allowability of the 765 application. (Doc. No. 78-5).
"Spectrum's Invalidity Contentions Under PLR 3.3 and Accompanying Document Production Under PLR 3.4", before the United States District Court Southern District of California (*DNA Genotek Inc.v. Spectrum Solutions L.L.C.*, Case No. 3:21-cv-00516-DMS-LL), dated Nov. 19, 2021.
Appendix A: Invalidity Claim Chart for U.S. Pat. No. 10,619,187, Fischetti—U.S. Pat. No. 5,643,767 from "Spectrum's Invalidity Contentions under PLR 3.3 and accompanying document production under PLR 3.4" before the United States District Court Southern District of California (*DNA Genotek Inc.v. Spectrum Solutions L.L.C.*, Case No. 3:21-cv-00516-DMS-LL), dated Nov. 19, 2021.
Appendix B: Invalidity Claim Chart for U.S. Pat. No. 10,619,187, Soane—PCT Publication No. WO00/10884 from "Spectrum's Invalidity Contentions under PLR 3.3 and accompanying document production under PLR 3.4" before the United States District Court Southern District of California (*DNA Genotek Inc.v. Spectrum Solutions L.L.C.*, Case No. 3:21-cv-00516-DMS-LL), dated Nov. 19, 2021.
Appendix C: Invalidity Claim Chart for U.S. Pat. No. 10,619,187, Moscovitz 113—U.S. Pat. No. 6,533,113 from "Spectrum's Invalidity Contentions under PLR 3.3 and accompanying document production under PLR 3.4" before the United States District Court Southern District of California (*DNA Genotek Inc.v. Spectrum Solutions L.L.C.*, Case No. 3:21-cv-00516-DMS-LL), dated Nov. 19, 2021.
Appendix D: Invalidity Claim Chart for U.S. Pat. No. 10,619,187, Moscovitz 110—U.S. Pat. No. 6,527,110 from "Spectrum's Invalidity Contentions under PLR 3.3 and accompanying document production under PLR 3.4" before the United States District Court Southern District of California (*DNA Genotek Inc.v. Spectrum Solutions L.L.C.*, Case No. 3:21-cv-00516-DMS-LL), dated Nov. 19, 2021.
Appendix E: Invalidity Claim Chart for U.S. Pat. No. 10,619,187, Okauchi—PCT Publication No. WO98/03265 from "Spectrum's Invalidity Contentions under PLR 3.3 and accompanying document production under PLR 3.4" before the United States District Court Southern District of California (*DNA Genotek Inc.v. Spectrum Solutions L.L.C.*, Case No. 3:21-cv-00516-DMS-LL), dated Nov. 19, 2021.
Appendix F: Invalidity Claim Chart for U.S. Pat. No. 10,619,187, Finke—U.S. Pat. No. 4,591,050 from "Spectrum's Invalidity Contentions under PLR 3.3 and accompanying document production under PLR 3.4" before the United States District Court Southern District of California (*DNA Genotek Inc.v. Spectrum Solutions L.L.C.*, Case No. 3:21-cv-00516-DMS-LL), dated Nov. 19, 2021.
Appendix G: Invalidity Claim Chart for U.S. Pat. No. 10,619,187, Guirguis - PCT Publication No. WO 98/038,917 from "Spectrum's Invalidity Contentions under PLR 3.3 and accompanying document production under PLR 3.4" before the United States District Court Southern District of California (*DNA Genotek Inc.v. Spectrum Solutions L.L.C.*, Case No. 3:21-cv-00516-DMS-LL), dated Nov. 19, 2021.
Appendix H: Claim Chart for U.S. Pat. No. 11,002,646, U.S. Patent Pub. No. 2009/0216213 ("Muir"), WO 2005/051775 ("Cho"), U.S. Pat. No. 5,967,309 (Robles-Gonzalez), U.S. 2009/0133366 ("Cronin") from "Spectrum's Invalidity Contentions under PLR 3.3 and accompanying document production under PLR 3.4" before the United States District Court Southern District of California (*DNA Genotek Inc.v. Spectrum Solutions L.L.C.*, Case No. 3:21-cv-00516-DMS-LL), dated Nov. 19, 2021.
Appendix I: Invalidity Claim Chart for U.S. Pat. No. 11,002,646, U.S. Patent Pub. No. 2012/0325721 ("Plante"), WO 2005/051775 ("Cho"), U.S. Pat. No. 5,967,309 ("Robles-Gonzalez"), U.S. Patent Pub. No. 2009/0133366 ("Cronin") from "Spectrum's Invalidity Contentions under PLR 3.3 and accompanying document production under PLR 3.4" before the United States District Court Southern District of California (*DNA Genotek Inc.v. Spectrum Solutions L.L.C.*, Case No. 3:21-cv-00516-DMS-LL), dated Nov. 19, 2021.

(56) References Cited

OTHER PUBLICATIONS

Appendix J: Claim Chart for U.S. Pat. No. 11,002,646, U.S. Patent Pub. No. 2004/0161788 ("Chen"), WO 2005/051775 ("Cho"), U.S. Pat. No. 5,967,309 ("Robles-Gonzalez"), U.S. Patent Pub. No. 2009/0133366 ("Cronin") from "Spectrum's Invalidity Contentions under PLR 3.3 and accompanying document production under PLR 3.4" before the United States District Court Southern District of California (*DNA Genotek Inc.*v. *Spectrum Solutions L.L.C.*, Case No. 3:21-cv-00516-DMS-LL), dated Nov. 19, 2021.
Appendix K: Invalidity Claim Chart for U.S. Pat. No. 11,002,646, U.S. 2008/0293156 ("Smith"), WO 2005/051775 ("Cho"), U.S. Pat. No. 5,967,309 ("Robles-Gonzalez"), U.S. Patent Pub. No. 2009/0133366 ("Cronin") from "Spectrum's Invalidity Contentions under PLR 3.3 and accompanying document production under PLR 3.4" before the United States District Court Southern District of California (*DNA Genotek Inc.*v. *Spectrum Solutions L.L.C.*, Case No. 3:21-cv-00516-DMS-LL), dated Nov. 19, 2021.
Spectrum Solutions, LLC's Opening Claim Construction Brief before the United States District Court Southern District of California (*DNA Genotek Inc.*v. *Spectrum Solutions L.L.C.*, Case No. 21-CV-0516-JO-AGS), dated Feb. 18, 2022. (Doc. No. 83).
Declaration of Ali S. Razai in Support of Spectrum Solution LLC's Opening Claim Construction Brief before the United States District Court Southern District of California (*DNA Genotek Inc.*v. *Spectrum Solutions L.L.C.*, Case No. 21-cv-0516-JO-AGS), dated Feb. 18, 2022. (Doc. No. 83-1).
Declaration of Vincent A. Fischetti, Ph.D. before the United States District Court Southern District of California (*DNA Genotek Inc.*v. *Spectrum Solutions L.L.C.*, Case No. 21-CV-0516-JO-AGS), dated Feb. 19, 2022. (Doc. No. 87).
Defendant Spectrum Solutions, L.L.C.'s Responsive Claim Construction Brief before the United States District Court Southern District of California (*DNA Genotek Inc.*v. *Spectrum Solutions L.L.C.*, Case No. 21-CV-0516-JO-AGS), dated Mar. 4, 2022. (Doc. No. 88).
Plaintiff DNA Genotek Inc.'s Responsive Claim Construction Brief before the United States District Court Southern District of California (*DNA Genotek Inc.*v. *Spectrum Solutions L.L.C.*, Case No. 21-CV-0516-JO-AGS), dated Mar. 4, 2022. (Doc. No. 89).
Notice of Errata and Declaration of Vincent A. Fischetti, Ph.D. before the United States District Court Southern District of California (*DNA Genotek Inc.*v. *Spectrum Solutions L.L.C.*, Case No. 21-CV-0516-JO-AGS), dated Mar. 21, 2022. (Doc. No. 100).
Order Denying Plaintiff/Counter Defendant's Motion to Dismiss Counterclaims and Denying Motion to Strike Without Prejudice before the United States District Court Southern District of California (*DNA Genotek Inc.*v. *Spectrum Solutions L.L.C.*, Case No. 21-CV-0516-JO-AGS), dated Apr. 1, 2022. (Doc. No. 111).
DNA Genotek Inc.'s Answer to Spectrum Solutions L.L.C.'s Counterclaims before the United States District Court Southern District of California (*DNA Genotek Inc.*v. *Spectrum Solutions L.L.C.*, Case No. 21-CV-0516-JO-AGS), dated Apr. 13, 2022. (Doc. No. 115).
DNA Genotek Inc.'s Notice of Errata to Opening Claim Construction Brief before the United States District Court Southern District of California (*DNA Genotek Inc.*v. *Spectrum Solutions L.L.C.*, Case No. 21-CV-0516-JO-AGS), dated Jul. 18, 2022. (Doc. No. 132).
DNA Genotek Inc.'s Corrected Opening Claim Construction Brief before the United States District Court Southern District of California (*DNA Genotek Inc.*v. *Spectrum Solutions L.L.C.*, Case No. 21-CV-0516-JO-AGS), dated Jul. 19, 2022. (Doc. No. 134).
Petition for Inter Partes Review of U.S. Pat. No. 10,000,795 between Applicant and Spectrum Solutions L.L.C. before the Patent Trial and Appeal Board (*Spectrum Solutions L.L.C.*, v. *DNA Genotek Inc.*, IPR2022-00774 Patent 10,000,795), filed Mar. 28, 2022.
Exhibit No. 1004: German Patent No. DE 10219117 to Stefan et al., issued Oct. 30, 2003, submitted with Petition for Inter Partes Review of U.S. Pat. No. 10,000,795 between Applicant and Spectrum Solutions L.L.C. before the Patent Trial and Appeal Board (*Spectrum Solutions L.L.C.*, v. *DNA Genotek Inc.*, IPR2022-00774 Patent 10,000,795), filed Mar. 28, 2022.
Exhibit No. 1005: Certified English Translation of German Patent No. DE10219117 C1 to Stefan et al., issued Oct. 30, 2003, including translation affidavit, submitted with Petition for Inter Partes Review of U.S. Pat. No. 10,000,795 between Applicant and Spectrum Solutions L.L.C. before the Patent Trial and Appeal Board (*Spectrum Solutions L.L.C.*, v. *DNA Genotek Inc.*, IPR2022-00774 Patent 10,000,795), filed Mar. 28, 2022.
Exhibit No. 1006: U.S. Patent Publication No. 2003/0104424 to Tuggle et al., published Jun. 5, 2003, submitted with Petition for Inter Partes Review of U.S. Pat. No. 10,000,795 between Applicant and Spectrum Solutions L.L.C. before the Patent Trial and Appeal Board (*Spectrum Solutions L.L.C.*, v. *DNA Genotek Inc.*, IPR2022-00774 Patent 10,000,795), filed Mar. 28, 2022.
Exhibit No. 1007: Noll et al., "The Use of Sodium and Lithium Dodecyl Sulfate in Nucleic Acid Isolation", 12 Methods in Enzymology, 1968, 129-155, submitted with Petition for Inter Partes Review of U.S. Pat. No. 10,000,795 between Applicant and Spectrum Solutions L.L.C. before the Patent Trial and Appeal Board (*Spectrum Solutions L.L.C.*, v. *DNA Genotek Inc.*, IPR2022-00774 Patent 10,000,795), filed Mar. 28, 2022.
Exhibit No. 1009: U.S. Pat. No. 5,973,137 to Heath, issued Oct. 26, 1999, submitted with Petition for Inter Partes Review of U.S. Pat. No. 10,000,795 between Applicant and Spectrum Solutions L.L.C. before the Patent Trial and Appeal Board (*Spectrum Solutions L.L.C.*, v. *DNA Genotek Inc.*, IPR2022-00774 Patent 10,000,795), filed Mar. 28, 2022.
Exhibit No. 1010: Cunningham et al., "Mutation Detection in Colorectal Cancers: Direct Sequencing of DNA Mismatch Repair Genes", Colorectal Cancer: Methods and Protocols, 2001, Chapter 10, pp. 87-98, submitted with Petition for Inter Partes Review of U.S. Pat. No. 10,000,795 between Applicant and Spectrum Solutions L.L.C. before the Patent Trial and Appeal Board (*Spectrum Solutions L.L.C.*, v. *DNA Genotek Inc.*, IPR2022-00774 Patent 10,000,795), filed Mar. 28, 2022.
Exhibit No. 1025: Quinn, "Sample Preparation for Nucleic Acid Amplification", Nucleic Acid Amplification Technologies: Application to Disease Diagnosis, 1997, Chapter 4, pp. 49-60, submitted with Petition for Inter Partes Review of U.S. Pat. No. 10,000,795 between Applicant and Spectrum Solutions L.L.C. before the Patent Trial and Appeal Board (*Spectrum Solutions L.L.C.*, v. *DNA Genotek Inc.*, IPR2022-00774 Patent 10,000,795), filed Mar. 28, 2022.
Freeman et al., DNA by Mail: An Inexpensive and Noninvasive Method for Collecting DNA Samples from Widely Dispersed Populations, Behavior Genetics, 27:3 (1997).
Goldenberger, et al., A Simple "Universal" DNA Extraction Procedure Using SDS and Proteinase K is Compatible with Direct PCR Amplification, Technical Tips, 4:368-370 (1995).
Streckfus, et al., Saliva as a Diagnostic Fluid, Oral Diseases, 8:3:69-76 (2002).
Tabak, A Revolution in Biomedical Assessment: The Development of Salivary Diagnostics, Journal of Dental Education, 65:1336-1339 (Dec. 2001).
Inter Partes Review between Applicant and Spectrum Solutions L.L.C. before the Patent Trial and Appeal Board (*Spectrum Solutions L.L.C.*, v. *DNA Genotek Inc.*, IPR2022-00134 Patent 10,767,215), filed Nov. 2, 2021.
Exhibit No. 1004: German Patent No. DE 10219117 to Stefan et al., issued Oct. 30, 2003, submitted with Petition for Inter Partes Review of U.S. Pat. No. 10,000,795 between Applicant and Spectrum Solutions L.L.C. before the Patent Trial and Appeal Board (*Spectrum Solutions L.L.C.*, v. *DNA Genotek Inc.*, IPR2022-00134 Patent 10,767,215), filed Nov. 2, 2021.
Exhibit No. 1005: Certified English Translation of German Patent No. DE10219117 C1 to Stefan et al., issued Oct. 30, 2003, including translation affidavit, submitted with Inter Partes Review between Applicant and Spectrum Solutions L.L.C. before the Patent Trial and Appeal Board (*Spectrum Solutions L.L.C.*, v. *DNA Genotek Inc.*, IPR2022-00134 Patent 10,767,215), filed Nov. 2, 2021.
Exhibit No. 1006: U.S. Patent Publication No. 2003/0104424 to Tuggle et al., published Jun. 5, 2003, submitted with Inter Partes Review between Applicant and Spectrum Solutions L.L.C. before

(56) References Cited

OTHER PUBLICATIONS the Patent Trial and Appeal Board (*Spectrum Solutions L.L.C.*, v. *DNA Genotek Inc.*, IPR2022-00134 Patent 10,767,215), filed Nov. 2, 2021.
Exhibit No. 1007: Noll et al., "The Use of Sodium and Lithium Dodecyl Sulfate in Nucleic Acid Isolation", 12 Methods in Enzymology, 1968, 129-155, submitted with Inter Partes Review between Applicant and Spectrum Solutions L.L.C. before the Patent Trial and Appeal Board (*Spectrum Solutions L.L.C.*, v. *DNA Genotek Inc.*, IPR2022-00134 Patent 10,767,215), filed Nov. 2, 2021.
Exhibit No. 1009: U.S. Pat. No. 5,973,137 to Heath, issued Oct. 26, 1999, submitted with Inter Partes Review between Applicant and Spectrum Solutions L.L.C. before the Patent Trial and Appeal Board (Spectrum Solutions L.L.C, v. DNA Genotek Inc., IPR2022-00134 Patent 10,767,215), filed Nov. 2, 2021.
Exhibit No. 1010: Cunningham et al., "Mutation Detection in Colorectal Cancers: Direct Sequencing of DNA Mismatch Repair Genes", Colorectal Cancer: Methods and Protocols, 2001, Chapter 10, pp. 87-98, submitted with Inter Partes Review between Applicant and Spectrum Solutions L.L.C. before the Patent Trial and Appeal Board (*Spectrum Solutions L.L.C.*, v. *DNA Genotek Inc.*, IPR2022-00134 Patent 10,767,215), filed Nov. 2, 2021.
Exhibit No. 1025: Quinn, "Sample Preparation for Nucleic Acid Amplification", Nucleic Acid Amplification Technologies: Application to Disease Diagnosis, 1997, Chapter 4, pp. 49-60, submitted with Inter Partes Review between Applicant and Spectrum Solutions L.L.C. before the Patent Trial and Appeal Board (*Spectrum Solutions L.L.C.*, v. *DNA Genotek Inc.*, IPR2022-00134 Patent 10,767,215), filed Nov. 2, 2021.
Patent Owner's Preliminary Response filed Mar. 15, 2022 in Inter Partes Review between Applicant and Spectrum Solutions L.L.C. before the Patent Trial and Appeal Board (*Spectrum Solutions L.L.C.*, v. *DNA Genotek Inc.*, IPR2022-00134 Patent 10,767,215).
Exhibit No. 2032: PCT International Publication No. WO 2004/033470 A2, published Apr. 22, 2004, submitted with Patent Owner's Preliminary Response filed Mar. 15, 2022 in Inter Partes Review between Applicant and Spectrum Solutions L.L.C. before the Patent Trial and Appeal Board (*Spectrum Solutions L.L.C.*, v. *DNA Genotek Inc.*, IPR2022-00134 Patent 10,767,215).
Exhibit No. 2033: PCT International Publication No. WO 2008/040126 A1, published Apr. 10, 2008, submitted with Patent Owner's Preliminary Response filed Mar. 15, 2022 in Inter Partes Review between Applicant and Spectrum Solutions L.L.C. before the Patent Trial and Appeal Board (*Spectrum Solutions L.L.C.*, v. *DNA Genotek Inc.*, IPR2022-00134 Patent 10,767,215).
Exhibit No. 2034: Eigner et al., "The thermal degradation of nucleic acids", Biochim. Biophys. Acta., Jul. 22, 1961,51: 165-168, submitted with Patent Owner's Preliminary Response filed Mar. 15, 2022 in Inter Partes Review between Applicant and Spectrum Solutions L.L.C. before the Patent Trial and Appeal Board (*Spectrum Solutions L.L.C.*, v. *DNA Genotek Inc.*, IPR2022-00134 Patent 10,767,215).
Decision dated Jun. 6, 2022 Granting Institution of Inter Partes Review in IPR2022-00134 under U.S.C. § 314 (*Spectrum Solutions L.L.C.*, v. *DNA Genotek Inc.*, IPR2022-00134 Patent 10,767,215).
Decision Granting Institution of Inter Partes Review of U.S. Pat. No. 10,000,795 between Applicant and Spectrum Solutions L.L.C. before the Patent Trial and Appeal Board (*Spectrum Solutions L.L.C.*, v. *DNA Genotek Inc.*, IPR2022-00774 Patent 10,000,795), dated Oct. 12, 2022.

Petition for Inter Partes Review of U.S. Pat. No. 11,002,646 between Applicant and Spectrum Solutions L.L.C. before the Patent Trial and Appeal Board (*Spectrum Solutions L.L.C.*, v. *DNA Genotek Inc.*, IPR2022-01347 Patent 11,002,646), filed Jul. 29, 2022.
Exhibit No. 1002: Declaration of Karl R. Leinsing, MSME, PE, submitted with Petition for Inter Partes Review of U.S. Pat. No. 11,002,646 between Applicant and Spectrum Solutions L.L.C. before the Patent Trial and Appeal Board (*Spectrum Solutions L.L.C.*, v. *DNA Genotek Inc.*, IPR2022-01347 Patent 11,002,646), filed Jul. 29, 2022.
Exhibit No. 1003: U.S. Patent Pub. No. US 2012/0325721 published Dec. 27, 2012, to Plante, et al., submitted with Petition for Inter Partes Review of U.S. Pat. No. 11,002,646 between Applicant and Spectrum Solutions L.L.C. before the Patent Trial and Appeal Board (*Spectrum Solutions L.L.C.*, v. *DNA Genotek Inc.*, IPR2022-01347 Patent 11,002,646), filed Jul. 29, 2022.
Exhibit No. 1004: International Patent Publication No. WO 2005/051775 published Jun. 9, 2005, to Cho, submitted with Petition for Inter Partes Review of U.S. Pat. No. 11,002,646 between Applicant and Spectrum Solutions L.L.C. before the Patent Trial and Appeal Board (*Spectrum Solutions L.L.C.*, v. *DNA Genotek Inc.*, IPR2022-01347 Patent 11,002,646), filed Jul. 29, 2022.
Exhibit No. 1005: U.S. Pat. No. 7,464,811 granted Dec. 16, 2008, to Patterson, et al., submitted with Petition for Inter Partes Review of U.S. Pat. No. 11,002,646 between Applicant and Spectrum Solutions L.L.C. before the Patent Trial and Appeal Board (*Spectrum Solutions L.L.C.*, v. *DNA Genotek Inc.*, IPR2022-01347 Patent 11,002,646), filed Jul. 29, 2022.
Exhibit No. 1011: Declaration of Vincent A. Fischetti, Ph.D., submitted with Petition for Inter Partes Review of U.S. Pat. No. 11,002,646 between Applicant and Spectrum Solutions L.L.C. before the Patent Trial and Appeal Board (*Spectrum Solutions L.L.C.*, v. *DNA Genotek Inc.*, IPR2022-01347 Patent 11,002,646), filed Jul. 29, 2022.
Exhibit No. 1012: Excerpts of Prosecution History of U.S. Appl. No. 16/879,506, submitted with Petition for Inter Partes Review of U.S. Pat. No. 11,002,646 between Applicant and Spectrum Solutions L.L.C. before the Patent Trial and Appeal Board (*Spectrum Solutions L.L.C.*, v. *DNA Genotek Inc.*, IPR2022-01347 Patent 11,002,646), filed Jul. 29, 2022.
Exhibit No. 1015: "Needle Stick Safety and Prevention Act" of Nov. 6, 2000, Public Law 106-430, 114 Stat. 1901, submitted with Petition for Inter Partes Review of U.S. Pat. No. 11,002,646 between Applicant and Spectrum Solutions L.L.C. before the Patent Trial and Appeal Board (*Spectrum Solutions L.L.C.*, v. *DNA Genotek Inc.*, IPR2022-01347 Patent 11,002,646), filed Jul. 29, 2022.
Exhibit No. 1016: U.S. Patent Publication 2009/0312285 A1 published Dec. 17, 2009, to Fischer et al., submitted with Petition for Inter Partes Review of U.S. Pat. No. 11,002,646 between Applicant and Spectrum Solutions L.L.C. before the Patent Trial and Appeal Board (*Spectrum Solutions L.L.C.*, v. *DNA Genotek Inc.*, IPR2022-01347 Patent 11,002,646), filed Jul. 29, 2022.
Order: (1) Claim Construction Order; and (2) Denying as Moot Plaintiffs Motion for Leave to File a Response to Defendant's Evidentiary Objections regarding U.S. Pat. Nos. 10,000,795 and 11,002,646 between Applicant and Spectrum Solutions L.L.C. before the United States District Court, Southern District of California (*DNA Genotek Inc.v. Spectrum Solutions L.L.C.*, Case No. 3:21-CV-00516-RSH-DDL), dated Nov. 29, 2022.

\* cited by examiner

Donor #

Ascorbate anion

Ascorbate radical

Dehydroascorbic acid

COMPOSITIONS AND METHODS FOR OBTAINING NUCLEIC ACIDS FROM SPUTUM

CROSS-REFERENCE TO RELATED APPLICATION

This application is a division of U.S. patent application Ser. No. 16/809,131, filed Mar. 4, 2020, which is a continuation of U.S. patent application Ser. No. 15/345,420, filed Nov. 7, 2016, now U.S. Pat. No. 10,619,187, which is a continuation of U.S. patent application Ser. No. 14/549,344, filed Nov. 20, 2014, now U.S. Pat. No. 9,523,115, which is a continuation of U.S. patent application Ser. No. 12/338,873, filed Dec. 18, 2008, which is a continuation of U.S. patent application Ser. No. 10/455,680, filed Jun. 5, 2003, now U.S. Pat. No. 7,482,116, which claims the benefit of U.S. Provisional Patent Application Serial Nos. 60/386,397, filed Jun. 7, 2002; 60/386,398, filed Jun. 7, 2002; and 60/386,399, filed Jun. 7, 2002, each of which is hereby incorporated herein by reference in their entirety.

BACKGROUND OF THE INVENTION

The present invention relates to compositions and methods for preserving nucleic acids at room temperature for extended periods of time and for simplifying the isolation of nucleic acids.

DNA can be extracted from virtually every type of cell in the human body, with the exception of red blood cells. The usual source of bodily samples for extraction of DNA is venous blood, since the number of nucleated white blood cells (principally neutrophils and lymphocytes) is relatively high and quite consistent: the normal range is about 5 to 10 million white blood cells per milliliter of blood. The DNA content of human cells is about 6 micrograms per million cells, so 1 milliliter can theoretically yield from 30 to 60 micrograms of DNA. However, there are about 5 billion red blood cells per milliliter of blood, which, since they contain no DNA, must be removed to obtain pure DNA. Furthermore, the use of blood as a source of DNA has many other disadvantages. Collection of blood is not a trivial procedure. Taking of venous blood requires trained personnel. It is an invasive procedure, which frequently causes some distress and pain to the donor. Precautions are needed to minimize exposure of personnel to blood-borne pathogens. Once collected, the blood sample must be either frozen or quickly transported to a laboratory for extraction of DNA. For these reasons, venous blood is not the ideal source of DNA. A simpler procedure for obtaining blood is to collect a few drops after a finger prick and blotting it onto a piece of filter paper. Less training of personnel is required. Once dried, the DNA is quite stable. The amount of DNA recovered is small but sufficient for many forensic purposes. However, a finger prick is still an invasive procedure and heme derived from hemoglobin in blood can inhibit some types of DNA analysis.

Swabbing the inside of the cheek with a brush (a buccal swab) is another source of cells that contain DNA. It is much less invasive than taking of blood and can be collected by individuals with less training than is required in the collection of blood. Once collected, the time that useable DNA can be recovered can be extended by either drying the swab or wiping onto filter paper and drying it. However, as the inside of the mouth is not a sterile source (as compared to blood) and microbes can degrade the quality of the DNA after a period of time. The number of cells recovered by this procedure is not large and typically less than 1-2 micrograms of DNA can be expected in the entire sample.

Saliva is a fairly clear, colorless fluid secreted principally by the major salivary glands (parotid, submandibular, and sublingual). Its function is to lubricate and cleanse the oral cavity, as well as to initiate the process of digestion. The parotid gland primarily secretes serous (watery) saliva, while the other glands secrete a mixture of serous and mucinous (sticky) saliva. Components of saliva include albumin, globulin, mucins, and digestive enzymes. It has long been known that cellular DNA is present in saliva and that this DNA is suitable for forensic purposes. Forensic use is typically limited to victim or suspect identification, using the tiny amounts of DNA from saliva that may recovered at a crime scene or from the back of a postage stamp. The notion that saliva may be a reliable source of genomic DNA and a rival to venous blood samples for this purpose has been investigated more recently in a scientific publication (van Schie, et al., *J. Immunol. Methods* 208:91-101, 1997). The authors used freshly collected or frozen saliva samples and purified the DNA by a fairly complex extraction procedure. Estimates of the quantity of DNA recovered were based upon light absorption at 260 nm, a procedure known to be an unreliable method since other common biological macromolecules, such as RNA, have essentially the same ultraviolet light absorption spectrum. Nevertheless, these authors showed that quality genomic DNA was indeed present by gel electrophoretic analysis and polymerase chain reaction analysis for certain allelic polymorphisms. Another communication (Terasaki, et al., *Hum. Immunol.* 59:597-598, 1998) reported similar results about the suitability of saliva as a source of DNA for HLA typing by polymerase chain reaction analysis. Although the amount of DNA recovered was reported, the method used to measure DNA was not. These authors provided 3 examples where saliva dried on filter paper yielded DNA suitable for analysis.

With the increasing use of DNA-based analysis in forensics, law enforcement, military, human medicine, veterinary medicine, and research, there is a need for a product that would allow saliva to become a standard reliable source of DNA from an individual (to replace blood, the current standard). In forensic, military and mass disaster situations, for example, DNA samples are now routinely taken from living persons thought to be relatives of unidentified victims of accident or foul play, to aid in identification of the dead. Military personnel or other individuals who expect to encounter hazardous situations where their lives may be at risk may wish to store DNA samples prior to exposing themselves to these hazards. In the law enforcement area, convicted felons in both Canada and the United States are now required to provide DNA samples. DNA-based tests are expected to increase in medicine, such as testing for cystic fibrosis, cytochrome P450 isotypes, polymorphisms affecting susceptibility to infectious and autoimmune diseases, HLA typing, paternity issues, to name but a few. In clinical studies, an example would be to screen populations for colon cancer-predisposing genes or family members of a breast cancer victim for breast cancer predisposing genes. In all of these cases, there are significant advantages to providing a saliva sample rather than providing a blood sample as a source of DNA. All donors would prefer donating saliva rather than blood because of the discomfort, pain, or apprehension associated with phlebotomy or pin-pricks. Saliva has a further advantage of not requiring specialized personnel thereby reducing cost where mass sample collection is being carried out. The risk of blood-borne infection is likewise decreased.

In addition to the problem of developing a standard collection and preservation method for DNA in saliva, there remains an ongoing need to improve methods of overcoming problems specific to the recovery of nucleic acids from saliva. The problem of extraction of high molecular weight DNA and RNA from mammalian cells has been partially addressed by Birnboim in *Methods of Enzymology* 216:154-160, 1993, but this work was not extended to the recovery of nucleic acids from mucin-containing bodily fluids.

Multimeric proteins called mucins are high molecular weight glycosylated proteins that form a major part of a protective biofilm on the surface of epithelial cells, where they can provide a barrier to particulate matter and bind microorganisms. These glycoproteins contribute greatly to the viscoelastic nature of saliva. The major high-molecular-weight mucin in salivary secretions is MUC5B, one of four gel-forming mucins that exist as multimeric proteins with molecular weights greater than 20-40 million daltons. MUC5B is a large oligomeric mucin composed of disulphide-linked subunits.

It is known that reagents that reduce disulfides also reduce the viscosity of mucin, such as that found in sputum or saliva. Reducing agents, in particular sulfur-containing chemicals such as β-mercaptoethanol and dithiothreitol, are widely used in biochemistry. However, many biochemically relevant reducing agents are capable of reacting in solution with dissolved oxygen. This is known are autooxidation (also called autoxidation or auto-oxidation), where 1-electron reduction intermediates of oxygen are formed, viz., superoxide ($O_2^-$), hydrogen peroxide ($H_2O_2$) and hydroxyl radical (OH). In addition, transitional metal cations function as catalysts and $O_2^-$ has been demonstrated to be an intermediate. Unfortunately, reducing agents and reducing compositions of the prior art have a relatively short shelf life, especially in basic solutions, and stock solutions that contain reducing agents cannot be prepared and stored under ambient conditions for an extended period time, usually not more than a day or two.

Therefore, in addition to a need for a means to collect sputum or saliva, and subsequently preserving the nucleic acids contained therein by contacting them with a stabilizing composition, there is a need for the inclusion of a stable reducing agent into the composition, such that nucleic acids can be conveniently recovered from it, especially after extended periods of time in the presence of oxygen at neutral or mildly alkaline pH.

SUMMARY OF THE INVENTION

The present inventor has developed a composition, which, when mixed with a mucin-containing bodily fluid, preserves the nucleic acids at room temperature under ambient conditions for extended periods of time. There is no requirement for freezing of the samples before nucleic acid recovery and purification. The properties of this composition are that it (a) chemically stabilizes nucleic acids, (b) inhibits nucleases that may be present in the saliva, and (c) is compatible with proteolytic enzymes and other reagents used to purify/amplify oligo- or polynucleotides. A fourth and novel property of this composition is that it contains an agent that rapidly reduces the viscous properties of mucin, greatly facilitating the extraction of nucleic acids contained within.

Accordingly, a first aspect of the invention features a composition for preserving nucleic acids that includes a chelating agent, and a denaturing agent, where the pH of the composition is greater than 5.0. In one embodiment, the composition is an aqueous solution.

In another embodiment, the composition also includes a reducing agent. For example, it can include one or more of the following: ascorbic acid, dithionite, erythiorbate, N-acetylcysteine, cysteine, glutathione, dithiothreitol, 2-mercaptoethanol, dierythritol, a resin-supported thiol, a resin-supported phosphine, vitamin E, and trolox, or salts thereof. Desirably, the reducing agent is ascorbic acid, erythiorbate, N-acetylcysteine, dithiothreitol, or 2-mercaptoethanol, and most desirably, the reducing agent is ascorbic acid. In another embodiment, the composition does not contain ascorbic acid. In yet another embodiment, the concentration of the reducing agent in the composition is greater than or equal to 50 millimolar.

Antioxidant free-radical scavengers are also desirable reducing agents for the composition of the present invention. Examples include antioxidant vitamins, antioxidant hormones, antioxidant enzymes, thiols, and phenols.

Desirably, the reducing agent retains reducing activity for at least 46 days in the presence of one or more of the following: oxygen, ambient air, ambient light, and alkaline pH.

The chelating agent of the composition can be selected from the group consisting of: ethylenediamine tetraacetic acid (EDTA), cyclohexane diaminetetraacetate (CDTA), diethylenetriamine pentaacetic acid (DTPA), tetraazacyclododecanetetraacetic acid (DOTA), tetraazacyclotetradecanetetraacetic acid (TETA), and desferrioximine, or chelator analogs thereof. Desirably, the chelating agent is cyclohexane diaminetetraacetate (CDTA), diethylenetriamine pentaacetic acid (DTPA), tetraazacyclododecanetetraacetic acid (DOTA), or desferrioximine, and most desirably, the chelating agent is cyclohexane diaminetetraacetate (CDTA).

In another embodiment, the chelating agent of the composition inhibits metal redox cycling. By "inhibits metal redox cycling" is meant the inhibition of metal-based oxidation/reduction cycles that produce reactive oxygen free-radical species. Examples of redox ion pairs involved in such cycles include $Fe^{2+}/Fe^{3+}$, $Cu^{1+}/Cu^{2+}$, and various oxidation states of molybdenum, vanadium, nickel, and cobalt. Chelators that bind one or both ions of a redox ion pair can inhibit the production of reactive oxygen species such as, for example, hydroxyl radical (HO), hydroperoxyl radical (HOO), superoxide radical ($O_2^-$), nitric oxide radical (NO), or peroxynitrite radical ($ONO_2^-$).

The nucleic acid to be preserved by the composition can be DNA or RNA, including mRNA or viral RNA.

The pH of the composition can between from about 5.0 and about 11.0, desirably from about 6.5 to about 7.5, and most desirably, about 7.0. For the preservation of DNA, a pH from about 7.0 to about 10.0 can be used. Depending on other components of the compositions, desirable pHs are about 7.5, about 8.0, or a pH range from about 8.0 to about 9.0. A buffer, such as HEPES, TRIS, or carbonate buffer can be added to the composition to maintain the pH in a constant range. For the preservation of RNA, a pH from about 5.0 to about 7.0, desirably from about 6.5 to about 6.8 can be used. Again, a buffer, such as BES, can be used to maintain the pH in a constant range.

The denaturing agent of the composition can be selected from the group consisting of: urea, dodecyl sulfate, guanidinium chloride, guanidinium thiocyanate, perchlorate, and an alcohol. Desirably, the denaturing agent is urea, dodecyl sulfate, or an alcohol, wherein the alcohol is 10%-60% of the total composition volume. The alcohols can be methanol, ethanol, n-propanol, isopropanol, n-butanol, trifluoroethanol, phenol, or 2,6-di-tert-butyl-4-methylphenol.

In another embodiment, the composition includes an antimicrobial agent. By "antimicrobial agent" is meant a substance or group of substances which reduces the rate of growth of an organism compared to the rate of growth of the organism in their absence. A reduction in the rate of growth of an organism may be by at least 5%, more desirably, by at least 10%, even more desirably, by at least 20%, 50%, or 75%, and most desirably, by 90% or more. The definition also extends to substances which affect the viability, virulence, or pathogenicity of an organism. An antimicrobial agent can be natural (e.g., derived from bacteria), synthetic, or recombinant. An antimicrobial agent can be bacteriostatic, bactericidal or both. An antimicrobial agent is bacteriostatic if it inhibits cell division without affecting the viability of the inhibited cell. An antimicrobial agent is bactericidal if it causes cell death. Cell death is commonly detected by the absence of cell growth in liquid growth medium (e.g., absence of turbidity) or on a solid surface (e.g., absence of colony formation on agar). Those of skill in the art know that a substance or group of substances which is bacteriostatic at a given concentration may be bactericidal at a higher concentration. Certain bacteriostatic substances are not bactericidal at any concentration. Desirably, the composition of the invention includes an alcohol as an antimicrobial agent, and most desirably the composition includes ethanol.

In another embodiment, the composition also includes an inhibitor of ribonuclease. Desirable inhibitors are selected from the group consisting of: heparin, heparan sulfate, oligo(vinylsulfonic acid), poly(vinylsulfonic acid), oligo(vinylphosphonic acid), and poly(vinylsulfuric acid), or salts thereof. The inclusion of an inhibitor of ribonuclease in the composition of the invention is particularly desirable when the nucleic acid to be preserved is RNA, desirably mRNA, or when the nucleic acid to be preserved is from a virus or a bacterium.

A second aspect of the invention features a method of reducing the viscosity of a mucin-containing bodily fluid or tissue by reducing disulfide bonds inherent to mucin, wherein the bodily fluid or tissue is mixed with a composition of the invention that includes a reducing agent. In one embodiment, the bodily fluid is sputum, desirably saliva. By "sputum" is meant that mucoid matter contained in or discharged from the nasal or buccal cavity of an animal, including saliva and discharges from the respiratory passages, including the lungs. In another embodiment, the method includes the recovery of a nucleic acid.

A third aspect of the invention features a method of preserving a nucleic acid contained in sputum that includes the steps of obtaining sputum from a subject, and contacting the sputum with a composition of the invention, thus preserving the nucleic acid.

In one embodiment, when the nucleic acid is DNA, the DNA is stable for more than 14 days, desirably more than 30 days, and more desirably more than 60 days. In another embodiment, when the nucleic acid is DNA and the composition does not contain ascorbic acid, the DNA is stable for more than 60 days, and desirably more than 360 days.

A fourth aspect of the invention features a method of recovering a nucleic acid from sputum that includes the steps of: i) obtaining sputum from a subject, ii) contacting the sputum with a composition of the invention to form a mixture, iii) contacting the mixture with a protease, and iv) recovering the nucleic acid from the mixture. Desirably, the protease is proteinase K or pronase.

In one embodiment of any of the second, third, or fourth aspects, the sputum is saliva. In another embodiment, the sputum is from a mammal, desirably a human. In yet another embodiment, the nucleic acid is DNA or RNA. If the nucleic acid is RNA, desirably it is mRNA or viral RNA. The nucleic acid can be from a source foreign to the subject from which the sputum sample is taken. For example, the nucleic acid can be from a bacterium or a virus that is residing in the buccal, nasal, or respiratory passages of the subject.

In a fifth aspect, the invention features a method of preserving and/or recovering a nucleic acid from a bodily fluid that includes, placing the bodily fluid into a first region of a container, placing a composition of the invention into a second region of the container, which is separated from the first region by a barrier, closing the container, and disturbing the integrity of the barrier such that the composition and the bodily fluid are brought into contact.

In one embodiment, the disestablishment of the barrier is coupled to the closing of the container when a lid is placed on it. In one example, the barrier is punctured. In a desirable example, the barrier is in the form of a pivoting sealing disc. In this example, attachment of the lid to the container forces the disc to pivot from its original position of spanning the space between the first region and the second region to a position in which both regions are exposed to each other, thereby forming a mixture between a composition of the invention and the bodily fluid is allowed. Desirably, the bodily fluid is sputum, and most desirably, saliva.

In a sixth aspect, the invention features a device for preserving and/or isolating a nucleic acid obtained from a biological sample. The device includes: a container that has a first region for collecting a biological sample and a second region containing a composition for preserving a nucleic acid, a barrier between the first region the second region that keeps the biological sample and the composition separate, a means for closing the container, and a means for disturbing the integrity of the barrier such that the composition is capable of contacting the biological sample. The first region can have an opening of from 2.0 to 7.0 cm, desirably from 2.5 to 3.5 cm, and most desirably 3.0 cm. Desirably, the biological sample is sputum, and most desirably, saliva.

In one embodiment of the sixth aspect, the nucleic acid-preserving composition is a composition of the present invention. In another embodiment, the means for closing the container is coupled to the means for disturbing the integrity of the barrier. In yet another embodiment, the means for closing the container is an airtight lid.

In a seventh aspect, the invention features a method of manufacturing a device for preserving a nucleic acid in a biological sample that includes: providing a container that has a first region and a second region, with the first region suitable for containing a composition of the invention and the second region having an opening suitable for the application of a biological sample; placing the composition into the first region; and applying a barrier to the container between the first region and the second region, with the barrier being impermeable to the composition and capable of being disestablished.

In an embodiment of either the sixth or seventh aspect, the barrier can be a pivoting disc, where in a first position, the disc spans the compartment and separates the first and second areas. Pivoting the disc to a second position (e.g., by connecting a screw-on lid to a plunger mechanism which contacts the disc, causing it to pivot when the lid is screwed on) disestablishes the barrier and allows the biological sample contained in the first region to contact the composition that is contained in the second region.

By "about" is meant +/−10% of the stated value or a chemical or obvious equivalent thereof.

By "alcohol" is meant a water-miscible organic compound containing a hydroxyl group, including water-miscible mixtures of hydroxyl-containing organic compounds.

By "antioxidant free-radical scavenger" is meant a substance that reduces a reactive oxygen free radical species. Such free radicals include, for example, hydroxyl radical (HO), hydroperoxyl radical (HOO), superoxide radical ($O_2^-$), nitric oxide radical (NO), or peroxynitrite radical ($ONO_2^-$).

By "aqueous solution" is meant a solution or suspension that contains 30% or more water by volume.

By "bodily fluid" is meant a naturally occurring fluid from an animal, such as saliva, serum, plasma, blood, urine, mucus, gastric juices, pancreatic juices, semen, products of lactation or menstration, tears, or lymph.

By "biological sample" is meant any sample containing nucleic acids that has been obtained from or deposited by an animal. Non-limiting examples include skin, hair, bodily fluids, fecal matter, and tissue.

By "chelator analog" is meant a derivative chelator compound with the same backbone structure and having the same general properties as the parent chelator compound.

By "denaturing agent" is meant a substance that alters the natural state of that to which it is added.

By "mucin" is meant any mucoprotein that raises the viscosity of the medium surrounding the cells that secrete it.

By "mucoid" is meant any bodily fluid containing mucin

By "nucleic acid" is meant a chain of the nucleotides, including deoxyribonucleic acid (DNA) or ribonucleic acid (RNA), typically found in chromosomes, mitochodria, ribosomes, bacteria, or viruses.

By "nucleic acid-preserving composition" is meant any composition of the present invention, unless otherwise specified.

When referring to a nucleic acid, by "stable" is meant that at least about 50% of the initial amount of high molecular weight nucleic acid (DNA, RNA, mRNA, or viral RNA) contained in a sample is still present after storing the sample at ambient temperature (i.e., 20° C. to 25° C.) for the specified time period. The amount of high molecular weight DNA in a sample can quantified by densitometry analysis of the high molecular weight DNA band from an agarose gel (see FIG. 1 and Example 4).

By "resin-supported phosphine" is meant a polymer that contains a multiplicity of covalently-bound phosphine groups.

By "resin-supported thiol" is meant is meant a polymer that contains a multiplicity of covalently-bound sulfhydryl groups.

By "saliva" is meant the secretion, or combination of secretions, from any of the salivary glands, including the parotid, submaxillary, and sublingual glands, optionally mixed with the secretion from the buccal glands.

By "sputum" is meant that mucoid matter contained in or discharged from the nasal or buccal cavity of a mammal, including saliva and discharges from the respiratory passages, including the lungs.

By "subject" is meant any animal. Desirably, the subject is a mammal that can produce saliva for the purposes of nucleic acid extraction. Most desirably, the subject is a human.

Other features and advantages of the present invention will become apparent from the following detailed description. It should be understood, however, that the detailed description and the specific examples, while indicating preferred embodiments of the invention are given by way of illustration only, since various changes and modifications within the spirit and scope of the invention will become apparent to those skilled in the art from this detailed description.

DETAILED DESCRIPTION

Figure 1:
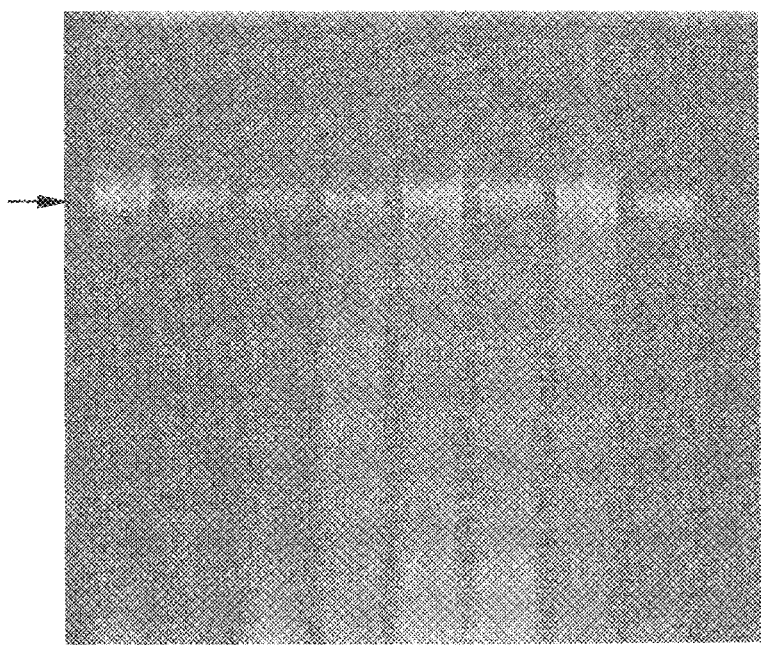
FIG. 1 is an electrophoresis agarose analysis of DNA isolated from saliva using the capacity of methods of one embodiment of the invention.

The following standard abbreviations are used herein: DNA, deoxyribonucleic acid; RNA, ribonucleic acid; mRNA, messenger RNA; HEPES, 4-(2-hydroxyethyl)-1-piperazineethanesulfonic acid; BES, N,N-bis[2-hydroxyethyl]-2-aminoethane-sulfonic acid; TRIS, tris(hydroxymethyl)aminomethane, CDTA, cyclohexane diaminetetraacetate; DTPA, N,N-bis(2-(bis(carboxymethyl)amino)ethyl)glycine; DOTA, 1,4,7,10-tetrazacyclododecanetetraacetic acid; and TETA, 1,4,8,11-tetraazacyclotetradecanetetraacetic acid.

Compositions of the Invention

The present inventors have developed compositions that render sputum as a viable option to the use of blood as a source of nucleic acids. The compositions provide the advantageous properties of chemical stabilization of nucleic acids and the inhibition of nucleases, including deoxyribonucleases, and microbial growth. Chemical stabilization of the nucleic acids in a saliva sample is achieved through the use of buffers to maintain an appropriate pH, as well as the use of chelating agents to prevent the phenomenon of metal redox cycling or the binding of metal ions to the phosphate backbone of nucleic acids. The chelating agents of the invention also participate in the inhibition of deoxyribonucleases and microbial growth, which can be additionally inhibited by the inclusion of denaturing agents and/or other suitable antimicrobial substances, such as ethanol, into the compositions of the invention. The compositions of the invention can also include one or more reducing agents, which can reduce sample viscosity, thereby making nucleic acid recovery an easier process.

Accordingly, the present invention features a composition for preserving and/or recovering nucleic acids from sputum, desirably saliva, that includes one or more chelators and one or more denaturing agents, wherein the pH of the composition is greater than 5, desirably within a pH range of about 6 to about 11, more desirably within a pH range of about 7.5 to about 10.0, and most desirably, within a pH of about 7.0.

The chemical backbone and the purine bases of DNA are most stable at slightly alkaline pH, with an optimal stability generally recognized as being within a pH range of about 7-11, and desirably a pH of about 8. Below a pH of about 6, depurination (i.e., spontaneous loss of purine bases from the deoxyribose-phosphate backbone) can occur. Above a pH of about 10, spontaneous loss of amino groups from cytosine nucleotides may occur, thereby converting cytosine to uracil. Above a pH of about 12, DNA is denatured, converting it from the double-strand form to the single-strand form. In contrast, RNA is most stable in the pH range of 5.0 to 7.0, desirably a pH of from 6.5 to 6.8. Accordingly, the pH of the composition may be adjusted using pH buffers, desirably those that best control the pH within the range of about 5 to about 11. Examples of pH buffers with desirable properties include, but not limited to, TRIS hydrochloride, HEPES and BES.

DNA has a strong affinity for metal ions, some of which, such as the common transition metals iron or copper, can catalyze the formation of reactive oxygen species. Therefore, a composition of the invention includes one or more chelators that can form complexes with metal ions to prevent them from binding to DNA, remove metal ions that that have already bound to DNA, or bind to metal ions (e.g., Fe(II)/Fe(III) or Cu(I)/Cu(II)) strongly enough to inhibit their redox cycling, and hence, the formation of reactive oxygen species. EDTA, a commonly used chelator in biological reagents, can be of some use for either of these purposes. More desirable are stronger chelators (i.e., chelators with a higher dissociation constant than EDTA when bound to a metal), used alone or in combination, that include, but are not limited to, CDTA, DTPA, DOTA, TETA, and desferioximine, or chelator analogs thereof. The amount or concentration of chelator will depend upon the strength of the chelator, which would need to be determined empirically. For CDTA, concentrations in the 1-20 mM range are sufficient, however other concentrations would work, and the compositions of the invention are not intending to be limited to this range.

Deoxyribonucleases and ribonucleases are enzymes that breakdown DNA or RNA, respectively. Their main source in the digestive tract is secretions of the pancreas, although lower levels may be present in cells of the salivary gland and buccal mucosa. In addition, microorganisms resident in the mouth or from recently ingested foods may contain deoxyribonucleases or ribonucleases. Pancreatic deoxyribonuclease is known to require divalent metal ions such as Mg(II), Mn(II) and/or Ca(II) for enzymatic activity. The strong chelators described above, in addition to providing chemical stability to the nucleic acids, will inhibit this class of metal ion-requiring deoxyribonucleases. The action of deoxyribonucleases and ribonucleases can also be inhibited by denaturing agents that will destroy the complex structures of these enzymes (proteins). Hence, denaturing agents are included in the nucleic acid preserving composition of the invention. Examples of denaturing agents that may be used (alone or in combination) include, but not limited to, urea, soluble salts of dodecyl sulfate and other strong detergents, guanidinium chloride, guanidinium thiocyanate, soluble salts of perchlorate, alcohols, such as ethanol, above 10%. Other reagents, such as heparin, heparan sulfate, or oligo (vinylsulfonic acid) (Smith, et al., *J. Biol. Chem.* Mar. 20, 2003; [epub ahead of print]) are known to inhibit the action of deoxynucleases and/or ribonucleases.

Low specificity proteases such as proteinase K are frequently used in the purification of nucleic acids. Since proteases are themselves proteins, their action can be inhibited by denaturing agents. Thus, a balance must be struck between the concentration of denaturing agents that will, on the one hand, inhibit deoxyribonucleases or ribonucleases and denature other proteins in saliva and, on the other hand, not significantly inhibit the proteolytic enzymes. At later stages in DNA purification, the DNA is often concentrated by precipitation with alcohol. Thus, salts, buffers, chelators and other components of the nucleic acid preserving/recovery solution must be chosen so as not to precipitate when concentrations of alcohol over 50% are added to precipitate the DNA.

The viscosity of sputum and saliva depends upon the presence of very high molecular weight glycoproteins complexes called mucins, particular the gel-forming mucins (Offner, et al., *Adv. Dent. Res.* 14:69-75, 2000; Seregni, et al., *Tumori* 83:625-632, 1997). It has been found that the inclusion of a reducing agent into a composition of the invention has the effect of markedly reducing the viscosity of saliva, especially "unstimulated" saliva, thereby facilitating the recovery of nucleic acids. Accordingly, in one embodiment, a composition of the invention further includes one or more reducing agents. The reducing agents are desirably at high concentration (greater than 0.05 M). While not wishing to be limited by theory, it is presumed that the reducing agent reduces the viscosity of the saliva by breaking disulfide bonds that hold together chains of mucin, and that any reducing agent that has the appropriate redox potential to reduce disulfide bonds in proteins would be suitable. Desirably, the reducing agent is selected from the group consisting of: ascorbic acid, dithionite, erythiorbate, N-acetylcysteine, cysteine, glutathione, dithiothreitol, 2-mercaptoethanol, dierythritol, a resin-supported thiol, a resin-supported phosphine, vitamin E, and trolox, or salts thereof.

In another embodiment, a composition of the invention that includes a reducing agent maintains reducing capacity at room temperature in a sealed container in the presence of ambient oxygen, and/or in the presence of ambient light for more than a week, desirably for up to about 46 days, and most desirably for at least 46 days. This embodiment combines the nucleic acid stabilization provided by a strong chelator a denaturing agent, and a reducing agent in a composition with a pH within the range of about 6 to about 11, and desirably a pH of about 8.0.

Figure 5:
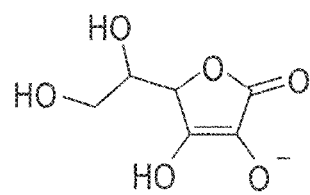
FIG. 5 shows structures of (oxidized) ascorbate anion, (reduced) dehydroascorbic acid, and a free radical intermediate
Figure 5:
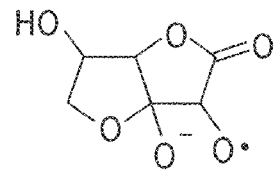
Figure 5:
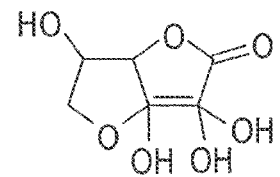
Figure 6:
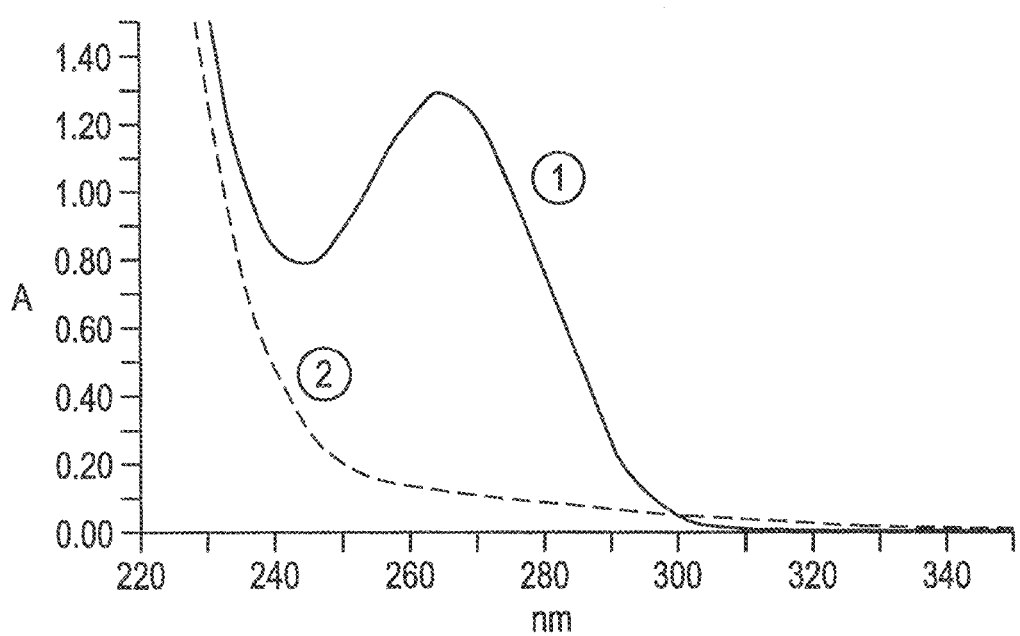
FIG. 6 is a compilation of two spectrophotometric scans of sodium ascorbate (100 µM) in CB (1 mM CDTA, 10 mM BES, pH 7.4), prepared under aerobic conditions over 30 minutes at room temperature (scan 1) and 3 minutes after addition of a few crystals of $MnCl_2$.(scan 2), as per Example 8.

A particularly desirable reducing agent is sodium ascorbate. As well as an important dietary antioxidant micronutrient, ascorbic acid (vitamin C) is a non-thiol reducing agent and is inexpensive, non-toxic, and stable in the presence of the chelators and denaturing agents that are included in the compositions of the invention. The structures of (oxidized) ascorbate anion, (reduced) dehydroascorbic acid, and a free radical intermediate are shown in FIG. 5. The most thoroughly studied oxidation reaction of ascorbate is its oxidation by oxygen. As with many other reducing agents, trace amounts of transitional metals such as iron or copper can promote autooxidation (Buettner, *Free Radic. Res. Commun.* 1:349-53, 1986; Buettner and Jurkiewicz *Radiat. Res.* 145:532-41, 1996; Miller, et al., *Free Radic. Biol. Med.* 8:95-108, 1990). Metal cation-catalyzed oxidation of ascorbate can be conveniently monitored as a decrease in absorbance at 265 nm (Buettner *Free Radic. Res. Commun.* 10:5-9, 1990), as described in Example 8 and shown in FIGS. 5, 6, and 8. Certain chelating agents can appreciably slow down autooxidation of ascorbate at pH 7.0 or lower (Buettner *J. Biochem. Biophys. Methods* 16:27-40, 1988), as described in Example 10 and shown in FIG. 8.

In another embodiment, a composition of the present invention includes one or more chelators, one or more denaturing agents, and one or more antimicrobial agents, wherein the pH of the composition is within a pH range of about 6.0 to about 11.0, desirably at a pH of about 8.0. Microbial growth may also be inhibited by the strong chelators and denaturing agents, for example, ethanol, described above. Therefore, in a further embodiment of the present invention, a composition for preserving and/or recovering DNA from sputum includes one or more chelators and one or more denaturing agents, wherein at least one or more of the denaturing agents and/or chelating agents is present in amounts to act as an antimicrobial agent.

Reagents that indicate when a biological sample has been contacted with a composition of the invention can also be included as part of the composition. Desirable are those reagents that result in a visual color change of the composition solution upon mixing with the added sample. These reagents can function by reacting with any number of functional groups that are contained in biological samples, including, for example, amines, thiols, or glycosyl groups. Such colorimetric reagents are known to those skilled in the art and are chosen in such a manner that other components of the composition do not interfere with their effective usage.

Methods of the Invention

The present invention features methods of collecting, preserving, and recovering nucleic acids from sputum using a composition of the invention. The methods of the invention involve contacting a sputum sample from a subject with a composition of the invention and optionally mixing the resulting solution with a protease, such as pronase or proteinase K. Furthermore, some compositions of the invention feature a reducing agent that can facilitate the recovery of nucleic acids from composition/sample mixtures by decreasing the viscosity of these mixtures.

Accordingly, one aspect of the invention features a method of preserving a nucleic acid contained in sputum that includes the steps of obtaining sputum from a subject, and contacting the sputum with a composition of the invention, thus preserving the nucleic acid. Examples 1 and 2 describe the collection of saliva, both from subjects that can follow instructions and from those that can not.

The sputum is typically contacted with a composition of the invention upon collection or immediately after it is collected, and preferably not much later than about 1 hour after collection. This time can vary depending on storage conditions of the sputum after collection. For example, it could be indefinite if stored frozen or perhaps 1-2 days if stored at 4° C. A reducing agent can be in the preserving composition used, or added at a later time prior to nucleic acid isolation. Desirable reducing agent-containing compositions are those that are stable and retain a reducing capacity for more than a week, desirably for up to about 46 days, and most desirably for at least 46 days.

In an example (see Example 5), the results of which are presented in Table 1, saliva was collected and mixed with approximately an equal volume of a composition of the invention (see Example 3 for preparation), and analyzed for DNA content by PCR analysis at later timepoints.

TABLE 1

Estimated amounts of DNA in saliva samples*
Donor #

Stim. saliva collected on 02Feb26, analyzed 64 days by the DNase method

| 1 | 2 | 3 | 4 | 5 | 6 | 7 | 8 | 9 | 10 | 11 |
|---|---|---|---|---|---|---|---|---|----|----|
| 21.2 | 21.4 | 16.6 | 16.0 | 28.8 |  | 44.8 | 22.2 | 16.6 |  |  |

Unstim. saliva collected on 02Mar25, analyzed 15 days later by DNase method

| 1 | 2 | 3 | 4 | 5 | 6 | 7 | 8 | 9 | 10 | 11 |
|---|---|---|---|---|---|---|---|---|----|----|
|  |  | 64.2 |  |  |  | 80.6 | 24.4 |  | 27.2 | 69.0 |

*DNA content in nanograms per microliter

To collect the sputum from the subject it is preferred that the mouth be rinsed before sampling. Food particles can introduce foreign DNA and saliva transferred by kissing can be a source of foreign human DNA. The mouth can be rinsed with about 50 mL of tepid water by vigorous swishing or by brushing with a tooth brush without tooth paste. Unstimulated saliva is usually of the mucinous type and is secreted at a slow rate. Stimulated saliva (anticipation of tasty food, sweet or sour candy) is of the serous (watery) type and secreted at a faster rate. It has been found (see Table 2) that there is more DNA in 2 mL of unstimulated saliva than 2 mL of stimulated saliva. After rinsing of the mouth and waiting about two or three minutes, the donor may spit a volume (for example, about 2 mL) of "unstimulated" saliva into the receiving tube. If this proves to be difficult, saliva flow can conveniently be stimulated with a cube of table sugar, or any other such saliva-stimulatory substance that does not interfere with DNA recovery or purification.

TABLE 2

Comparison of DNA content of unstimulated and stimulated saliva

| Donor #7 | unstimulated | stimulated |
|---|---|---|
| Collected on 2002 Apr. 6, analyzed 2 days later by the DNase method | 36.2* | 21.8* |

*Estimated amount of DNA in ng per μL of original undiluted saliva sample

Another aspect of the invention features a method of reducing the viscosity of a mucin-containing bodily fluid or tissue by reducing disulfide bonds inherent to mucin, wherein the bodily fluid or tissue is mixed with a composition of the invention that includes a reducing agent. In one embodiment, the bodily fluid is sputum, desirably saliva.

Yet another aspect of the invention features a method of recovering a nucleic acid from sputum that includes the steps of: i) obtaining sputum from a subject, ii) contacting the sputum with a composition of the invention to form a mixture, iii) contacting the mixture with a protease, and iv) recovering the nucleic acid from the mixture.

Suitable proteases include, for example, proteinase K or pronase. The protease may suitably be in a dry form that would become activated once mixed with sputum and a composition of the invention. In one embodiment, the protease is deposited onto an interior surface of the collection device. This can be accomplished by dissolving the protease in a solution made up of equal volumes of 5% sucrose in water and 5% glycerol in ethanol and then, after placing the solution on the surface, removing the volatiles under a controlled vacuum to leave the protease bound to the surface as a sticky residue. If the composition does not contain a reducing agent (or even if it does), a reducing agent can be added at any time prior to isolation of the nucleic from the sample, desirably prior to or concurrently with contacting the sample with a suitable protease.

When sputum is mixed with a composition of the present invention, cells are disrupted, nucleic acids are liberated from the cells, membranous material is solubilized, proteins are stripped from the nucleic acids, and protein digestion begins. If present, a reducing agent in the composition reduces the viscosity of the gel-forming mucin. Incubation can be at room temperature over a relatively long period of time (days or weeks) while samples are being shipped to a laboratory for analysis. If transferred to a laboratory soon after collection, incubation at 55° C. for 4 to 16 hours is sufficient to allow the activated protease to digest the majority of protein to small peptides or amino acids. Under such conditions, nucleic acids and polysaccharides remain relatively intact.

Once digestion is complete, nucleic acid isolation can be performed using any technique known in the art (*Short Protocols in Molecular Biology*, 5th Edition Frederick M. Ausubel, Roger Brent, Robert E. Kingston, David D. Moore, J. G. Seidman, John A. Smith (Editor), Kevin Struhl (Editors). ISBN: 0-471-25092-9. 2002. John Wiley and Sons). In one example, in which SDS is used as a denaturant component of the composition, a "precipitation solution" consisting of, for example, potassium chloride may be added to a portion of the sputum-composition mixture resulting in the precipitation of potassium dodecyl sulfate, after standing on ice to cool the solution. Following a short period of centrifugation to remove the precipitate and any residual insoluble material, the supernatant is collected. At this stage, the supernatant is expected to contain as much as 10-30 nanograms per microliter of DNA. For analyses where as little as 1 nanogram of DNA is sufficient, the sample can be diluted.

When larger amounts of DNA are required, the DNA in the supernatant can be precipitated by the addition of alcohol and redissolved in any suitable buffer. This step has the effect of removing inhibitory components of the composition, which are present to preserve the nucleic acids during transport to the laboratory.

If more highly purified DNA is required, then other known purification steps can be used (*Short Protocols in Molecular Biology*, 5th Edition Frederick M. Ausubel, Roger Brent, Robert E. Kingston, David D. Moore, J. G. Seidman, John A. Smith (Editor), Kevin Struhl (Editors). ISBN: 0-471-25092-9. 2002. John Wiley and Sons), such as extraction with phenol or solid-phase extraction. It should be noted that, because the DNA is in a relatively pure state using the procedures described above, any additional purification steps are made easier when compared to analogous purifications of DNA originating from a blood sample.

The methods of the present invention can be used to isolate nucleic acids from sputum for any application requiring a nucleic acid sample. For example, some specific applications of the methods of the present invention include, but are not limited to, forensic applications, medical applications (including genetic screening and disease typing), and paternity testing.

Another aspect of the invention features a method of preserving and/or recovering a nucleic acid from a bodily fluid that includes, placing the bodily fluid into a first region of a container, placing a composition of the invention into a second region of the container, which is separated from the first region by a barrier, closing the container, and disturbing the integrity of the barrier such that the composition and the bodily fluid are brought into contact. Collection devices of the invention, which also can serve as containers for bring the compositions and nucleic acid-containing bodily fluids together are described below.

Collection Devices

The invention also provides a novel collection device useful for collecting a biological sample from a subject, and subsequently mixing the collected sample with a composition intended to stabilize, preserve, or facilitate the recovery of components of the sample. Such components may include, without limiting the invention, nucleic acids, proteins, peptides, toxins, chitins, fatty acids, and glycogens. Non-limiting examples of biological samples are skin, hair, fecal matter, bodily fluids, and tissue.

Desirably, the invention features a device for preserving and/or recovering a nucleic acid obtained from a biological sample. The device includes: a container that has a first region for collecting a biological sample and a second region containing a composition for preserving a nucleic acid, a barrier between a first region and a second region that keeps the sample and composition separate, a means for closing the container, and a means for disturbing the integrity of the barrier, such that the composition is capable of contacting the bodily sample. In one embodiment, the composition is a composition of the present invention. In another embodiment, the sample is a biological fluid.

The collection device of the invention simultaneously serves several functions. Some of the desirable features of this collection vessel include one or more of the following:

a) it may be constructed of a sturdy breakage-resistant plastic, desirably a biocompatible plastic. Desirably, the container would be constructed from a material that would not leach chemicals into the container's contents;

b) it would have a broad mouth that would make it relatively simple for a subject to place the required volume of fluid sample, desirably expectorated sputum, and most desirably expectorated saliva, into the device's container;

c) the bottom part of the container would be narrow to reduce the overall volume of the container to make it easier to collect the small volume (1-2 milliliters) of fluid that would be expected from a routine sampling, in particular, when the sample is an expectorate. Optionally, the device would contain markings to allow for an estimate of the sample volume collected;

d) the means for closing the container may be a cap that is designed to lock once tightened to become tamper-resistant;

e) the means for closing the container may be a cap that is designed to provide a liquid-tight and/or airtight seal for the container once the cap is fixed into place;

f) the barrier may be a septum or plastic bag compartment that would separate the composition from the fluid until the septum or bag compartment is pierced or the contents otherwise released;

g) the barrier may be in the form of a pivoting partition. In this embodiment, attachment of the lid to the container forces the partition to pivot from its original position of spanning the space between the first region and the second region to a position in which both regions are exposed to each other and contact between the composition contained in one space and the bodily fluid contained in the other space is allowed;

h) the barrier can be press fit, glued, or heat fit into place;

i) the means for closing the container may be coupled to the disestablishment of the barrier; and j) an antimicrobial agent that coats the outside of the device.

Figure 10:
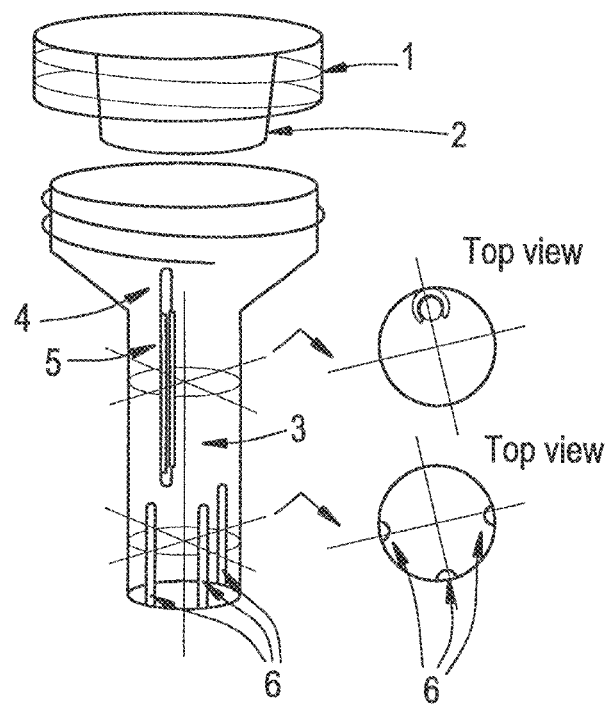
FIG. 10 is an exploded view of a sample container of the invention. Included in the figure is a cross-sectional top view taken at line 1-1 of container 3 showing plunger 4 and plunger channel 5. Also shown is a cross-sectional top view taken at line 2-2 of container 3, showing supports 6 for sealing disc 7 (not shown in this figure but shown in FIG. 11).
Figure 11:
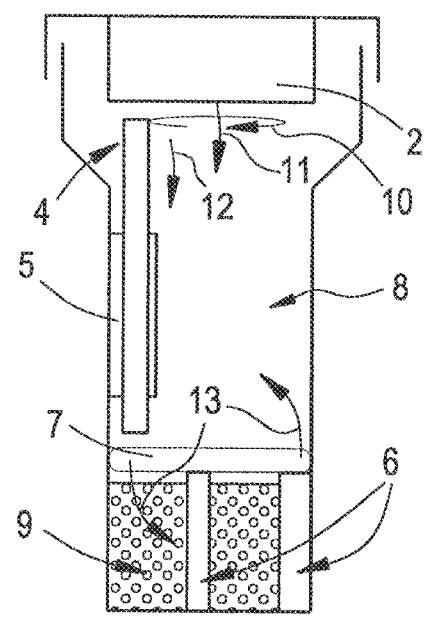
FIG. 11 is a side view of the sample container of FIG. 10, now showing sealing disc 7.

A device of the invention is shown in FIGS. 10 and 11. With cap 1 not attached to the device, a biological sample (not shown) is applied to a first region 8 of container 3, which is separated from a second region 9 by sealing disc 7. After sample application, cap 1 is placed onto the device and secured via a screw thread mechanism to a tight fit, thereby sealing container 3. As the cap is twisted on (shown by dotted line and arrow 10, ram 2, which is attached to cap 1, moves downward as shown by dotted line arrow 11. This downward movement forces plunger 4, which is contained in plunger barrel 5, downward as indicated by dotted line and arrow 12. The downward movement of plunger 4 forces sealing disc 7 to pivot, as shown by dotted line and arrow 13. Pivoting of disc 7 disestablishes the barrier between regions 8 and 9, thereby permitting contact between the sample and a composition of the invention, shown as a dotted solution contained in region 9.

Kits

The present invention also features kits for performing the methods of the invention that include a device of the invention containing a composition of the invention, with instructions for stabilizing, preserving, or facilitating the recovery of nucleic acids from a biological sample by using the device to bring a biological sample into contact with the composition.

EXAMPLES

Example 1

Protocol for Obtaining Saliva Samples from Subjects Capable of Following Instructions The subject is instructed to wait for a period of 20-30 minutes before last eating. The subject will brush his teeth without using toothpaste, if possible. The subject will rinse his mouth vigorously with 50 mL of cool or tepid water. The subject will then spit saliva into the special collection tube until the level of saliva reaches the 2 mL mark. This may take several minutes. If the subject finds that he is unable to deliver sufficient saliva, he will be given a cube of table sugar to chew, and told not to be concerned if some of the sugar is spit into the tube.

When the required amount of saliva is collected, it is mixed with 2 mL of a nucleic acid-preserving composition. The precise way this will be introduced will depend upon the container design.

Once the composition is introduced, the cap is attached to the container and tightened to seal it securely. The container is then vigorously shaken and the process is complete. The DNA is now in an intermediate preserved state. It can be maintained in a frozen state or at any temperature up to about 60° C.

The container can be mailed back to the testing lab at room temperature.

Example 2

Protocol for Obtaining Saliva Samples from Babies, Very Young Children and Infirm Adults Incapable of Following Instructions A rubber or plastic tube or nipple will be introduced into the mouth, attached to a sponge, suction bulb or small syringe, and kept in the mouth for several minutes until visible drooling occurs. A bit of sugar cube will be placed in the mouth to stimulate saliva if necessary. The responsible adult will wear disposable gloves provided for the purpose to avoid contamination with his/her DNA. The responsible adult will draw saliva into the bulb or syringe and transfer it into the collection container. The DNA preserving/extraction composition is introduced and the container is capped and sealed. The tube is vigorously shaken for 1 minute.

Example 3

Preparation of a Nucleic Acid-Preserving Composition

The composition of the nucleic acid-preserving solution used in Examples 4-6 is 33 mM TRIS-HCl, 0.67 M urea, 0.67 M LiCl, 0.6% sodium dodecyl sulfate, 3.3 mM CDTA, 30% ethanol, and 0.25 M sodium ascorbate, all adjusted to a final pH of 8.0. In the examples, the composition is mixed with an equal volume of saliva. Subsequent to these experiments, it has been found that a composition which is 0.3 M TRIS-HCl, 0.67 M urea, 0.67 M NaOAc, 0.6% sodium dodecyl sulfate, 3.3 mM CDTA, 30% ethanol, and 0.1 M sodium ascorbate, all adjusted to a final pH of 8.0, stabilizes DNA for longer periods of time.

Example 4

Extraction of Minimally Purified Chromosomal DNA from the Stimulated Saliva of 8 Different Donors After collection of saliva in an equal volume of the composition as noted in Example 3, followed by 14 days storage at room temperature, a 0.25 mL portion of each donor's sample was treated with proteinase K, centrifuged briefly to remove insoluble material and the DNA therein was precipitated with 2 volumes of ethanol. The precipitate was dissolved in 0.05 mL of water, and an 8 μL aliquot (equivalent to about 20 μL of undiluted saliva) was analyzed by electrophoresis on a 0.8% agarose gel, stained with ethidium bromide to visualize the DNA (see FIG. 1). Of note is the characteristic band of chromosomal DNA present in all samples at the position of the arrow, that corresponds to the position of chromosomal DNA extracted from white blood cells (data not shown).

Example 5

"Real Time" Polymerase Chain Reaction Using DNA from Stimulated Saliva

Figure 2:
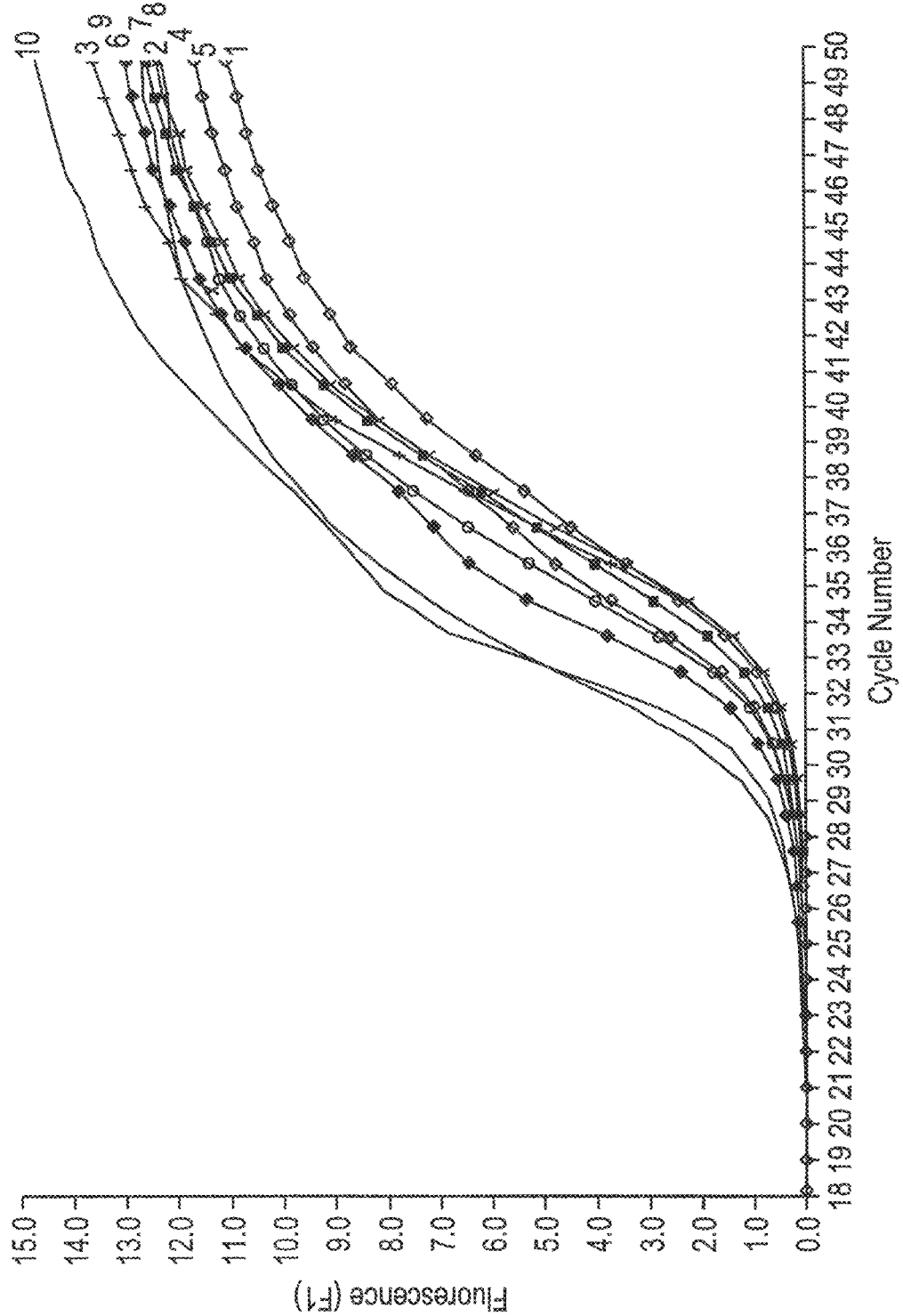
FIG. 2 is a graph illustrating real time PCR of stimulated saliva DNA of Example 5.

Stimulated saliva samples collected on 26 Feb. 2002 (see Table 1) and stored at room temperature were analyzed 62 days later. Minimally purified DNA was prepared as follows: an aliquot was centrifuged to remove insoluble material; to the clarified supernatant was added 2 volumes of ethanol; the precipitate containing DNA was collected by centrifugation and redissolved in water. A volume of the redissolved DNA equivalent to 0.05 microliters of each of the original saliva samples was used for analysis. Real time PCR was carried out using a Roche Light Cycler instrument, where the fluorescent dye SYBR green I was added to follow the reaction (see results of FIG. 2). The primers were designed to detect the human Clotting Factor IX gene (Grant, et al., *J. Immunol. Methods* 225:61-6, 1999). C=control, highly purified white blood cell DNA. Each curve represents results using saliva DNA from different donors, represented by a number. These results using real time PCR demonstrate the suitability of minimally purified saliva DNA from different donors for PCR analysis.

Example 6

"Real Time" Polymerase Chain Reaction Using DNA from Unstimulated Saliva

Figure 3:
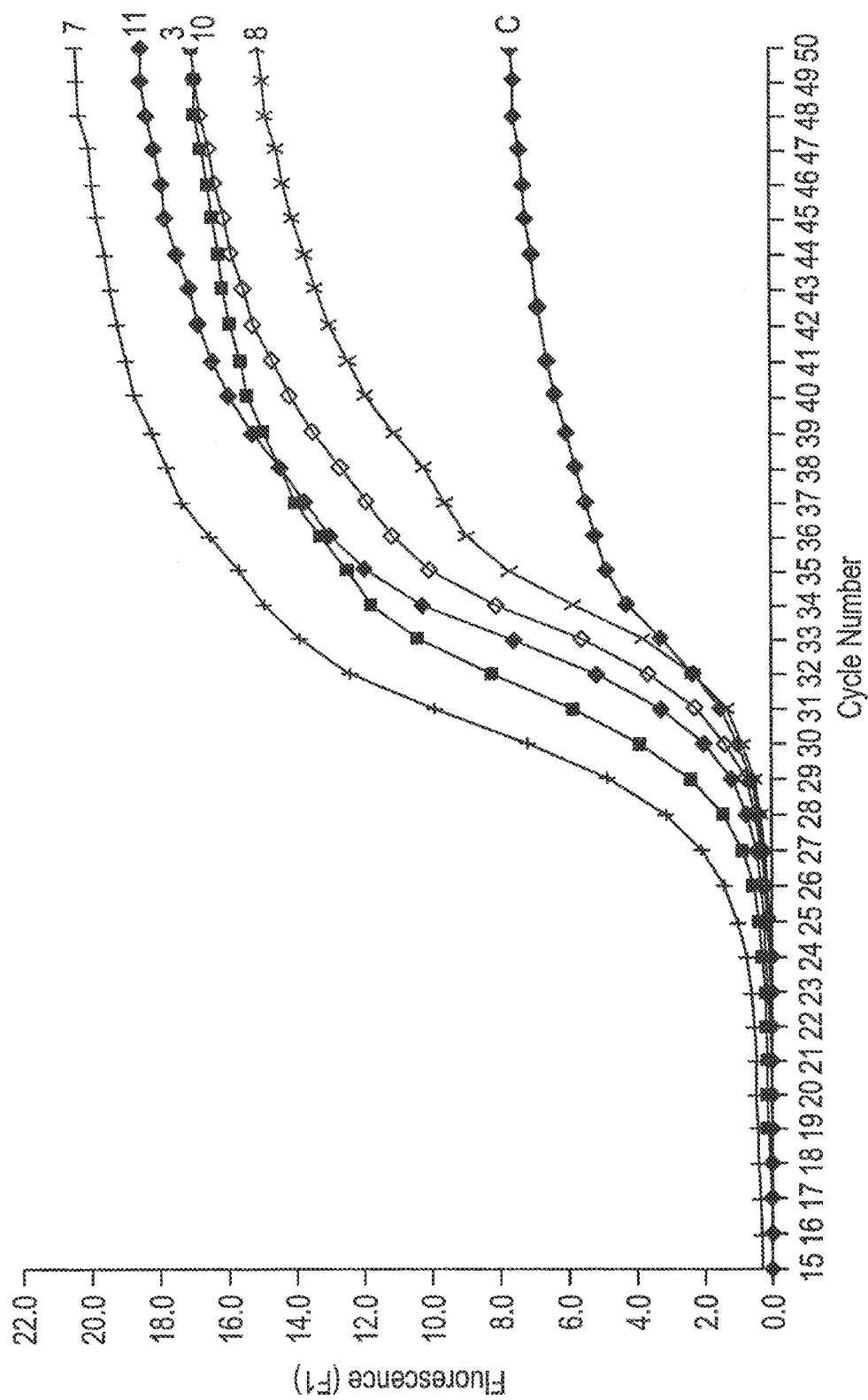
FIG. 3 is a graph illustrating real time PCR of unstimulated saliva DNA of Example 6.
Figure 4:
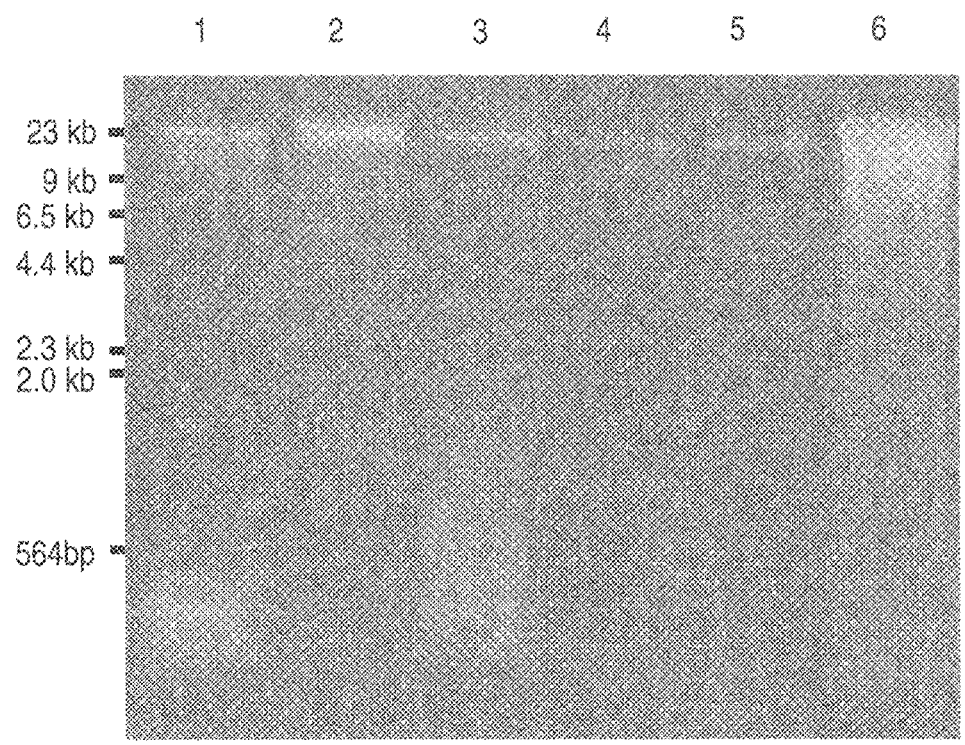
FIG. 4 is an electrophoresis agarose analysis of the DNA in saliva samples mixed with compositions of the invention, the mixtures having been incubated for various times at various temperatures.

FIG. 3 is a graph showing saliva DNA samples collected on 2002 Mar. 25 (see Table 1) and analyzed on 30 days later in accordance with FIG. 1. Minimally purified DNA was used Polymerase chain reaction and other conditions as described in Examples 4 and 5 except saliva collection was done under unstimulated conditions. Numbers refer to individual donors. C is control DNA, a highly purified sample of DNA purified from blood.

Tables 1 and 2 show estimates of DNA recovered from saliva samples. In all cases, the individual donor has been identified by a unique number. These data show that the amount of DNA that can be recovered from this group of donors ranges from 16 micrograms per milliliter of saliva and higher. Estimation of the amount of DNA by chemical methods such as DABA presents some problems and the DNase method provides most reliable results.

Example 7

Stability Studies on DNA from Saliva

Saliva was mixed with an equal volume of the indicated composition and the mixture was incubated for the indicated time period at the indicated temperature (see Table 3). After incubation, approximately 40 μL of mixture was digested briefly with ribonuclease to remove the majority of the RNA present in the sample, then applied to the indicated lane of a 0.8% agarose gel. Following electrophoresis, the gel was stained with ethidium bromide as in Example 4.

TABLE 3

| Lane No. | Composition | Incubation Conditions |
|---|---|---|
| 1 | 0.5M NaOAc, 0.2M TRIS-HCl, 0.15M Na ascorbate, 10 mM CDTA, 1% SDS, 30% (v/v) ethanol, pH = 9.5 | 70° C. for 3 days, then 50° C. for 16 days |
| 2 | 0.5M NaOAc, 0.2M TRIS-HCl, 10 mM CDTA, 1% SDS, 30% (v/v) ethanol, pH = 9.5 | 50° C. for 21 days |
| 3 | 0.5M NaOAc, 0.2M TRIS-HCl, 10 mM CDTA, 1% SDS, 30% (v/v) ethanol, pH = 9.5 | 70° C. for 3 days, then 50° C. for 31 days |
| 4 | 0.67M LiCl, 33 mM TRIS-HCl, 0.67M urea, 0.6% SDS, 3.3 mM CDTA, 30% (v/v) ethanol, pH = 8.0 | 20° C.-25° C. for 15 months |
| 5 | 0.67M LiCl, 33 mM TRIS-HCl, 0.67M urea, 0.6% SDS, 3.3 mM CDTA, 30% (v/v) ethanol, pH = 8.0 | 20° C.-25° C. for 15 months |
| 6 | Control chromosomal DNA prepared from white blood cells | |

Example 8

Rapid Autooxidation of Ascorbate in the Presence of a Transition Metal Ion

A solution of sodium ascorbate (100 μM) in CB (10 mM BES, pH 7.4, containing 1 mM CDTA) was freshly prepared under aerobic (equilibrated with ambient air) conditions. Several spectrophotometric scans over 30 minutes at room temperature showed no change in the absorbance profile (all similar to scan (1)). Scan (2) was taken 3 minutes after addition of a few crystals of $MnCl_2$. The results can be seen in FIG. 6. As shown, 100 μM ascorbate at neutral pH has an absorbance ($\lambda_{max}$=265 nm) of about 1.25 (corresponding to the expected molar extinction coefficient ($A_M$) of about 12,500. Upon addition, the transition metal, manganous chloride, catalyzed the autooxidation of ascorbate, which can conveniently be monitored by a decrease in absorbance at $\lambda$=265 nm (Buettner, *Free Radic. Res. Commun.* 10:5-9, 1990).

Example 9

Spontaneous Autooxidation of Ascorbate

Figure 7:
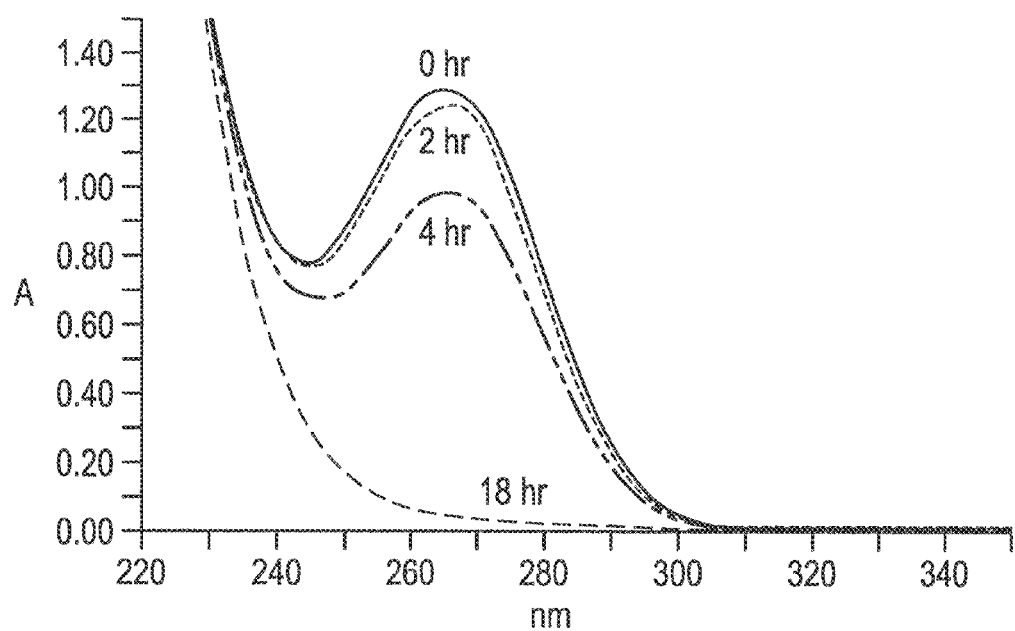
FIG. 7 is a compilation of spectrophotometric scans, at the indicated times, of the 100 µM sodium ascorbate prepared in CB of Example 8. The solution was exposed to ambient atmosphere and temperature between scans but was not contacted with $MnCl_2$ (see Example 9).

Repeated scans at the indicated time points were taken of an aliquot of the 100 μM sodium ascorbate solution prepared in Example 8, before the addition of $MnCl_2$. The sample was exposed to air and maintained at room temperature between scans. The results are illustrated in FIG. 7, and indicate that autooxidation of ascorbate occurs at pH 7.4 can occur over an extended period of time in the presence of low concentrations (1 mM) of CDTA, a "strong" chelator.

Example 10

Stability of Sodium Ascorbate in a Nucleic Acid-Preserving Composition

Figure 8:
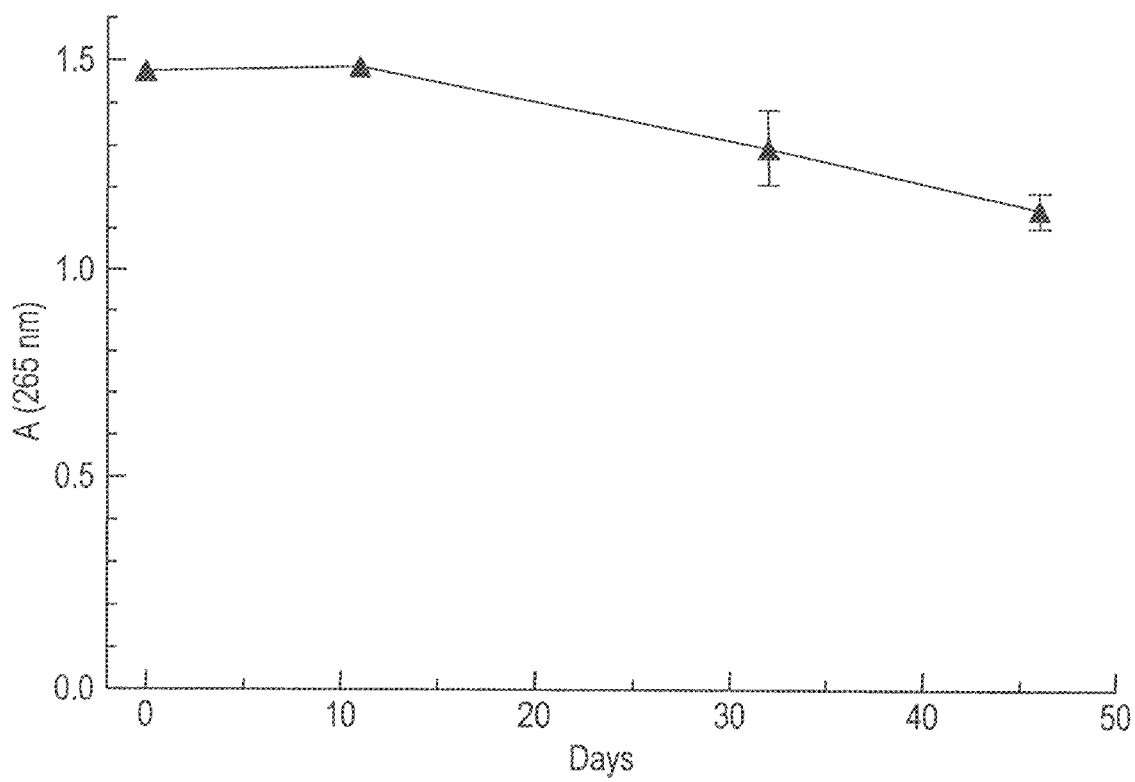
FIG. 8 is a graph of absorbances at 265 nm, obtained at the indicated times, of a solution of sodium ascorbate (250 mM) containing 30 mM Tris-HCl, pH 8.0, 30% ethanol, 3 mM CDTA, mixed with 50 mL of CB, as per Example 10. The stock solution was maintained at room temperature and no precaution was taken to exclude ambient atmosphere or ambient light.
Figure 9:
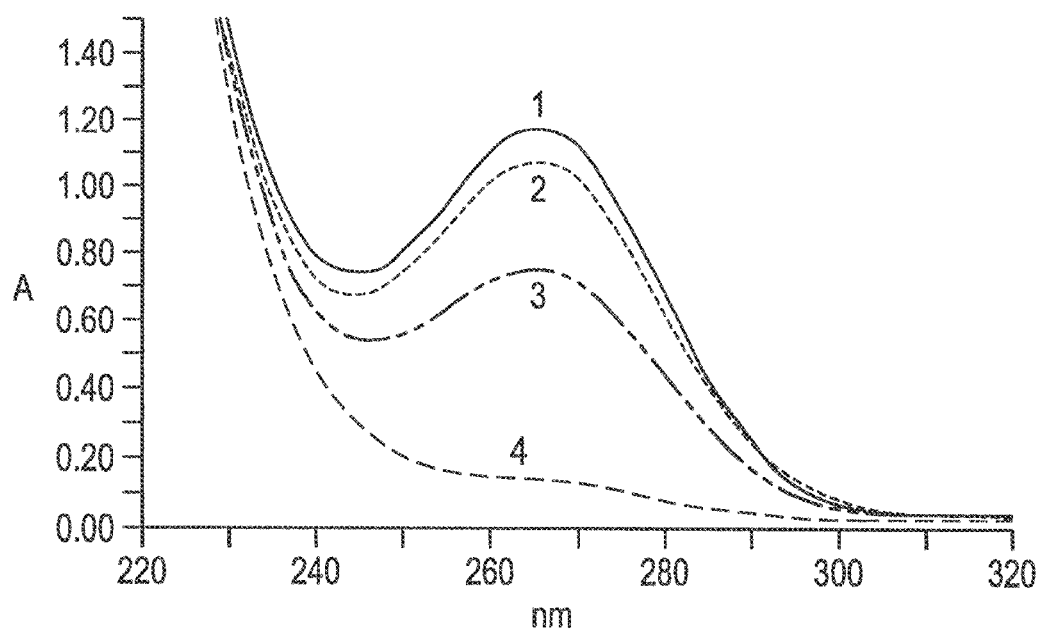
FIG. 9 is a compilation of spectrophotometric scans of the 46 day-old solution prepared in Example 10. Scan 1 (t=46 days) was taken before the addition of $MnCl_2$. Scan 2 was taken 2 minutes after the addition $MnCl_2$. Scan 3 was taken 8 minutes after the addition $MnCl_2$. Scan 4 was taken 27 minutes after the addition $MnCl_2$.

A stock solution of sodium ascorbate (250 mM) was prepared in a solution containing 30 mM Tris-HCl, pH 8.0, 30% ethanol, 3 mM CDTA. 20 μL was removed at the indicated times, mixed with 50 mL of CB (see Example 8) and the absorbance at 265 nm was read immediately. The stock solution was maintained at room temperature. The results are shown in FIG. 8.

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety.

What is claimed is:

1. A method of preserving nucleic acid in a biological sample, the method comprising the steps of:
   a. providing a device for receiving said biological sample, said device having:
      i. one or more walls defining a containment vessel having a top having an opening and a sample receiving area, the sample receiving area for holding said biological sample and having a closed bottom, said opening for sealably receiving a sealing cap and for receiving the biological sample from the mouth of a user, wherein said one or more walls comprise at least one marking corresponding to a fluid volume in the sample receiving area;
      ii. a reagent compartment having a barrier, said barrier sealing and containing reagents in said reagent compartment and being capable of disestablishment to release said reagents into the sample receiving area;
      iii. reagents in the reagent compartment for preserving nucleic acids potentially present in the sample, wherein said reagents comprise a denaturing agent, a chelator and a buffer agent; and
      iv. the sealing cap;
   b. depositing, by expectoration from the user's mouth through the opening, a biological sample in the sample receiving area to the at least one marking; and
   c. affixing the sealing cap to the top,
      wherein affixing the sealing cap to the top comprises sealing the opening,
      wherein affixing the sealing cap to the top comprises mechanically disestablishing the barrier,
      wherein mechanically disestablishing the barrier comprises releasing said reagents to form a mixture of reagents and said biological sample,
      wherein said buffering agent maintains a pH of said mixture equal to or above 5.0 to preserve nucleic acids potentially present in the sample; and
      wherein sealing the opening creates a fluid-tight seal.

2. The method of claim 1, wherein receiving the biological sample comprises receiving a bodily fluid.

3. The method of claim 1, wherein receiving the biological sample comprises receiving sputum.

4. The method of claim 1, wherein receiving the biological sample comprises receiving saliva.

5. The method of claim 1, wherein the denaturing agent comprises dodecyl sulfate.

6. The method of claim 1, wherein the chelator comprises ethylenediamine tetraacetic acid (EDTA).

7. The method of claim 1, wherein the reagents further comprise an antimicrobial agent.

8. The method of claim 1, wherein the reagents further comprise an antioxidant free-radical scavenger.

9. The method of claim 1, wherein the buffering agent comprises TRIS.

10. The method of claim 9, wherein the buffering agent maintains pH of the mixture between about 7.0 and about 10.0.

11. The method of claim 1, wherein the barrier comprises a septum.

12. The method of claim 11, wherein mechanically disestablishing the barrier comprises puncturing or piercing the septum.

13. The method of claim 11, wherein mechanically disestablishing the barrier comprises puncturing the barrier with a piercing member.

14. The method of claim 1, wherein mechanically disestablishing the barrier comprises permanently disestablishing the barrier.

15. The method of claim 1, wherein mechanically disestablishing the barrier comprises displacing the barrier without permanently disestablishing the barrier.

16. The method of claim 15, wherein the barrier is configured to disestablish when displaced by a linear actuator.

17. The method of claim 16, wherein the linear actuator comprises a plunger.

18. The method of claim 1, wherein affixing the sealing cap to the top comprises engaging complimentary threads on the sealing cap and the top.

19. The method of claim 18, wherein engaging threads comprises exerting a force on the barrier, wherein the force is perpendicular to a direction of rotation of the sealing cap.

20. The method of claim 19, wherein exerting the force on the barrier causes the barrier to displace and does not cause permanent disestablishment of the barrier.

21. The method of claim 19, wherein a linear actuator exerts the force on the barrier.

22. The method of claim 1, wherein the device maintains the barrier in a disestablished position while the sealing cap is affixed to the top.

23. The method of claim 22, wherein affixing the sealing cap to the barrier comprises displacing the barrier from a pre-disestablished position to a disestablished position, and wherein the barrier is capable of returning to a pre-disestablished position when the sealing cap is removed from the top.

24. The method of claim 1, wherein affixing the sealing cap to the barrier comprises displacing the barrier from a pre-disestablished position to a disestablished position, and wherein the barrier is capable of returning to a pre-disestablished position when the sealing cap is removed from the top.

25. The method of claim 1, wherein the barrier remains intact when disestablished.

26. The method of claim 25, wherein the barrier is disestablished by a linear actuator.

27. The method of claim 1, wherein affixing the sealing cap to the top comprises engaging the containment vessel and the barrier.

28. The method of claim 27, wherein engaging the containment vessel and the barrier comprises engaging the sealing cap and a plunger, thereby engaging the plunger and the barrier.

29. The method of claim 1, wherein mechanically disestablishing the barrier comprises disestablishing the barrier at room temperature.

30. The method of claim 1, wherein the sealing cap comprises the reagent compartment.

* * * * *